(12) United States Patent
Wang et al.

(10) Patent No.: US 12,129,312 B2
(45) Date of Patent: Oct. 29, 2024

(54) PEPTIDE COMPOUND, APPLICATION THEREOF AND COMPOSITION CONTAINING SAME

(71) Applicant: XDCEXPLORER (SHANGHAI) CO., LTD., Shanghai (CN)

(72) Inventors: Yan Wang, Shanghai (CN); Yvonne Angell, Shanghai (CN); Yun Wu, Shanghai (CN); Manhua Li, Shanghai (CN); Yonghan Hu, Shanghai (CN)

(73) Assignee: XDCEXPLORER (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 16/624,063

(22) PCT Filed: Jun. 27, 2018

(86) PCT No.: PCT/CN2018/093088
§ 371 (c)(1),
(2) Date: Dec. 18, 2019

(87) PCT Pub. No.: WO2019/001459
PCT Pub. Date: Jan. 3, 2019

(65) Prior Publication Data
US 2021/0403506 A1 Dec. 30, 2021

(30) Foreign Application Priority Data

Jun. 27, 2017 (CN) .................. 201710502668.X
Jun. 25, 2018 (CN) .................. 201810662539.1

(51) Int. Cl.
*C07K 7/06* (2006.01)
*A61K 38/00* (2006.01)

(52) U.S. Cl.
CPC ............. *C07K 7/06* (2013.01); *A61K 38/00* (2013.01)

(58) Field of Classification Search
None
See application file for complete search history.

(56) References Cited

U.S. PATENT DOCUMENTS

2007/0099917 A1* 5/2007 Nice ................ A61P 17/06
514/266.4

FOREIGN PATENT DOCUMENTS

| JP | 2010229093 A | 10/2010 |
| WO | 2005000875 A2 | 1/2005 |
| WO | 2013117581 A1 | 8/2013 |

OTHER PUBLICATIONS

Hall et al. ('Discovery of stable non-opioid dynorphin A analogues interacting at the bradykinin receptors for the treatment of neuropathic pain' ACS Chemical Neuroscience v7 2016 pp. 1746-1752). (Year: 2016).*
Kokkonen et al. ('Peptides and pseudopeptides as SIRT6 deacetylation inhibitors' ACS Medicinal Chemistry Letters v3 2012 pp. 969-974). (Year: 2012).*
Vippagunta et al. ('Crystalline solids' Advanced Drug Delivery Reviews v48 2001 pp. 3-26). (Year: 2001).*
First Office Action dated May 11, 2021 issued in CN Patent Application No. 201810682091.X, with English translation, 10 pages.
Second Office Action dated Jul. 15, 2021 issued in CN Patent Application No. 201810682091.X, with English translation, 10 pages.
Extended European Search Report dated Nov. 19, 2020 issued in counterpart European Patent Application No. 188230882, 11 pages.
Invitation pursuant to Rule 62a-1 EPC issued in the counterpart European application No. 18823088.2 dated May 19, 2020.
Sara M. Hall et al: "Discovery of Stable Non-opioid Dynorphin A Analogues Interacting at the Bradykinin Receptors for the Treatment of Neuropathic Pain", ACS Chemical Neuroscience, vol. 7, No. 12, Dec. 21, 2016, pp. 1746-1752.
Partial Supplementary European Search Report issued in the counterpart European application No. 18823088.2 dated Aug. 19, 2020.
Third Office Action dated Oct. 14, 2021 issued in corresponding CN Application No. 201810682091.X, with English translation, 8 pages.
Handbook of Pharmaceutical Salts: Properties, Selection, and Use, P. Heinrich Stahl and Camille G. Wermuth, (Eds.), Wiley-VCH, 2002.
J. Rautio et al., "Prodrugs: design and clinical applications," Nature Reviews Drug Discovery (2008) 7, 255-270.
V. Stella et al., Prodrugs: Challenges and Rewards, Springer, 2007.
Lu et al., "Improved synthesis of 4-Alkoxybenzyl alcohol resin", J.Org.Chem.1981, 46, 3433-3436.
Shimamura, K., et al., "Identification of a Stable Chemerin Analog with Potent Activity Toward ChemR23", Peptides, vol. 30, Jun. 20, 2009.
Roh, S.G., et al., "Physiological Roles of Adipokines, Hepatokines, and Myokines in Ruminants", Asian—Aust. J. Anim. Sci., vol. 29, No. (1), Jan. 31, 2016.
Suzuki, Y., et al., "The Regulation of Chemerin and CMKLR1 Genes Expression by TNF-α, Adiponectin, and Chemerin Analog in Bovine Differentiated Adipocytes", Asian—Aust. J. Anim. Sci., vol. 25, No. (9), Sep. 30, 2012.
International Search Report issued in International Patent Application No. PCT/CN2018/093088 Dtd Sep. 13, 2018.
Written Opinion of the International Searching Authority issued in International Patent Application No. PCT/CN2018/093088 Dtd Sep. 13, 2018.

(Continued)

*Primary Examiner* — Ronald T Niebauer
(74) *Attorney, Agent, or Firm* — FOLEY & LARDNER LLP

(57) ABSTRACT

Disclosed in the present invention are a peptide compound, an application thereof, and a composition containing the same. Provided in the present invention are a peptide compound represented by formula I, a pharmaceutically acceptable salt thereof, a tautomer thereof, a solvate thereof, a crystal form thereof, or a prodrug thereof. The compound has good stability and good activity.

2 Claims, No Drawings

Specification includes a Sequence Listing.

(56) References Cited

OTHER PUBLICATIONS

Notice of Reasons for Refusal dated Apr. 26, 2022 issued in JP Application No. 2019-572139, with English translation, 13 pages.
Office Action dated Jun. 6, 2022 issued in TW Application No. 107122072, with English translation, 11 pages.
Communication pursuant to Article 94(3) EPC dated Nov. 20, 2023 issued in European application No. 18823088.2, 6 pages.

* cited by examiner

PEPTIDE COMPOUND, APPLICATION THEREOF AND COMPOSITION CONTAINING SAME

The present application claims priorities of the Chinese Patent Application No. CN201710502668.X filed on Jun. 27, 2017 and the Chinese Patent Application No. CN201810662539.1 filed on Jun. 25, 2018, the contents of which are incorporated herein by reference in their entireties.

FIELD OF INVENTION

The Sequence Listing is submitted concurrently with the specification as an ASCII formatted text file via EFS-Web, with a file name of "116487-0105-2-SEQ-NEW1", a creation date of Sep. 1, 2021, and a size of 80,804 bytes. The Sequence Listing filed via EFS-Web is part of the specification and is incorporated in its entirety by reference herein.

The present disclosure relates to a peptide compound, a use thereof and a composition containing the same.

Prior Arts

ChemR23 is the primary receptor for Chemerin. In 1996, Owman et al. identified a novel gene sequence from the cDNA library of hepatitis B cells, of which coding protein is highly homologous to the G-protein-coupled receptor (GPCR) family, named ChemR23 (CMKLR1 chemokine receptor 1). ChemR23 is mainly expressed in leukocytes, adipocytes, endothelial cells, epithelial cells, osteoclasts, and vascular smooth muscle cells. Since no ligand was found, ChemR23 had been considered as an orphan receptor. In 2003, Wittamer et al. found that the protein encoded by TIGZ in the inflammatory body fluid is its ligand while searching for a ligand for the G protein-coupled receptor chemR23 (CMKLR1). In order to facilitate correspondence with chemR23, it was named as Chemerin. Chemerin is widely expressed in various tissues of the human body, such as adipose tissue, adrenal gland, liver, lung, pancreas, placenta, ovary, skin, etc., mainly expressed in white adipose tissue, liver and lungs. The adipocytokines Chemerin is a chemotactic membrane-bound protein secreted by adipocytes.

Chemerin gene is also known as tazarotene-induced gene 2 (TIG2) or retinoic acid receptor responder 2 (RARRES2), which was discovered by Nag pal et al. in 1997 when culturing the skin cells of the patients with psoriasis.

The human chemerin gene is localized to the E2DL3 gene. The Chemerin gene encodes a protein comprising 163 amino acid residues, which is an inactive precursor secreted protein, i.e., prochemerin, with a relative molecular mass of 18 KDa. This precursor protein has a low biological activity and it is necessary to further cleave the C-terminus by plasmin, carboxypeptidase or serine protease outside the cell during coagulation, fibrinolysis, and inflammatory cascade to become an active protein. Prochemerin is converted into an active chemerin with a relative molecular mass of 16 kDa after the hydrolysis at C-terminus of sequence by the extracellular protease, which appears in serum, plasma and body fluids. It is currently believed that the reason why endogenously activated chemerin has such a wide and diverse physiological effects may be related to the different enzymatic hydrolysis of chemerin by its multiple extracellular proteases. Chemerin has multiple protease cleavage sites at C-terminus. The researchers also observed that multiple enzymes can cleave chemerin into active proteins and multiple lysis is required to activate chemerin in some cases.

The C-terminus of Chermerin sequence is critical for its biological activity. In order to study the active peptides of chemerin, in recent years, many prochemerin indented end-derived peptides were artificially synthesized to observe their effect on ChemR23, and the shortest chemerin bioactive peptide was found to be chemerin-9. The sequence of human chemerin-9 is chemerin149-157, YFPGQFAFS (SEQ ID NO: 133); the sequence of murine chemerin-9 is chemerin148-156, FLPGQFAFS (SEQ ID NO: 134). The human chemerin-9 and murine chemerin-9 display similar properties.

Chemerin was originally discovered as an inflammatory factor, and it was found that chemerin promotes chemotaxis of immature dendritic cells and macrophages through its receptor CMKLR1. CMKLR1 has been found to be expressed in many immune cells, including inflammatory mediators (monocytes, macrophages, plasma cell expression/myeloid dendritic cells and natural killer cells), vascular endothelial cells as well as neurons, glial cells, spinal cord and retina, immature dendritic cells, myeloid dendritic cells, macrophages, and natural killer cells. It plays an important role in innate immunity, acquired immunity, inflammatory response, lipogenesis and lipid metabolism, and cell proliferation.

Chemerin and its receptor play an important role in the pathology of viral pneumonia and are therefore likely to become antiviral and anti-inflammatory therapies.

Chemerin is involved in a variety of functions, such as promoting the chemotaxis of dendritic cells, macrophages and NK cells to the site of inflammation, inhibiting the synthesis of proinflammatory mediators TNFα and IL-6, increasing adiponectin production, and promoting differentiation and maturation of adipocytes, improving the sensitivity of insulin cells to insulin and glucose uptake, regulating lipolysis, increasing TNF-β synthesis, increasing NF-κβ activity, increasing VEGF and MMPs synthesis and regulating neovascularization and revascularization and so on. Therefore, Chemerin plays an important role in immune response, inflammatory response, lipogenesis and lipid metabolism (involving obesity, fatty liver, diabetes and metabolic syndrome), and has a good application prospect.

Chemerin also plays a role in asthma disease, which is a chronic inflammatory disease of the respiratory tract. Failure to take any anti-inflammatory measures may result in bronchial obstruction or contracture, and may even be life-threatening due to breathing difficulty. Asthma is listed by the World Health Organization as one of the four major chronic diseases. It is also ranked as the second leading cause of death and disability worldwide after cancer. In some western developed countries, the incidence of asthma is as high as 20%, and some even as high as 40%. The prevalence of asthma in China is growing very fast.

Various natural chemokines and their enzymatic cleavage products found in the body are all proteins, which have the disadvantages such as relatively large molecular weight, difficult in preparation, antigenicity, poor stability, etc. It is difficult to mass-produce and carry out experimental researches and drug developments on large animals and human bodies. Therefore, the development of novel polypeptide chemokine factor receptor 1 agonists foreshadows the development of novel methods for the treatment of this series of inflammations and cancers (tumor immunity).

Compared with most of organic small-molecule drugs, the peptide drugs are characterized by high biological activity, small dosage, low toxicity and metabolization into amino acids. Compared with macromolecular proteins or antibody drugs, the peptide drugs have smaller molecular weight with the activity similar to protein, more significant efficiency, capability of being chemical synthesized, high product purity, controllable quality, almost no immunogenicity for small peptides and good prospects for drug development. The research and development of peptide drugs has become an emerging international high-tech field with great market potential.

The following polypeptide sequence was disclosed in the patent JP2010-229093A by BANYU PHARMACEUT CO. LTD.: (D-Tyr)-Phe-Leu-pro-(D-Ser)-Gln-Phe-(D-Ala)-Tic-Ser (SEQ ID NO: 102).

n is 0-2 (e.g., 0, 1 or 2);
each AA0 is independently

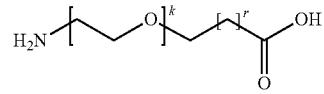

(e.g., PEG8), Ahx, Gly or Beta-Ala; each k is independently 4-8 (e.g., a range of any two endpoints as follows: 4, 5, 6, 7 and 8), each r is independently 0 or 1;

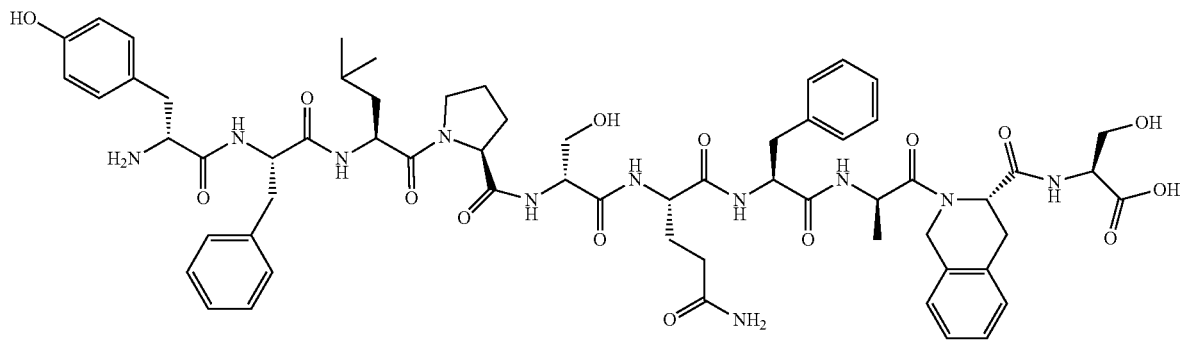 [SMILES: CC(C)C[C@H](NC(=O)[C@H](Cc1ccccc1)NC(=O)[C@H](N)Cc1ccc(O)cc1)C(=O)N1CCC[C@H]1C(=O)N[C@H](CO)C(=O)N[C@@H](CCC(N)=O)C(=O)N[C@@H](Cc1ccccc1)C(=O)N[C@H](C)C(=O)N1Cc2ccccc2C[C@H]1C(=O)N[C@@H](CO)C(=O)O]

Content of the Present Invention

The technical problem to be solved in the present invention is for overcoming deficiencies such as low activity and poor stability of Chemerin. Therefore, the present disclosure provides a peptide compound, a use thereof and a composition containing the same, which has better stability and higher activity.

The present disclosure provides a peptide compound of formula I, a pharmaceutically acceptable salt thereof, a tautomer thereof, a solvate thereof, a crystal form thereof or a prodrug thereof:

$$XX0\text{-}XX1\text{-}XX2\text{-}XX3\text{-}XX4\text{-}XX5\text{-}XX6\text{-}XX7\text{-}XX8\text{-}XX9\text{-}XX10\text{-}P \quad (I)$$

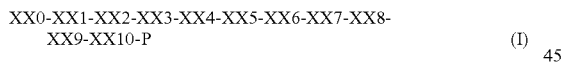

wherein, XX0 is H,
$R^{0-1}$ is $CH_3$—, and q is 10-18 (e.g., a range of any two endpoints as follows: 10, 11, 12, 13, 14, 15, 16, 17 and 18);
PEG is

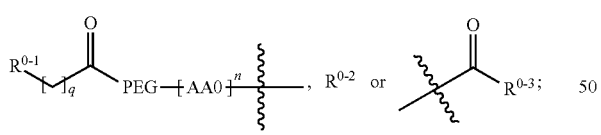

m is 6-12 (e.g., a range of any two endpoints as follows: 6, 7, 8, 9, 10, 11 and 12);

$R^{0-2}$ is a $C_1$-$C_6$ alkyl substituted or unsubstituted by $R^{0-2-1}$ (the number of $R^{0-2-1}$ can be one or more than one {e.g., 1, 2, 3, 4 or 5}; when a plurality of $R^{0-2-1}$ are present, they are the same or different; each $R^{0-2-1}$ can be independently at the terminal or nonterminal site of the $C_1$-$C_6$ alkyl; the $C_1$-$C_6$ alkyl can be a $C_1$-$C_4$ alkyl; the $C_1$-$C_4$ alkyl can be methyl, ethyl, n-propyl, isopropyl, n-butyl, isobutyl, sec-butyl or tert-butyl; the "$C_1$-$C_6$ alkyl substituted by $R^{0-2-1}$" is, for example, 3,5-dihydroxybenzyl or 3-phenylpropyl);

each $R^{0-2-1}$ is independently phenyl substituted or unsubstituted by hydroxyl (the number of the hydroxyl can be one or more than one {e.g., 1, 2, 3, 4 or 5}; each hydroxyl can be independently in ortho, meta or para position of the phenyl; the "phenyl substituted by hydroxyl" is, for example, 3,5-dihydroxyphenyl);

$R^{0-3}$ is a $C_1$-$C_8$ alkyl substituted or unsubstituted by $R^{0-3-1}$ (the number of $R^{0-3-1}$ can be one or more than one {e.g., 1, 2, 3, 4 or 5}; when a plurality of $R^{0-3-1}$ are present, they are the same or different; each $R^{0-3-1}$ can be independently at the terminal or nonterminal site of the $C_1$-$C_8$ alkyl; the $C_1$-$C_8$ alkyl can be a $C_1$-$C_4$ alkyl or a n-pentyl; the $C_1$-$C_4$ alkyl can be methyl, ethyl, n-propyl, isopropyl, n-butyl, isobutyl, sec-butyl or tert-butyl; the "$C_1$-$C_8$ alkyl substituted by $R^{0-3-1}$" is, for example, 2-phenylethyl, 3-phenylpropyl, 4-phenylbutyl, 4-phenylbenzyl, diphenylmethyl, 3,4-dihydroxybenzyl, 3,5-dihydroxybenzyl or cyclohexylmethyl), or phenyl substituted or unsubstituted by $R^{0-3-2}$ (the number of $R^{0-3-2}$ can be one or more than one {e.g., 1, 2, 3, 4 or 5}; when a plurality of $R^{0-3-2}$ are present, they are the same or different; each $R^{0-3-2}$ can be independently in the ortho, meta or para position of the phenyl; the "phenyl substituted by $R^{0-3-2}$" is, for example, 3,5-dihydroxyphenyl, 2,3-dihydroxyphenyl, 2,6-dihydroxyphenyl, 2,3,4-trihydroxyphenyl, 2,3,5-trihydroxyphenyl or 4-trifluoromethylphenyl);

each $R^{0-3-1}$ is independently phenyl substituted or unsubstituted by hydroxyl (the number of the hydroxyl can be one or more than one {e.g., 1, 2, 3, 4 or 5}; each hydroxyl can be independently in ortho, meta or para position of the phenyl; the "phenyl substituted by hydroxyl" is, for example, 3,4-dihydroxyphenyl or 3,5-dihydroxyphenyl), or a $C_3$-$C_6$ cycloalkyl (e.g., cyclohexyl);

each $R^{0-3-2}$ is independently hydroxyl or a $C_1$-$C_4$ alkyl substituted by halogen (the number of the "halogen" can be one or more than one{e.g., 1, 2, 3, 4 or 5}; each "halogen" can be independently fluorine, chlorine or bromine; when a plurality of halogens are present, they are the same or different; the $C_1$-$C_4$ alkyl can be methyl, ethyl, n-propyl, isopropyl, n-butyl, isobutyl, sec-butyl or tert-butyl; the "$C_1$-$C_4$ alkyl substituted by halogen" is, for example, trifluoromethyl);

XX1 is an amino acid selected from the group consisting of D-Tyr (3F), D-Tyr and D-Phe, of which the amino is substituted or unsubstituted by one $C_1$-$C_4$ alkyl (e.g., methyl, ethyl, n-propyl, isopropyl, n-butyl, isobutyl, sec-butyl or tert-butyl, also e.g., methyl) (the "substituted amino acid" is, for example, D-NMeTyr);

XX2 is an amino acid selected from the group consisting of 1Nal, 2Nal, Bpa and

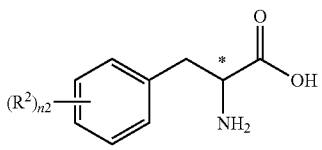

{e.g., Phe, Phe(4-Cl) or Phe(4-Me)}; n2 is 0 or 1, $R^2$ is a $C_1$-$C_4$ alkyl (e.g., methyl, ethyl, n-propyl, isopropyl, n-butyl or isobutyl) or halogen (e.g., fluorine or chlorine), "*" labeled carbon atom is a chiral carbon atom, which is in R-configuration or S-configuration ($R^2$ can be in the ortho, meta or para position of the phenyl, for example, when n2 is 1, $R^2$ can be in the para position of the phenyl; also e.g.,

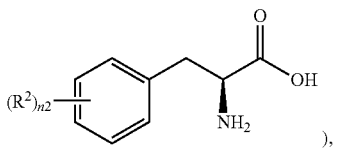

of which the amino is substituted or unsubstituted by one $C_1$-$C_4$ alkyl (e.g., methyl, ethyl, n-propyl, isopropyl, n-butyl, isobutyl, sec-butyl or tert-butyl) (the "substituted amino acid" is, for example, NMePhe);

XX3 is

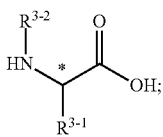

wherein, "*" labeled carbon atom is a chiral carbon atom, which is in R-configuration or S-configuration (e.g.,

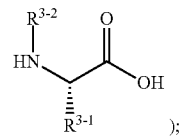

);

$R^{3-1}$ is a $C_4$-$C_5$ alkyl (e.g., n-butyl, isobutyl, sec-butyl, tert-butyl, n-pentyl or 3-methylbutyl) or benzyl; $R^{3-2}$ is a $C_1$-$C_4$ alkyl (e.g., methyl, ethyl, n-propyl, isopropyl, n-butyl, isobutyl, sec-butyl or tert-butyl); (the

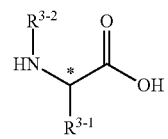

is, for example, NMe-Leu, NMe-Phe, NMe-HoLeu, NEt-Leu, NPr-Leu, NiPr-Leu, Nbu-Leu, NMe-Nle or NMe-Ile);

XX4 is Ala or

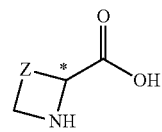

(e.g.,

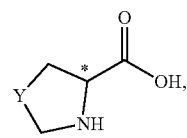

Y is —$(CR^{4-1}R^{4-2})$— {e.g., —$CH_2$—, —CH(OH)— or —$CF_2$}, —$(CH_2)_2$— or —S—; also e.g., Aze, Thz, Hyp, Pro, Pro(5Ph), Pro(4Ph), Pro(diF) or HoPro); "*" labeled carbon atom is a chiral carbon atom, which is in R-configuration or S-configuration (e.g.,

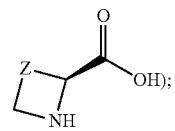

);

Z is —$(CR^{4-1}R^{4-2})_{n4}$— {e.g., —$CH_2$—, —$(CH_2)_2$—, —CH(OH)—$CH_2$—, —$CF_2$—$CH_2$—, —CHPh-$CH_2$—, —$CH_2$—CHPh- or —$(CH_2)_3$-} or —S—$(CR^{4-3}R^{4-4})_{n4'}$— {e.g., —S—$CH_2$—}; the right terminal sites of the —$(CR^{4-1}R^{4-2})_{n4}$— and the —S—$(CR^{4-3}R^{4-4})_{n4'}$— are linked to the chiral carbon atom; n4 is 1-3 (e.g., 1, 2, or 3), n4' is 1 or 2; each of $R^{4-1}$, $R^{4-2}$, $R^{4-3}$ and $R^{4-4}$ is independently hydrogen, hydroxyl, halogen (e.g., fluorine or chlorine) or phenyl;

XX5 is D-Ser, D-Hyp, D-Thr, βAla, D-NMeSer, 2Nal, 1Nal or D-HoSer;

XX6 is Gln, NMe-Gln or NGln;

XX7 is NMe-Phe, HoPhe, 1Nal, 2Nal, Bpa, D-Ser or

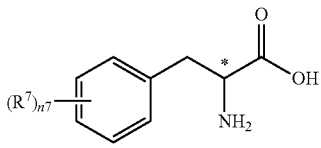

{e.g., Phe, Phe(3-Cl), Phe(3-Me), Phe(3-OMe), Phe(4-OMe), Phe(4-Me) or Phe(4-Cl)}; n7 is 0 or 1, $R^7$ is a $C_1$-$C_4$ alkyl (e.g., methyl, ethyl, n-propyl, isopropyl, n-butyl or isobutyl), a $C_1$-$C_4$ alkoxy (e.g., methoxy, ethoxy, n-propoxy, isopropoxy, n-butoxy or isobutoxy) or halogen (e.g., fluorine or chlorine), "*" labeled carbon atom is a chiral carbon atom, which is in R-configuration or S-configuration ($R^7$ can be in the ortho, meta or para position of the phenyl, for example, when n7 is 1, $R^7$ can be in the para position of the phenyl; also e.g.,

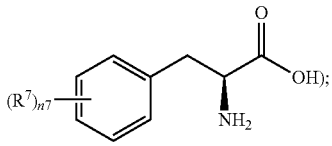

XX8 is D-Ala, D-NMeAla, Ala or βAla;
XX9 is Tic, Phe, NMe-Phe, 1Nal, 2Nal, Bpa, Phe(4-Me), Phe(4-Cl), Phe(4-NO2), HoPhe, Idc, Tic(OH), Oic, Chc, Cha, MeA6c, HoPro, Pro(5Ph), Pro(4Ph), Ala (dip), Bip, azaTic, D-Tic, Ti1c, D-Ti1c, TP5C, TP6C, Tic(6-Me), S-Pip, Ica or D-Oic;
XX10 is NhomoSer, or an amino acid selected from the group consisting of Ser, Thr, Hyp, Asp, D-HoSer and HoSer, of which the amino is substituted or unsubstituted by one $C_1$-$C_4$ alkyl (e.g., methyl, ethyl, n-propyl, isopropyl, n-butyl, isobutyl, sec-butyl or tert-butyl) (the "substituted amino acid" is, for example, NMe-Ser or NMe-HoSer);
P is hydroxyl or amino group.

In one embodiment, the definition of each group in Compound I can be described as follows (unannotated definition is described as any of the preceding embodiments):
wherein, XX0 is H,

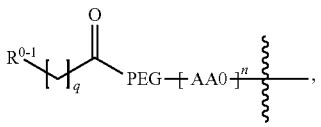

$R^{0-2}$ or

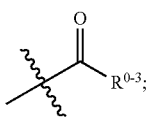

$R^{0-1}$ is $CH_3$—, q is 10-18;

PEG is

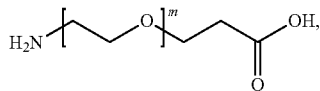

m is 6-12;
n is 0-2;
each AA0 is independently

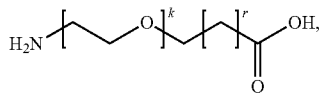

Ahx, Gly or βAla; each k is independently 4-8, each r is independently 0 or 1;
$R^{0-2}$ is a $C_1$-$C_6$ alkyl substituted or unsubstituted by $R^{0-2-1}$;
each $R^{0-2-1}$ is independently phenyl substituted or unsubstituted by hydroxyl;
$R^{0-3}$ is a $C_1$-$C_8$ alkyl substituted or unsubstituted by $R^{0-3-1}$, or phenyl substituted or unsubstituted by $R^{0-3-2}$;
each $R^{0-3-1}$ is independently phenyl substituted or unsubstituted by hydroxyl or a $C_3$-$C_6$ cycloalkyl;
each $R^{0-3-2}$ is independently hydroxyl or a $C_1$-$C_4$ alkyl substituted by halogen;
XX1 is an amino acid selected from the group consisting of D-Tyr (3F), D-Tyr and D-Phe, of which the amino group is substituted or unsubstituted by one $C_1$-$C_4$ alkyl;
XX2 is an amino acid selected from the group consisting of 1Nal, 2Nal, Bpa and

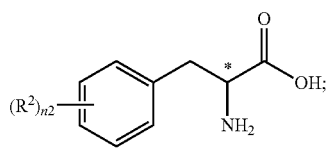

n2 is 0 or 1, $R^2$ is a $C_1$-$C_4$ alkyl or halogen, "*" labeled carbon atom is a chiral carbon atom, which is in R-configuration or S-configuration, of which the amino group is substituted or unsubstituted by one $C_1$-$C_4$ alkyl;
XX3 is

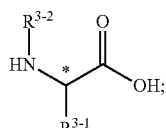

wherein, "*" labeled carbon atom is a chiral carbon atom, which is in R-configuration or S-configuration; $R^{3-1}$ is a $C_4$-$C_5$ alkyl or benzyl; $R^{3-2}$ is a $C_1$-$C_4$ alkyl;

XX4 is Ala or

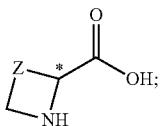

"*" labeled carbon atom is a chiral carbon atom, which is in R-configuration or S-configuration; Z is —(CR$^{4-1}$R$^{4-2}$)$_{n4}$— or —S—(CR$^{4-3}$R$^{4-4}$)$_{n4'}$—; the right terminal sites of the —(CR$^{4-1}$R$^{4-2}$)$_{n4}$— and the —S—(CR$^{4-3}$R$^{4-4}$)$_{n4'}$— are linked to the chiral carbon atom; n4 is 1-3, n4' is 1 or 2; each of R$^{4-1}$, R$^{4-2}$, R$^{4-3}$ and R$^{4-4}$ is independently hydrogen, hydroxyl, halogen or phenyl;

XX5 is D-Ser, D-Hyp, D-Thr, D-NMeSer, 2Nal, 1Nal or D-HoSer;

XX6 is Gln, NMeGln or NGln;

XX7 is NMe-Phe, HoPhe, 1Nal, 2Nal, Bpa, D-Ser or

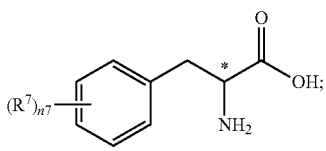

n7 is 0 or 1, R$^7$ is a C$_1$-C$_4$ alkyl, a C$_1$-C$_4$ alkoxy or halogen, "*" labeled carbon atom is a chiral carbon atom, which is in R-configuration or S-configuration;

XX8 is D-Ala, D-NMeAla, Ala or βAla;

XX9 is Tic, Phe, NMePhe, 1Nal, 2Nal, Bpa, Phe(4-Me), Phe(4-Cl), Phe(4-NO2), HoPhe, Idc, Tic(OH), Oic, Chc, Cha, MeA6c, HoPro, Pro(5Ph), Pro(4Ph), Ala(dip), Bip, azaTic, D-Tic, Ti1c, D-Ti1c, TP5C, TP6C, Tic(6-Me), Ica or D-Oic;

XX10 is NHoSer, or an amino acid selected from the group consisting of Ser, Thr, Hyp, Asp, D-HoSer and HoSer, of which the amino group is substituted or unsubstituted by one C$_1$-C$_4$ alkyl;

P is hydroxyl or amino group.

In one embodiment, the definition of each group in Compound I can be described as follows (unannotated definition is described as any of the preceding embodiments):

wherein, XX0 is H,

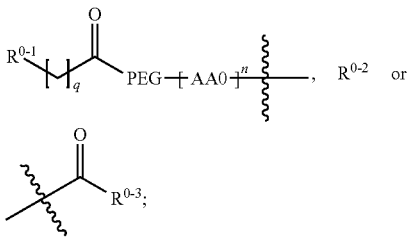

R$^{0-1}$ is CH$_3$—, q is 10-18;

PEG is

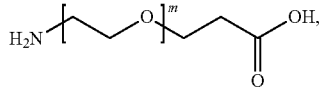

m is 6-12;

n is 0-2;

each AA0 is independently

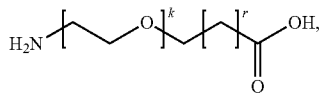

Ahx, Gly or βAla; each k is independently 4-8, each r is independently 0 or 1;

R$^{0-2}$ is a C$_1$-C$_6$ alkyl substituted or unsubstituted by R$^{0-2-1}$;

each R$^{0-2-1}$ is independently phenyl substituted or unsubstituted by hydroxyl;

R$^{0-3}$ is a C$_1$-C$_8$ alkyl substituted or unsubstituted by R$^{0-3-1}$, or phenyl substituted or unsubstituted by R$^{0-3-2}$;

each R$^{0-3-1}$ is independently phenyl substituted or unsubstituted by hydroxyl or a C$_3$-C$_6$ cycloalkyl;

each R$^{0-3-2}$ is independently hydroxyl or a C$_1$-C$_4$ alkyl substituted by halogen;

XX1 is an amino acid selected from the group consisting of D-Tyr (3F), D-Tyr and D-Phe, of which the amino group is substituted or unsubstituted by one C$_1$-C$_4$ alkyl;

XX2 is an amino acid selected from the group consisting of 1Nal, 2Nal, Bpa and

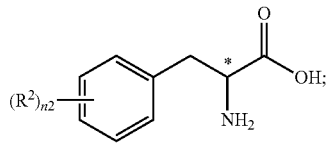

n2 is 0 or 1, R$^2$ is a C$_1$-C$_4$ alkyl or halogen, "*" labeled carbon atom is a chiral carbon atom, which is in R-configuration or S-configuration, of which the amino group is substituted or unsubstituted by one C$_1$-C$_4$ alkyl;

XX3 is

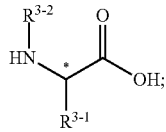

wherein, "*" labeled carbon atom is a chiral carbon atom, which is in R-configuration or S-configuration; R$^{3-1}$ is a C$_4$-C$_5$ alkyl or benzyl; R$^{3-2}$ is a C$_1$-C$_4$ alkyl;

XX4 is Ala or

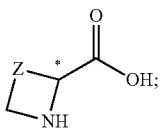

"*" labeled carbon atom is a chiral carbon atom, which is in R-configuration or S-configuration; Z is —(CR$^{4-1}$R$^{4-2}$)$_{n4}$— or —S—(CR$^{4-3}$R$^{4-4}$)$_{n4'}$—; the right terminal sites of the —(CR$^{4-1}$R$^{4-2}$)$_{n4}$— and the —S—(CR$^{4-3}$R$^{4-4}$)$_{n4'}$— are linked to the chiral carbon atom; n4 is 1-3, n4' is 1 or 2; each of R$^{4-1}$, R$^{4-2}$, R$^{4-3}$ and R$^{4-4}$ is independently hydrogen, hydroxyl, halogen or phenyl;

XX5 is D-Ser, D-Hyp, D-Thr, D-NMeSer, 2Nal, 1Nal or D-HoSer;

XX6 is Gln, NMeGln or NGln;

XX7 is NMe-Phe, HoPhe, 1Nal, 2Nal, Bpa, D-Ser or

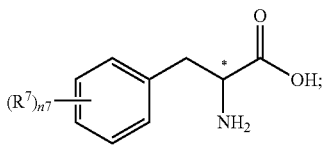

n7 is 0 or 1, R$^7$ is a C$_1$-C$_4$ alkyl, a C$_1$-C$_4$ alkoxy or halogen, "*" labeled carbon atom is a chiral carbon atom, which is in R-configuration or S-configuration;

XX8 is D-Ala, D-NMeA, Ala or βAla;

XX9 is Tic, Phe, NMePhe, 1Nal, 2Nal, Bpa, Phe(4-Me), Phe(4-Cl), Phe(4-NO2), HoPhe, Idc, Tic(OH), Oic, Chc, Cha, MeA6c, Pro(5Ph), Pro(4Ph), Ala(dip), Bip, azaTic, D-Tic, Ti1c, D-Ti1c, TP5C, TP6C, Tic(6-Me), Ica or D-Oic;

XX10 is NHoSer, or an amino acid selected from the group consisting of Ser, Thr, Hyp, Asp, D-HoSer and HoSer, of which the amino group is substituted or unsubstituted by one C$_1$-C$_4$ alkyl;

P is hydroxyl or amino group.

In one embodiment, the definition of each group in Compound I can be described as follows (unannotated definition is described as any of the preceding embodiments):

wherein, XX0 is H,

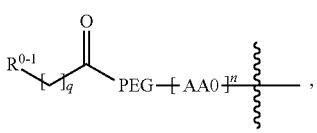

R$^{0-2}$ or

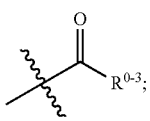

R$^{0-1}$ is CH$_3$—, and q is 10-18 (e.g., a range of any two endpoints as follows: 10, 11, 12, 13, 14, 15, 16, 17 and 18);

PEG is

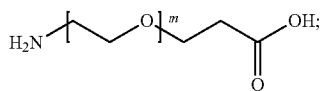

m is 6-12 (e.g., a range of any two endpoints as follows: 6, 7, 8, 9, 10, 11 and 12);

n is 2;

each AA0 is independently Gly or Beta-Ala;

R$^{0-2}$ is a C$_1$-C$_6$ alkyl substituted or unsubstituted by R$^{0-2-1}$ (the number of R$^{0-2-1}$ can be one or more than one {e.g., 1, 2, 3, 4 or 5}; when a plurality of R$^{0-2-1}$ are present, they are the same or different; each R$^{0-2-1}$ can be independently at the terminal or nonterminal site of the C$_1$-C$_6$ alkyl; the C$_1$-C$_6$ alkyl can be a C$_1$-C$_4$ alkyl; the C$_1$-C$_4$ alkyl can be methyl, ethyl, n-propyl, isopropyl, n-butyl, isobutyl, sec-butyl or tert-butyl; the "C$_1$-C$_6$ alkyl substituted by R$^{0-2-1}$" is, for example, 3-phenylpropyl);

each R$^{0-2-1}$ is independently phenyl;

R$^{0-3}$ is a C$_1$-C$_8$ alkyl substituted or unsubstituted by R$^{0-3-1}$ (the number of R$^{0-3-1}$ can be one or more than one {e.g., 1, 2, 3, 4 or 5}; when a plurality of R$^{0-3-1}$ are present, they are the same or different; each R$^{0-3-1}$ can be independently at the terminal or nonterminal site of the C$_1$-C$_8$ alkyl; the C$_1$-C$_8$ alkyl can be a C$_1$-C$_4$ alkyl or n-pentyl; the C$_1$-C$_4$ alkyl can be methyl, ethyl, n-propyl, isopropyl, n-butyl, isobutyl, sec-butyl or tert-butyl; the "C$_1$-C$_8$ alkyl substituted by R$^{0-3-1}$" is, for example, 2-phenylethyl, 3-phenylpropyl, 4-phenylbutyl, 4-phenylbenzyl, diphenylmethyl or cyclohexylmethyl), or phenyl substituted or unsubstituted by R$^{0-3-2}$ (the number of R$^{0-3-2}$ can be one or more than one {e.g., 1, 2, 3, 4 or 5}; when a plurality of R$^{0-3-2}$ are present, they are the same or different; each R$^{0-3-2}$ can be independently in the ortho, meta or para position of the phenyl; the "phenyl substituted by R$^{0-3-2}$" is, for example, 3,5-dihydroxyphenyl, 2,3-dihydroxyphenyl, 2,6-dihydroxyphenyl, 2,3,4-trihydroxyphenyl, 2,3,5-trihydroxyphenyl or 4-trifluoromethylphenyl);

each R$^{0-3-1}$ is independently phenyl or a C$_3$-C$_6$ cycloalkyl (e.g., cyclohexyl);

each R$^{0-3-2}$ is independently a C$_1$-C$_4$ alkyl substituted by halogen (the number of the "halogen" can be one or more than one{e.g., 1, 2, 3, 4 or 5}; each "halogen" can be independently fluorine, chlorine or bromine; when a plurality of halogens are present, they are the same or different; the C$_1$-C$_4$ alkyl can be methyl, ethyl, n-propyl, isopropyl, n-butyl, isobutyl, sec-butyl or tert-butyl; the "C$_1$-C$_4$ alkyl substituted by halogen" is, for example, trifluoromethyl);

XX1 is an amino acid selected from the group consisting of D-Tyr (3F) and D-Tyr, of which the amino group is substituted or unsubstituted by one C$_1$-C$_4$ alkyl (e.g., methyl, ethyl, n-propyl, isopropyl, n-butyl, isobutyl, sec-butyl or tert-butyl, also e.g., methyl) (the "substituted amino acid" is, for example, D-NMeTyr);

XX2 is an amino acid selected from the group consisting of 1Nal, 2Nal, Bpa and

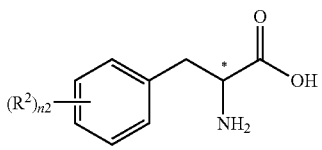

{e.g., Phe, Phe(4-Cl) or Phe(4-Me)}; n2 is 0 or 1, $R^2$ is a $C_1$-$C_4$ alkyl (e.g., methyl, ethyl, n-propyl, isopropyl, n-butyl or isobutyl) or halogen (e.g., fluorine or chlorine), "*" labeled carbon atom is a chiral carbon atom, which is in R-configuration or S-configuration ($R^2$ can be in the ortho, meta or para position of the phenyl, for example, when n2 is 1, $R^2$ can be in the para position of the phenyl; also e.g.,

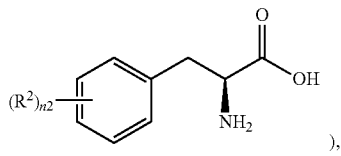

), of which the amino group is substituted or unsubstituted by one $C_1$-$C_4$ alkyl (e.g., methyl, ethyl, n-propyl, isopropyl, n-butyl, isobutyl, sec-butyl or tert-butyl) (the "substituted amino acid" is, for example, NMePhe);

XX3 is

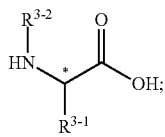

wherein, "*" labeled carbon atom is a chiral carbon atom, which is in R-configuration or S-configuration (e.g.,

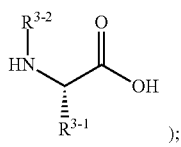

);

$R^{3-1}$ is a $C_4$-$C_5$ alkyl (e.g., n-butyl, isobutyl, sec-butyl, tert-butyl, n-pentyl or 3-methylbutyl) or benzyl; $R^{3-2}$ is a $C_1$-$C_4$ alkyl (e.g., methyl, ethyl, n-propyl, isopropyl, n-butyl, isobutyl, sec-butyl or tert-butyl); (the

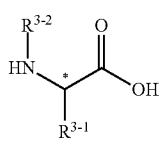

is, for example, NMe-Leu, NMe-Phe, NMe-HoLeu, NEt-Leu, NPr-Leu, NiPr-Leu, Nbu-Leu, NMe-Nle or NMe-Ile);

XX4 is

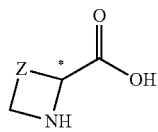

(e.g.,

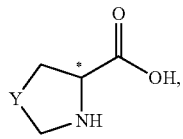

Y is —($CR^{4-1}R^{4-2}$)— {e.g., —$CH_2$—, —CH(OH)— or —$CF_2$}, —($CH_2$)$_2$— or —S—; also e.g., Aze, Thz, Hyp, Pro, Pro(5Ph), Pro(4Ph), Pro(diF) or HoPro); "*" labeled carbon atom is a chiral carbon atom, which is in R-configuration or S-configuration (e.g.,

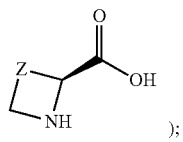

);

Z is —($CR^{4-1}R^{4-2}$)$_{n4}$— {e.g., —$CH_2$—, —($CH_2$)$_2$—, —CH(OH)—$CH_2$—, —$CF_2$—$CH_2$—, —CHPh-$CH_2$—, —$CH_2$—CHPh- or —($CH_2$)$_3$-} or —S—($CR^{4-3}R^{4-4}$)$_{n4'}$— {e.g., —S—$CH_2$—}; the right terminal sites of the —($CR^{4-1}R^{4-2}$)$_{n4}$— and the —S—($CR^{4-3}R^{4-4}$)$_{n4'}$— are linked to the chiral carbon atom; n4 is 1-3 (e.g., 1, 2 or 3), n4' is 1 or 2; each of $R^{4-1}$, $R^{4-2}$, $R^{4-3}$ and $R^{4-4}$ is independently hydrogen, hydroxyl, halogen (e.g., fluorine or chlorine) or phenyl;

XX5 is D-Ser, D-Thr or D-HoSer;

XX6 is Gln;

XX7 is 1Nal, 2Nal or

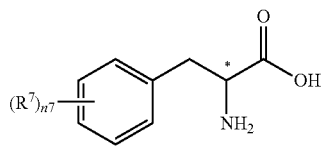

{e.g., Phe, Phe(3-Cl), Phe(3-Me), Phe(3-OMe), Phe(4-OMe), Phe(4-Me) or Phe(4-Cl)}; n7 is 0 or 1, $R^7$ is a $C_1$-$C_4$ alkyl (e.g., methyl, ethyl, n-propyl, isopropyl, n-butyl or isobutyl), a $C_1$-$C_4$ alkoxy (e.g., methoxy, ethoxy, n-propoxy, isopropoxy, n-butoxy or isobutoxy) or halogen (e.g., fluorine or chlorine), "*" labeled carbon atom is a chiral carbon atom, which is in R-configuration or S-configuration ($R^7$ can be in the ortho, meta or para position of the phenyl, for example, when n7 is 1, $R^7$ can be in the para position of the phenyl; also e.g., XX8 is D-Ala;

XX9 is Tic, Phe(4-Me), Phe(4-Cl), D-Ti1c or D-Oic;

XX10 is NhomoSer, or an amino acid selected from the group consisting of Ser and HoSer, of which the amino group is substituted or unsubstituted by one $C_1$-$C_4$ alkyl (e.g., methyl, ethyl, n-propyl, isopropyl, n-butyl, isobutyl, sec-butyl or tert-butyl) (the "substituted amino acid" is, for example, NMe-Ser or NMe-HoSer);

P is hydroxyl or amino group.

In one embodiment, the definition of each group in Compound I can be described as follows (unannotated definition is described as any of the preceding embodiments):

XX0 is H.

In one embodiment, the definition of each group in Compound I can be described as follows (unannotated definition is described as any of the preceding embodiments):

$R^{0-1}$ is $CH_3$—, and q is 10-16;

PEG is m is 6-10;

n is 2;

each AA0 is independently Gly or βAla.

In one embodiment, the definition of each group in Compound I can be described as follows (unannotated definition is described as any of the preceding embodiments):

$R^{0-1}$ is $CH_3$—, and q is 10-16;

PEG is m is 8;

n is 2;

each AA0 is independently Gly or βAla.

In one embodiment, the definition of each group in Compound I can be described as follows (unannotated definition is described as any of the preceding embodiments):

$R^{0-2}$ is a $C_1$-$C_6$ alkyl substituted or unsubstituted by $R^{0-2-1}$;

each $R^{0-2-1}$ is independently phenyl.

In one embodiment, the definition of each group in Compound I can be described as follows (unannotated definition is described as any of the preceding embodiments):

$R^{0-3}$ is a $C_1$-$C_8$ alkyl substituted or unsubstituted by $R^{0-3-1}$ or phenyl substituted or unsubstituted by $R^{0-3-2}$;

each $R^{0-3-1}$ is independently phenyl or a $C_3$-$C_6$ cycloalkyl;

each $R^{0-3-2}$ is independently a $C_1$-$C_4$ alkyl substituted by halogen.

In one embodiment, the definition of each group in Compound I can be described as follows (unannotated definition is described as any of the preceding embodiments):

XX1 is an amino acid selected from the group consisting of D-Tyr (3F) and D-Tyr, of which the amino group is substituted or unsubstituted by one $C_1$-$C_4$ alkyl.

In one embodiment, the definition of each group in Compound I can be described as follows (unannotated definition is described as any of the preceding embodiments):

XX2 is an amino acid selected from the group consisting of 1Nal, 2Nal, Bpa, Phe, Phe(4-Cl) and Phe(4-Me), of which the amino group is substituted or unsubstituted by one $C_1$-$C_4$ alkyl.

In one embodiment, the definition of each group in Compound I can be described as follows (unannotated definition is described as any of the preceding embodiments):

XX3 is NMe-Leu, NMe-Phe, NMe-HoLeu, NEt-Leu, NPr-Leu, NiPr-Leu, Nbu-Leu, NMe-Nle or NMe-Ile.

In one embodiment, the definition of each group in Compound I can be described as follows (unannotated definition is described as any of the preceding embodiments):

XX3 is NMe-Leu, NMe-Phe, NMe-HoLeu, NEt-Leu, NPr-Leu, NiPr-Leu or Nbu-Leu.

In one embodiment, the definition of each group in Compound I can be described as follows (unannotated definition is described as any of the preceding embodiments):

XX4 is

"*" labeled carbon atom is a chiral carbon atom, which is in R-configuration or S-configuration; Z is —$(CR^{4-1}R^{4-2})_{n4}$— or —S—$(CR^{4-3}R^{4-4})$; the right terminal sites of the —$(CR^{4-1}R^{4-2})_{n4}$— and the —S—$(CR^{4-3}R^{4-4})_{n4'}$— are linked to the chiral carbon atom; n4 is 1-3, n4' is 1 or 2; each of $R^{4-1}$, $R^{4-2}$, $R^{4-3}$ and $R^{4-4}$ is independently hydrogen, hydroxyl, halogen or phenyl.

In one embodiment, the definition of each group in Compound I can be described as follows (unannotated definition is described as any of the preceding embodiments):

XX4 is Thz, Hyp, Pro, Pro(5Ph), Pro(4Ph) or Pro(diF).

In one embodiment, the definition of each group in Compound I can be described as follows (unannotated definition is described as any of the preceding embodiments):

XX4 is Thz, Hyp, Pro, Pro(4Ph) or Pro(diF).

In one embodiment, the definition of each group in Compound I can be described as follows (unannotated definition is described as any of the preceding embodiments):

XX5 is D-Ser, D-Thr or D-HoSer.

In one embodiment, the definition of each group in Compound I can be described as follows (unannotated definition is described as any of the preceding embodiments):
XX6 is Gln.

In one embodiment, the definition of each group in Compound I can be described as follows (unannotated definition is described as any of the preceding embodiments):
XX7 is 1Nal, 2Nal or

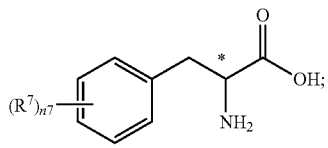

n7 is 0 or 1, $R^7$ is a $C_1$-$C_4$ alkyl, a $C_1$-$C_4$ alkoxy or halogen, "*" labeled carbon atom is a chiral carbon atom, which is in R-configuration or S-configuration.

In one embodiment, the definition of each group in Compound I can be described as follows (unannotated definition is described as any of the preceding embodiments):
XX7 is 1Nal, 2Nal or Phe.

In one embodiment, the definition of each group in Compound I can be described as follows (unannotated definition is described as any of the preceding embodiments):
XX8 is D-Ala.

In one embodiment, the definition of each group in Compound I can be described as follows (unannotated definition is described as any of the preceding embodiments):
XX9 is Tic, Phe, NMePhe, 1Nal, 2Nal, Bpa, Phe(4-Me), Phe(4-Cl), Phe(4-NO2), HoPhe, Idc, Tic(OH), Oic, Chc, Cha, MeA6c, HoPro, Pro(5Ph), Pro(4Ph), Ala(dip), Bip, azaTic, D-Tic, Ti1c, D-Ti1c, TP5C, TP6C, Tic(6-Me), Ica or D-Oic.

In one embodiment, the definition of each group in Compound I can be described as follows (unannotated definition is described as any of the preceding embodiments):
XX9 is Tic, Phe, NMePhe, 1Nal, 2Nal, Bpa, Phe(4-Me), Phe(4-Cl), Phe(4-NO2), HoPhe, Idc, Tic(OH), Oic, Chc, Cha, MeA6c, Pro(5Ph), Pro(4Ph), Ala(dip), Bip, azaTic, D-Tic, Ti1c, D-Ti1c, TP5C, TP6C, Tic(6-Me), Ica or D-Oic.

In one embodiment, the definition of each group in Compound I can be described as follows (unannotated definition is described as any of the preceding embodiments):
XX9 is Tic, Phe(4-Me), Phe(4-Cl), D-Ti1c or D-Oic.

In one embodiment, the definition of each group in Compound I can be described as follows (unannotated definition is described as any of the preceding embodiments):
XX10 is NHoSer, or an amino acid selected from the group consisting of Ser and HoSer, of which the amino group is substituted or unsubstituted by one $C_1$-$C_4$ alkyl.

In one embodiment, the definition of each group in Compound I can be described as follows (unannotated definition is described as any of the preceding embodiments):
P is hydroxyl.

In one embodiment, the definition of each group in Compound I can be described as follows (unannotated definition is described as any of the preceding embodiments):
wherein, XX0 is H,

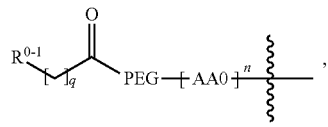

$R^{0-2}$ or

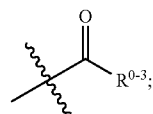

$R^{0-1}$ is $CH_3$—, and q is 10-18 (e.g., a range of any two endpoints as follows: 10, 11, 12, 13, 14, 15, 16, 17 and 18);

PEG is

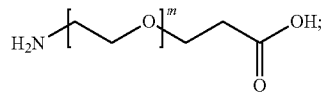

m is 6-10 (e.g., a range of any two endpoints as follows: 6, 7, 8, 9 and 10);

n is 0-2 (e.g., 0, 1 or 2);

each AA0 is independently

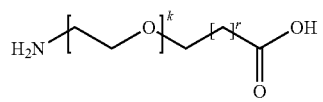

(e.g., PEG8), Ahx, Gly or Beta-Ala; each k is independently 4-8 (e.g., a range of any two endpoints as follows: 4, 5, 6, 7 and 8), each r is independently 0 or 1;

$R^{0-2}$ is a $C_1$-$C_6$ alkyl substituted or unsubstituted by $R^{0-2-1}$ (the number of $R^{0-2-1}$ can be one or more than one {e.g., 1, 2, 3, 4 or 5}; when a plurality of $R^{0-2-1}$ are present, they are the same or different; each $R^{0-2-1}$ can be independently at the terminal or nonterminal sites of the $C_1$-$C_6$ alkyl; the $C_1$-$C_6$ alkyl can be a $C_1$-$C_4$ alkyl; the $C_1$-$C_4$ alkyl can be methyl, ethyl, n-propyl, isopropyl, n-butyl, isobutyl, sec-butyl or tert-butyl; the "$C_1$-$C_6$ alkyl substituted by $R^{0-2-1}$" is, for example, 3,5-dihydroxybenzyl or 3-phenylpropyl);

each $R^{0-2-1}$ is independently phenyl substituted or unsubstituted by hydroxyl (the number of the hydroxyl can be one or more than one {e.g., 1, 2, 3, 4 or 5}; each hydroxyl can be independently in ortho, meta or para position of the phenyl; the "phenyl substituted by hydroxyl" is, for example, 3,5-dihydroxyphenyl);

R⁰⁻³ is a C₁-C₈ alkyl substituted or unsubstituted by R⁰⁻³⁻¹ (the number of R⁰⁻³⁻¹ can be one or more than one {e.g., 1, 2, 3, 4 or 5}; when a plurality of R⁰⁻³⁻¹ are present, they are the same or different; each R⁰⁻³⁻¹ can be independently at the terminal or nonterminal sites of the C₁-C₈ alkyl; the C₁-C₈ alkyl can be a C₁-C₄ alkyl or n-pentyl; the C₁-C₄ alkyl can be methyl, ethyl, n-propyl, isopropyl, n-butyl, isobutyl, sec-butyl or tert-butyl; the "C₁-C₈ alkyl substituted by R⁰⁻³⁻¹" is, for example, 2-phenylethyl, 3-phenylpropyl, 4-phenylbutyl, 4-phenylbenzyl, diphenylmethyl, 3,4-dihydroxybenzyl, 3,5-dihydroxybenzyl or cyclohexylmethyl), or phenyl substituted or unsubstituted by R⁰⁻³⁻² (the number of R⁰⁻³⁻² can be one or more than one {e.g., 1, 2, 3, 4 or 5}; when a plurality of R⁰⁻³⁻² are present, they are the same or different; each R⁰⁻³⁻² can be independently in the ortho, meta or para position of the phenyl; the "phenyl substituted by R⁰⁻³⁻²" is, for example, 3,5-dihydroxyphenyl, 2,3-dihydroxyphenyl, 2,6-dihydroxyphenyl, 2,3,4-trihydroxyphenyl, 2,3,5-trihydroxyphenyl or 4-trifluoromethylphenyl);

each R⁰⁻³⁻¹ is independently phenyl substituted or unsubstituted by hydroxyl (the number of the hydroxyl can be one or more than one {e.g., 1, 2, 3, 4 or 5}; each hydroxyl can be independently in ortho, meta or para position of the phenyl; the "phenyl substituted by hydroxyl" is, for example, 3,4-dihydroxyphenyl or 3,5-dihydroxyphenyl), or a C₃-C₆ cycloalkyl (e.g., cyclohexyl);

each R⁰⁻³⁻² is independently hydroxyl or a C₁-C₄ alkyl substituted by halogen (the number of the "halogen" can be one or more than one{e.g., 1, 2, 3, 4 or 5}; each "halogen" can be independently fluorine, chlorine or bromine; when a plurality of halogens are present, they are the same or different; the C₁-C₄ alkyl can be methyl, ethyl, n-propyl, isopropyl, n-butyl, isobutyl, sec-butyl or tert-butyl; the "C₁-C₄ alkyl substituted by halogen" is, for example, trifluoromethyl);

XX1 is an amino acid selected from the group consisting of D-Tyr and D-Phe, of which the amino group is substituted or unsubstituted by one C₁-C₄ alkyl (e.g., methyl, ethyl, n-propyl, isopropyl, n-butyl, isobutyl, sec-butyl or tert-butyl, also e.g., methyl) (the "substituted amino acid" is, for example, D-NMeTyr);

XX2 is an amino acid selected from the group consisting of 1Nal, 2Nal, Bpa and

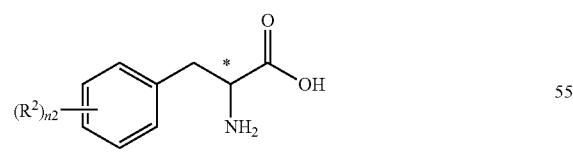

{e.g., Phe, Phe(4-Cl) or Phe(4-Me)}; n2 is 0 or 1, R² is a C₁-C₄ alkyl (e.g., methyl, ethyl, n-propyl, isopropyl, n-butyl or isobutyl) or halogen (e.g., fluorine or chlorine), "*" labeled carbon atom is a chiral carbon atom, which is in R-configuration or S-configuration (R² can be in the ortho, meta or para position of the phenyl, for example, when n2 is 1, R² can be in the para position of the phenyl; also e.g.,

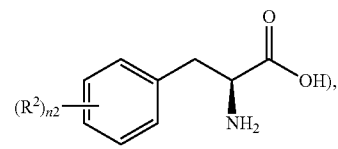

of which the amino group is substituted or unsubstituted by one C₁-C₄ alkyl (e.g., methyl, ethyl, n-propyl, isopropyl, n-butyl, isobutyl, sec-butyl or tert-butyl) (the "substituted amino acid" is, for example, NMePhe);

XX3 is

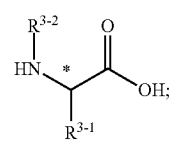

wherein, "*" labeled carbon atom is a chiral carbon atom, which is in R-configuration or S-configuration (e.g.,

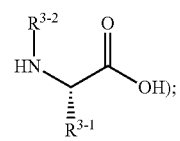

R³⁻¹ is a C₄-C₅ alkyl (e.g., n-butyl, isobutyl, sec-butyl, tert-butyl, n-pentyl or 3-methylbutyl) or benzyl; R³⁻² is a C₁-C₄ alkyl (e.g., methyl, ethyl, n-propyl, isopropyl, n-butyl, isobutyl, sec-butyl or tert-butyl); (the

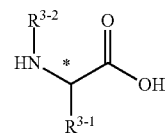

is, for example, NMe-Leu, NMe-Phe, NMe-HoLeu, NEt-Leu, NPr-Leu, NiPr-Leu, Nbu-Leu, NMe-Nle or NMe-Ile);

XX4 is Ala or

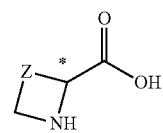

(e.g.,

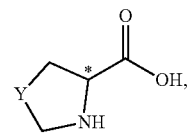

Y is —(CR$^{4-1}$R$^{4-2}$)— {e.g., —CH$_2$—, —CH(OH)— or —CF$_2$}, —(CH$_2$)$_2$— or —S—; also e.g., Aze, Thz, Hyp, Pro, Pro(5Ph), Pro(4Ph), Pro(diF) or HoPro); "*" labeled carbon atom is a chiral carbon atom, which is in R-configuration or S-configuration (e.g.,

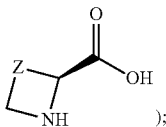
);

Z is —(CR$^{4-1}$R$^{4-2}$)$_{n4}$— {e.g., —CH$_2$—, —(CH$_2$)$_2$—, —CH(OH)—CH$_2$—, —CF$_2$—CH$_2$—, —CHPh-CH$_2$—, —CH$_2$—CHPh- or —(CH$_2$)$_3$-} or —S—(CR$^{4-3}$R$^{4-4}$)$_{n4'}$— {e.g., —S—CH$_2$—}; the right terminal sites of the —(CR$^{4-1}$R$^{4-2}$)$_{n4}$— and the —S—(CR$^{4-3}$R$^{4-4}$)$_{n4'}$— are linked to the chiral carbon atom; n4 is 1-3 (e.g., 1, 2 or 3), n4' is 1 or 2; each of R$^{4-1}$, R$^{4-2}$, R$^{4-3}$ and R$^{4-4}$ is independently hydrogen, hydroxyl, halogen (e.g., fluorine or chlorine) or phenyl;

XX5 is D-Ser, D-Hyp, D-Thr, βAla, D-NMeSer, 2Nal, 1Nal or D-HoSer;

XX6 is Gln, NMe-Gln or NGln;

XX7 is NMe-Phe, HoPhe, 1Nal, 2Nal, Bpa, D-Ser or

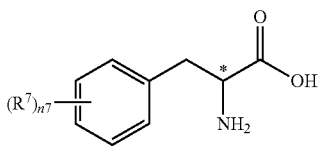

{e.g., Phe, Phe(3-Cl), Phe(3-Me), Phe(3-OMe), Phe(4-OMe), Phe(4-Me) or Phe(4-Cl)}; n7 is 0 or 1, R$^7$ is a C$_1$-C$_4$ alkyl (e.g., methyl, ethyl, n-propyl, isopropyl, n-butyl or isobutyl), a C$_1$-C$_4$ alkoxy (e.g., methoxy, ethoxy, n-propoxy, isopropoxy, n-butoxy or isobutoxy) or halogen (e.g., fluorine or chlorine), "*" labeled carbon atom is a chiral carbon atom, which is in R-configuration or S-configuration (R$^7$ can be in the ortho, meta or para position of the phenyl, for example, when n7 is 1, R$^7$ can be in the para position of the phenyl; also e.g.,

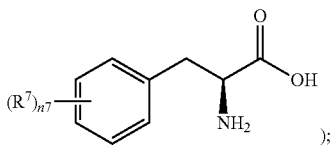
);

XX8 is D-Ala, D-NMeAla, Ala or βAla;

XX9 is Tic, Phe, NMe-Phe, 1Nal, 2Nal, Bpa, Phe(4-Me), Phe(4-Cl), Phe(4-NO2), HoPhe, Idc, Tic(OH), Oic, Chc, Cha, MeA6c, HoPro, Pro(5Ph), Pro(4Ph), Ala(dip), Bip, azaTic, D-Tic, Ti1c, D-Ti1c, TP5C, TP6C, Tic(6-Me), S-Pip, Ica or D-Oic;

XX10 is NhomoSer, or an amino acid selected from the group consisting of Ser, Thr, Hyp, Asp, D-HoSer and HoSer, of which the amino group is substituted or unsubstituted by one C$_1$-C$_4$ alkyl (e.g., methyl, ethyl, n-propyl, isopropyl, n-butyl, isobutyl, sec-butyl or tert-butyl) (the "substituted amino acid" is, for example, NMe-Ser or NMe-HoSer);

P is hydroxyl or amino group.

In one embodiment, the definition of each group in Compound I can be described as follows (unannotated definition is described as any of the preceding embodiments):

XX0 is H,

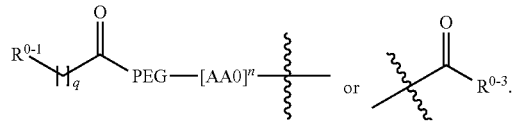

In one embodiment, the definition of each group in Compound I can be described as follows (unannotated definition is described as any of the preceding embodiments):

R$^{0-1}$ is CH$_3$—.

In one embodiment, the definition of each group in Compound I can be described as follows (unannotated definition is described as any of the preceding embodiments):

q is 13-15 (e.g., 13, 14 or 15).

In one embodiment, the definition of each group in Compound I can be described as follows (unannotated definition is described as any of the preceding embodiments):

m is 6-10 (e.g., a range of any two endpoints as follows: 6, 7, 8, 9 and 10).

In one embodiment, the definition of each group in Compound I can be described as follows (unannotated definition is described as any of the preceding embodiments):

n is 2.

In one embodiment, the definition of each group in Compound I can be described as follows (unannotated definition is described as any of the preceding embodiments):

each AA0 is independently Gly or β-Ala.

In one embodiment, the definition of each group in Compound I can be described as follows (unannotated definition is described as any of the preceding embodiments):

R$^{0-3}$ is a C$_1$-C$_8$ alkyl substituted or unsubstituted by phenyl (the number of R$^{0-3-1}$ can be 1 or 2; each phenyl can be independently at the terminal or nonterminal sites of the C$_1$-C$_8$ alkyl; the C$_1$-C$_8$ alkyl can be a C$_1$-C$_4$ alkyl or a n-pentyl; the C$_1$-C$_4$ alkyl can be methyl, ethyl, n-propyl, isopropyl, n-butyl, isobutyl, sec-butyl or tert-butyl; the "C$_1$-C$_8$ alkyl substituted by phenyl" is, for example, 2-phenylethyl, 3-phenylpropyl or 4-phenylbutyl.

In one embodiment, the definition of each group in Compound I can be described as follows (unannotated definition is described as any of the preceding embodiments):

XX1 is D-Tyr, of which the amino group is substituted or unsubstituted by one C$_1$-C$_4$ alkyl (e.g., methyl, ethyl, n-propyl, isopropyl, n-butyl, isobutyl, sec-butyl or tert-butyl) (the "substituted D-Tyr" is, for example, D-NMeTyr).

In one embodiment, the definition of each group in Compound I can be described as follows (unannotated definition is described as any of the preceding embodiments):

XX2 is Phe, of which the amino group is substituted or unsubstituted by one $C_1$-$C_4$ alkyl (e.g., methyl, ethyl, n-propyl, isopropyl, n-butyl, isobutyl, sec-butyl or tert-butyl) (the "substituted Phe" is, for example, NMe-Phe).

In one embodiment, the definition of each group in Compound I can be described as follows (unannotated definition is described as any of the preceding embodiments):

XX3 is

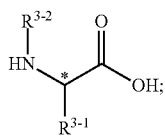

wherein, "*" labeled carbon atom is a chiral carbon atom, which is in R-configuration or S-configuration (e.g.,

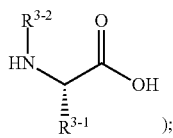

);

$R^{3-1}$ is isobutyl, 3-methylbutyl or benzyl; $R^{3-2}$ is a $C_1$-$C_3$ alkyl (e.g., methyl, ethyl, n-propyl or isopropyl); (the

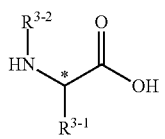

is, for example, NMe-Leu, NMe-HoLeu or NMe-Phe).

In one embodiment, the definition of each group in Compound I can be described as follows (unannotated definition is described as any of the preceding embodiments):

XX4 is

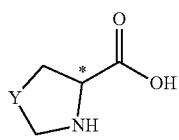

(e.g., Thz, Pro or Pro(diF)); "*" labeled carbon atom is a chiral carbon atom, which is in R-configuration or S-configuration (e.g.,

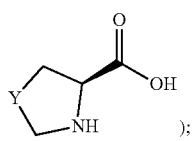

);

Y is —($CR^{4-1}R^{4-2}$)— (e.g., —$CH_2$— or —$CF_2$) or —S—; each of $R^{4-1}$ and $R^{4-2}$ is independently hydrogen or halogen (e.g., fluorine or chlorine).

In one embodiment, the definition of each group in Compound I can be described as follows (unannotated definition is described as any of the preceding embodiments):

XX5 is D-Ser or D-HoSer.

In one embodiment, the definition of each group in Compound I can be described as follows (unannotated definition is described as any of the preceding embodiments):

XX6 is Gln.

In one embodiment, the definition of each group in Compound I can be described as follows (unannotated definition is described as any of the preceding embodiments):

XX7 is Phe, 1Nal or 2Nal.

In one embodiment, the definition of each group in Compound I can be described as follows (unannotated definition is described as any of the preceding embodiments):

XX8 is D-Ala.

In one embodiment, the definition of each group in Compound I can be described as follows (unannotated definition is described as any of the preceding embodiments):

XX9 is Tic, D-Ti1c or D-Oic.

In one embodiment, the definition of each group in Compound I can be described as follows (unannotated definition is described as any of the preceding embodiments):

XX10 is NHoSer, or an amino acid selected from the group consisting of Ser and HoSer, of which the amino group is substituted or unsubstituted by one $C_1$-$C_4$ alkyl (e.g., methyl, ethyl, n-propyl, isopropyl, n-butyl, isobutyl, sec-butyl or tert-butyl) (the "substituted amino acid" is, for example, NMe-Ser or NMe-HoSer).

In one embodiment, the definition of each group in Compound I can be described as follows (unannotated definition is described as any of the preceding embodiments):

P is hydroxyl or amino group.

In one embodiment, the definition of each group in Compound I can be described as follows (unannotated definition is described as any of the preceding embodiments):

wherein, XX0 is H,

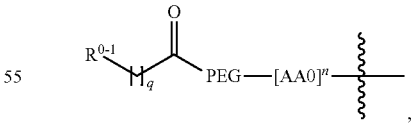

$R^{0-2}$ or

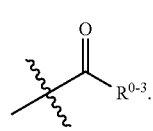

.

In one embodiment, the definition of each group in Compound I can be described as follows (unannotated definition is described as any of the preceding embodiments):
n is 0-2 (e.g., 0, 1 or 2).

In one embodiment, the definition of each group in Compound I can be described as follows (unannotated definition is described as any of the preceding embodiments):
each AA0 is independently

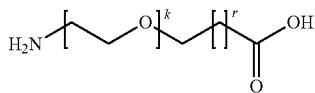

(e.g., PEG8), Ahx, Gly or βAla; each k is independently 4-8 (e.g., a range of any two endpoints as follows: 4, 5, 6, 7 and 8), each r is independently 0 or 1.

In one embodiment, the definition of each group in Compound I can be described as follows (unannotated definition is described as any of the preceding embodiments):
$R^{0-2}$ is a $C_1$-$C_6$ alkyl (the $C_1$-$C_6$ alkyl can be a $C_1$-$C_4$ alkyl; the $C_1$-$C_4$ alkyl can be methyl, ethyl, n-propyl, isopropyl, n-butyl, isobutyl, sec-butyl or tert-butyl).

In one embodiment, the definition of each group in Compound I can be described as follows (unannotated definition is described as any of the preceding embodiments):
$R^{0-3}$ is a $C_1$-$C_8$ alkyl substituted or unsubstituted by $R^{0-3-1}$ (the number of $R^{0-3-1}$ can be one or more than one {e.g., 1, 2, 3, 4 or 5}; when a plurality of $R^{0-3-1}$ are present, they are the same or different; each $R^{0-3-1}$ can be independently at the terminal or nonterminal sites of the $C_1$-$C_8$ alkyl; the $C_1$-$C_8$ alkyl can be a $C_1$-$C_4$ alkyl or n-pentyl; the $C_1$-$C_4$ alkyl can be methyl, ethyl, n-propyl, isopropyl, n-butyl, isobutyl, sec-butyl or tert-butyl; the "$C_1$-$C_8$ alkyl substituted by $R^{0-3-1}$" is, for example, 2-phenylethyl or cyclohexylmethyl), or phenyl substituted or unsubstituted by hydroxyl (the number of the hydroxyl can be one or more than one {e.g., 1, 2, 3, 4 or 5}; each hydroxyl can be independently in the ortho, meta or para position of the phenyl; the "phenyl substituted by hydroxyl" is, for example, 3,5-dihydroxyphenyl).

In one embodiment, the definition of each group in Compound I can be described as follows (unannotated definition is described as any of the preceding embodiments):
each $R^{0-3-1}$ is independently phenyl or a $C_3$-$C_6$ cycloalkyl (e.g., cyclohexyl).

In one embodiment, the definition of each group in Compound I can be described as follows (unannotated definition is described as any of the preceding embodiments):
XX1 is D-NMeTyr, D-Tyr, D-Phe or D-NMePhe.

In one embodiment, the definition of each group in Compound I can be described as follows (unannotated definition is described as any of the preceding embodiments):
XX3 is NMe-Leu, NEt-Leu, NPr-Leu, NiPr-Leu, NMe-HoLeu, NMe-Nle or NMe-Ile.

In one embodiment, the definition of each group in Compound I can be described as follows (unannotated definition is described as any of the preceding embodiments):
XX4 is Thz, Pro, Pro(4Ph), Pro(diF), HoPro or Hyp.

In one embodiment, the definition of each group in Compound I can be described as follows (unannotated definition is described as any of the preceding embodiments):
XX7 is 1Nal, 2Nal, Bpa, Phe, Phe(3-Cl), Phe(4-Cl), Phe(4-Me), Phe(3-Me), Phe(3-OMe), Phe(4-OMe) or HoPhe.

In one embodiment, the definition of each group in Compound I can be described as follows (unannotated definition is described as any of the preceding embodiments):
XX9 is Tic, D-Tic, DTi1c, D-Oic, TP5C or TP6C.

In one embodiment, the definition of each group in Compound I can be described as follows (unannotated definition is described as any of the preceding embodiments):
XX10 is NMe-Ser, NHoSer, NMe-HoSer, D-HoSer, HoSer or Ser.

In one embodiment, the definition of each group in Compound I can be described as follows (unannotated definition is described as any of the preceding embodiments):
$R^{0-3}$ is a $C_1$-$C_8$ alkyl substituted or unsubstituted by phenyl (the number of the phenyl can be one or more than one {e.g., 1, 2, 3, 4 or 5}; each phenyl can be independently at the terminal or nonterminal sites of the $C_1$-$C_8$ alkyl; the $C_1$-$C_8$ alkyl can be a $C_1$-$C_4$ alkyl or a n-pentyl; the $C_1$-$C_4$ alkyl can be methyl, ethyl, n-propyl, isopropyl, n-butyl, isobutyl, sec-butyl or tert-butyl; the "$C_1$-$C_8$ alkyl substituted by phenyl" is, for example, 2-phenylethyl), or phenyl substituted or unsubstituted by hydroxyl (the number of the hydroxyl can be one or more than one {e.g., 1, 2, 3, 4 or 5}; each hydroxyl can be independently in the ortho, meta or para position of the phenyl; the "phenyl substituted by hydroxyl" is, for example, 3,5-dihydroxyphenyl)

In one embodiment, the definition of each group in Compound I can be described as follows (unannotated definition is described as any of the preceding embodiments):
XX1 is D-NMeTyr or D-Tyr.

In one embodiment, the definition of each group in Compound I can be described as follows (unannotated definition is described as any of the preceding embodiments):
XX3 is NMe-Leu, NEt-Leu or NMe-HoLeu.

In one embodiment, the definition of each group in Compound I can be described as follows (unannotated definition is described as any of the preceding embodiments):
XX4 is Thz, Pro or Pro(diF).

In one embodiment, the definition of each group in Compound I can be described as follows (unannotated definition is described as any of the preceding embodiments):
XX7 is 1Nal, 2Nal or Phe.

In one embodiment, the definition of each group in Compound I can be described as follows (unannotated definition is described as any of the preceding embodiments):
XX9 is Tic, D-Tic or DTi1c.

In one embodiment, the definition of each group in Compound I can be described as follows (unannotated definition is described as any of the preceding embodiments):
XX10 is NMe-Ser, NHoSer or Ser.

In one embodiment, Compound I can be selected from the group consisting of

| Peptide No. | | Sequence | SEQ ID NO: |
|---|---|---|---|
| YW-98 | MC9(D-Y147, NMeL149, D-S151, D-A154, Tic155) | (D-Tyr)-Phe-(NMe-Leu)-Pro-(D-Ser)-Gln-Phe-(D-Ala)-Tic-Ser | 1 |
| YW-100 | MC9(D-Y147, NMeF149, D-S151, D-A154, Tic155) | (D-Tyr)-Phe-(NMe-Phe)-Pro-(D-Ser)-Gln-Phe-(D-Ala)-Tic-Ser | 2 |
| YW-101 | MC9(D-Y147, NMeHL149, D-S151, D-A154, Tic155) | (D-Tyr)-Phe-(NMe-HoLeu)-Pro-(D-Ser)-Gln-Phe-(D-Ala)-Tic-Ser | 3 |
| YW-105 | MC9(D-Y147, NMeF148, NMeL149, D-S151, D-A154, Tic155) | (D-Tyr)-(NMe-Phe)-(NMe-Leu)-Pro-(D-Ser)-Gln-Phe-(D-Ala)-Tic-Ser | 4 |
| YW-111 | MC9(3PPA, D-Y147, NMeL149, D-S151, D-A154, Tic155) | 3-Phenylpropanoyl-(D-Tyr)-Phe-(NMe-Leu)-Pro-(D-Ser)-Gln-Phe-(D-Ala)-Tic-Ser | 5 |
| YW-121 | MC9(D-Y147, NMeL149, Thz150, D-S151, D-A154, Tic155) | (D-Tyr)-Phe-(NMe-Leu)-Thz-(D-Ser)-Gln-Phe-(D-Ala)-Tic-Ser | 6 |
| YW-122 | MC9(D-Y147, NMeL149, Thz150, D-S151, 2Nal153, D-A154, Tic155) | (D-Tyr)-Phe-(NMe-Leu)-Thz-(D-Ser)-Gln-2Nal-(D-Ala)-Tic-Ser | 7 |
| YW-123 | MC9(D-NMeY147, NMeL149, Thz150, D-S151, D-A154, Tic155) | (NMe-D-Tyr)-Phe-(NMe-Leu)-Thz-(D-Ser)-Gln-Phe-(D-Ala)-Tic-Ser | 8 |
| YW-124 | MC9(D-NMeY147, NMeL149, Thz150, D-S151, D-A154, Tic155, NMeS156) | (NMe-D-Tyr)-Phe-(NMe-Leu)-Thz-(D-Ser)-Gln-Phe-(D-Ala)-Tic-(NMe-Ser) | 9 |
| YW-125 | MC9(D-NMeY147, NMeL149, Thz150, D-S151, 2Nal153, D-A154, Tic155, NMeS156) | (NMe-D-Tyr)-Phe-(NMe-Leu)-Thz-(D-Ser)-Gln-2Nal-(D-Ala)-Tic-(NMe-Ser) | 10 |
| YW-133 | MC9(Palm-PEG8, G145, G146, D-Y147, NMeL149, D-S151, D-A154, Tic155) | Palm-PEG8-Gly-Gly-(D-Tyr)-Phe-(NMe-Leu)-Pro-(D-Ser)-Gln-Phe-(D-Ala)-Tic-Ser | 11 |
| YW-134 | MC9(Palm-PEG8, βA145, βA146, D-Y147, NMeL149, D-S151, D-A154, Tic155) | Palm-PEG8-βAla-βAla-(D-Tyr)-Phe-(NMe-Leu)-Pro-(D-Ser)-Gln-Phe-(D-Ala)-Tic-Ser | 12 |
| YW-142 | MC9(D-NMeY147, NMeL149, Thz150, D-S151, 1Nal153, D-A154, Tic155, NMeS156) | (NMe-D-Tyr)-Phe-(NMe-Leu)-Thz-(D-Ser)-Gln-1Nal-(D-Ala)-Tic-(NMe-Ser) | 13 |
| YW-146 | MC9(D-NMeY147, NMeL149, D-S151, 2Nal153, D-A154, Tic155, NMeS156) | (NMe-D-Tyr)-Phe-(NMe-Leu)-Pro-(D-Ser)-Gln-2Nal-(D-Ala)-Tic-(NMe-Ser) | 14 |
| YW-148 | MC9(D-NMeY147, NMeL149, Thz150, D-S151, 2Nal153, D-A154, Tic155) | (D-NMe-Tyr)-Phe-(NMe-Leu)-Thz-(D-Ser)-Gln-2Nal-(D-Ala)-Tic-Ser | 15 |
| YW-153 | MC9(D-Y147, NMeL149, D-S151, D-A154, D-Tic155) | (D-Tyr)-Phe-(NMe-Leu)-Pro-(D-Ser)-Gln-Phe-(D-Ala)-(D-Tic)-Ser | 16 |
| YW-161 | MC9(3-phenylpropanoyl, D-Y147, NMeL149, D-S151, D-A154, Tic155, NH2) | 3-Phenylpropanoyl-(D-Tyr)-Phe-(NMe-Leu)-Pro-(D-Ser)-Gln-Phe-(D-Ala)-Tic-Ser-NH2 | 17 |
| YW-162 | MC9(D-NMeY147, NMeL149, D-S151, 1Nal153, D-A154, Tic155, NMeS156) | (D-NMe-Tyr)-Phe-(NMe-Leu)-Pro-(D-Ser)-Gln-1Nal-(D-Ala)-Tic-(NMe-Ser) | 18 |

-continued

| Peptide No. | | Sequence | SEQ ID NO: |
|---|---|---|---|
| YW-163 | MC9(D-NMeY147, NMeL149, D-S151, D-A154, Tic155) | (D-NMe-Tyr)-Phe-(NMe-Leu)-Pro-(D-Ser)-Gln-Phe-(D-Ala)-Tic-Ser | 19 |
| YW-164 | MC9(D-Y147, NMeL149, D-S151, 2Nal153, D-A154, Tic155) | (D-Tyr)-Phe-(NMe-Leu)-Pro-(D-Ser)-Gln-2Nal-(D-Ala)-Tic-Ser | 20 |
| YW-165 | MC9(D-Y147, NMeL149, D-S151, 1Nal153, D-A154, Tic155) | (D-Tyr)-Phe-(NMe-Leu)-Pro-(D-Ser)-Gln-1Nal-(D-Ala)-Tic-Ser | 21 |
| YW-166 | MC9(D-Y147, NMeL149, D-S151, D-A154, Tic155, NMeS156) | (D-Tyr)-Phe-(NMe-Leu)-Pro-(D-Ser)-Gln-Phe-(D-Ala)-Tic-(NMe-Ser) | 22 |
| YW-167 | MC9(D-NMeY147, NMeL149, D-S151, 2Nal153, D-A154, Tic155) | (D-NMe-Tyr)-Phe-(NMe-Leu)-Pro-(D-Ser)-Gln-2Nal-(D-Ala)-Tic-Ser | 23 |
| YW-168 | MC9(D-NMeY147, NMeL149, D-S151, 1Nal153, D-A154, Tic155) | (D-NMe-Tyr)-Phe-(NMe-Leu)-Pro-(D-Ser)-Gln-1Nal-(D-Ala)-Tic-Ser | 24 |
| YW-171 | MC9(D-Y147, NMeL149, D-S151, D-A154, Tic155, HoSer156) | (D-Tyr)-Phe-(NMe-Leu)-Pro-(D-Ser)-Gln-Phe-(D-Ala)-Tic-(HoSer) | 25 |
| YW-172 | MC9(D-Y147, NMeL149, D-S151, D-A154, Tic155, NHoSer156) | (D-Tyr)-Phe-(NMe-Leu)-Pro-(D-Ser)-Gln-Phe-(D-Ala)-Tic-(NHoSer) | 26 |
| YW-174 | MC9(D-Y147, NMeL149, Pro(diF)150, D-S151, D-A154, Tic155) | (D-Tyr)-Phe-(NMe-Leu)-Pro(diF)-(D-Ser)-Gln-Phe-(D-Ala)-Tic-Ser | 27 |
| YW-175 | MC9(D-Y147, NMeL149, D-HoSer151, D-A154, Tic155) | (D-Tyr)-Phe-(NMe-Leu)-Pro-(D-HoSer)-Gln-Phe-(D-Ala)-Tic-Ser | 28 |
| YW-176 | MC9(D-Y147, NMeL149, D-S151, D-A154, D-Oic155) Ser | (D-Tyr)-Phe-(NMe-Leu)-Pro-(D-Ser)-Gln-Phe-(D-Ala)-(D-Oic)-Ser | 29 |
| YW-177 | MC9(D-Y147, NMeL149, D-S151, D-A154, Tic155, NMeHoS156) | (D-Tyr)-Phe-(NMe-Leu)-Pro-(D-Ser)-Gln-Phe-(D-Ala)-Tic-(NMe-HoSer) | 30 |
| YW-178 | MC9(Palm-PEG8, G145, G146, D-NMeY147, NMeL149, D-S151, 2Nal153, D-A154, Tic155 NMeS156) | Palm-PEG8-Gly-Gly-(D-NMe-Tyr)-Phe-(NMe-Leu)-Pro-(D-Ser)-Gln-2Nal-(D-Ala)-Tic-(NMe-Ser) | 31 |
| YW-179 | MC9(Palm-PEG8, betaA145, betaA146, D-NMeY147, NMeL149, D-S151, 2Nal153, D-A154, Tic155 NMeS156) | Palm-PEG8-βAla-βAla-(D-NMe-Tyr)-Phe-(NMe-Leu)-Pro-(D-Ser)-Gln-2Nal-(D-Ala)-Tic-(NMe-Ser) | 32 |
| YW-180 | MC9(tetradecanoyl-PEG8, βA145, βA146, D-NMeY147, NMeL149, D-S151, 2Nal153, D-A154, Tic155, NMeS156) | Tetradecanoyl-PEG8-βAla-βAla-(D-NMe-Tyr)-Phe-(NMe-Leu)-Pro-(D-Ser)-Gln-2Nal-(D-Ala)-Tic-(NMe-Ser) | 33 |
| YW-181 | MC9(dodecanoyl-PEG8, βA145, βA146, D-NMeY147, NMeL149, D-S151, 2Nal153, D-A154, Tic155, NMeS156) | Dodecanoyl-PEG8-βAla-βAla-(NMe-D-Tyr)-Phe-(NMe-Leu)-Pro-(D-Ser)-Gln-2Nal-(D-Ala)-Tic-(NMe-Ser) | 34 |

-continued

| Peptide No. | | Sequence | SEQ ID NO: |
|---|---|---|---|
| YW-182 | MC9(D-Y147, NMeL149, D-S151, D-A154, D-Tic155, NMeS156) | (D-Tyr)-Phe-(NMe-Leu)-Pro-(D-Ser)-Gln-Phe-(D-Ala)-(D-Tic)-(NMe-Ser) | 35 |
| YW-183 | MC9(D-Y147, NEtL149, D-S151, D-A154, Tic155) | (D-Tyr)-Phe-(NEt-Leu)-Pro-(D-Ser)-Gln-Phe-(D-Ala)-Tic-Ser | 36 |
| YW-184 | MC9(D-Y147, NprL149, D-S151, D-A154, Tic155) | (D-Tyr)-Phe-(NPr-Leu)-Pro-(D-Ser)-Gln-Phe-(D-Ala)-Tic-Ser | 37 |
| YW-185 | MC9(3-phenylpropanoyl, D-Y147, NEtL149, D-S151, D-A154, Tic155) | 3-Phenylpropanoyl-(D-Tyr)-Phe-(NEt-Leu)-Pro-(D-Ser)-Gln-Phe-(D-Ala)-Tic-Ser | 38 |
| YW-186 | MC9(3-phenylpropanoyl, D-Y147, NprL149, D-S151, D-A154, Tic155) | 3-Phenylpropanoyl-(D-Tyr)-Phe-(NPr-Leu)-Pro-(D-Ser)-Gln-Phe-(D-Ala)-Tic-Ser | 39 |
| YW-190 | MC9(D-Y147, NMeL149, D-S151, D-A154, Tic155, NH2) Ser-NH2 | (D-Tyr)-Phe-(NMe-Leu)-Pro-(D-Ser)-Gln-Phe-(D-Ala)-(D-Tic)- | 40 |
| YW-192 | MC9(DiMe-D-Y147, NMeL149, D-S151, D-A154, Tic155) | DiMe-(D-Tyr)-Phe-(NMe-Leu)-Pro-(D-Ser)-Gln-Phe-(D-Ala)-Tic-Ser | 41 |
| YW-193 | MC9(hexanoyl, D-Y147, NMeL149, D-S151, D-A154, Tic155) | Hexanoyl-(D-Tyr)-Phe-(NMe-Leu)-Pro-(D-Ser)-Gln-Phe-(D-Ala)-Tic-Ser | 42 |
| YW-194 | MC9(2-cyclohexyl acetyl, D-Y147, NMeL149, D-S151, D-A154, Tic155) | (2-Cyclohexylacetyl)-(D-Tyr)-Phe-(NMe-Leu)-Pro-(D-Ser)-Gln-Phe-(D-Ala)-Tic-Ser | 43 |
| YW-195 | MC9(4-(trifluoromethyl)benzoyl, D-Y147, NMeL149, D-S151 D-A154, Tic155) | 4-(TrifluoromethyObenzoyl-(D-Tyr)-Phe-(NMe-Leu)-Pro-(D-Ser)-Gln-Phe-(D-Ala)-Tic-Ser | 44 |
| YW-198 | MC9(D-Y147, NMeL149, Hyp150, D-S151, D-A154, Tic155) | (D-Tyr)-Phe-(NMe-Leu)-Hyp-(D-Ser)-Gln-Phe-(D-Ala)-Tic-Ser | 45 |
| YW-199 | MC9(D-Y147, 1Nal148, NMeL149, D-S151, D-A154, Tic155) | (D-Tyr)-1Nal-(NMe-Leu)-Pro-(D-Ser)-Gln-Phe-(D-Ala)-Tic-Ser | 46 |
| YW-200 | NMeL149, D-S151, Tic155) | MC9(D-Y147, 2Nal148, (D-Tyr)-2Nal-(NMe-Leu)-Pro-(D-Ser)-Gln-Phe-(D-Ala)-Tic-Ser | 47 |
| YW-201 | MC9(D-Y147, Bpa148, NMeL149, D-S151, D-A154, Tic155) | (D-Tyr)-Bpa-(NMe-Leu)-Pro-(D-Ser)-Gln-Phe-(D-Ala)-Tic-Ser | 48 |
| YW-202 | MC9(D-Y147, F(4-Me)148, NMeL149, D-S151, D-A154, Tic155) | (D-Tyr)-Phe(4-Me)-(NMe-Leu)-Pro-(D-Ser)-Gln-Phe-(D-Ala)-Tic-Ser | 49 |
| YW-203 | MC9(D-Y147, F(4-Cl)148, NMeL149, D-S151, D-A154, Tic155) | (D-Tyr)-Phe(4-Cl)-(NMe-Leu)-Pro-(D-Ser)-Gln-Phe-(D-Ala)-Tic-Ser | 50 |
| YW-204 | MC9(D-Y147, NMeL149, D-T151, D-A154, Tic155) | (D-Tyr)-Phe-(NMe-Leu)-Pro-(D-Thr)-Gln-Phe-(D-Ala)-Tic-Ser | 51 |
| YW-205 | MC9(D-Y147, NMeL149, D-S151, D-A154, F(4-Me)155) | (D-Tyr)-Phe-(NMe-Leu)-Pro-(D-Ser)-Gln-Phe-(D-Ala)-Phe(4-Me)-Ser | 52 |
| YW-206 | MC9(D-Y147, NMeL149, D-S151, D-A154, F(4-Cl)155) | (D-Tyr)-Phe-(NMe-Leu)-Pro-(D-Ser)-Gln-Phe-(D-Ala)-Phe(4-Cl)-Ser | 53 |

-continued

| Peptide No. | | Sequence | SEQ ID NO: |
|---|---|---|---|
| YW-207 | MC9(D-Y147, NMeL149, D-S151, D-A154, Tic155) | 3-phenylpropyl-(D-Tyr)-Phe-(NMe-Leu)-Pro-(D-Ser)-Gln-Phe-(D-Ala)-Tic-Ser | 54 |
| YW-210 | MC9(D-Y147, NMeL149, Pro(4Ph)150, D-S151, 2Nal153, D-A154, Tic155) | (D-Tyr)-Phe-(NMe-Leu)-Pro(4Ph)-(D-Ser)-Gln-2Nal-(D-Ala)-Tic-Ser | 55 |
| YW-215 | MC9(D-Y147, NMeL149, Pro(4Ph)150, D-S151, D-A154, Tic155) | (D-Tyr)-Phe-NMeLeu-Pro(4Ph)-(D-Ser)-Gln-Phe-(D-Ala)-Tic-Ser | 56 |
| YW-216 | MC9(D-NMeY147, NMeL149, Pro(4Ph)150, D-S151, D-A154, Tic155) | (D-NMe-Tyr)-Phe-NMeLeu-Pro(4Ph)-(D-Ser)-Gln-2Nal-(D-Ala)-Tic-Ser | 57 |
| YW-217 | MC9(D-NMeY147, NMeL149, Pro(4Ph)150, D-S151, D-A154, Tic155) | Palm-PEG8-βAla-βAla-(D-NMe-Tyr)-Phe-(NMe-Leu)-Pro(4Ph)-(D-Ser)-Gln-2Nal-(D-Ala)-Tic-Ser | 58 |
| YW-219 | MC9(D-Y147, NMeL149, Pro(4Ph)150, D-S151, 2Nal153, D-A154, Tic155) | (D-Tyr)-Phe-(NMe-Leu)-Pro(4Ph)-(D-Ser)-Gln-2Nal-(D-Ala)-Tic-Ser | 59 |
| YW-220 | MC9(D-NMeY147, NMeL149, Pro(4Ph)150, D-S151, 2Nal153, D-A154, Tic155, NMeS156) | (D-NMeTyr)-Phe-NMeLeu-Pro(4Ph)-(D-Ser)-Gln-2Nal-(D-Ala)-Tic-(NMe-Ser) | 60 |
| YW-221 | MC9(DY(3F)147, NMeL149, Pro(4Ph)150, D-S151, 2Nal153, D-A154, Tic155, NMeS156) | [D-Tyr(3F)]-Phe-(NMe-Leu)-Pro(4Ph)-(D-Ser)-Gln-2Nal-(D-Ala)-Tic-(NMe-Ser) | 61 |
| YW-222 | MC9(DY(3F)147, NMeL149, Pro(4Ph)150, D-S151, 2Nal153, D-A154, Tic155) | [D-Tyr(3F)]-Phe-(NMe-Leu)-Pro(4Ph)-(D-Ser)-Gln-2Nal-(D-Ala)-TicSer | 62 |
| YW-223 | MC9(Palm-PEG, Gly145, Gly146, DY147, NMeL149, Pro(4Ph)150, D-S151, 2Nal153, D-A154, Tic155) | Palm-PEG-Gly-Gly-(D-Tyr)-Phe-NMeLeu-Pro(4Ph)-(D-Ser)-Gln-2Nal-(D-Ala)-Tic-Ser | 63 |
| YW-224 | MC9(DY147, NMeL149, Pro(diF)150, D-S151, 2Nal153, D-A154, Tic155, NMeS156) | (D-Tyr)-Phe-(NMe-Leu)-Pro(diF)-(D-Ser)-Gln-2Nal-(D-Ala)-Tic-NMeSer | 64 |
| YW-225 | MC9(DNMeY147, NMeL149, Pro(diF)150, D-S151, 2Nal153, D-A154, Tic155, NMeS156) | (D-NMeTyr)-Phe-NMeLeu-Pro(diF)-(D-Ser)-Gln-2Nal-(D-Ala)-Tic-(NMe-Ser) | 65 |
| YW-226 | MC9(DY(3F)147, NMeL149, Pro(diF)150, D-S151, 2Nal153, D-A154, Tic155, NMeS156) | [D-Tyr(3F)]-Phe-NMeLeu-Pro(diF)-(D-Ser)-Gln-2Nal-(D-Ala)-Tic-(NMe-Ser) | 66 |

The present disclosure also provides a use of the above-mentioned Compound I, the pharmaceutically acceptable salt thereof, the tautomer thereof, the crystal form thereof, the solvate thereof or the prodrug thereof in manufacturing a medicament, the medicament is for treating and/or preventing a disease associated with ChemR23.

The "disease associated with ChemR23" include, but is not limited to, for example, immune disease, inflammatory disease, metabolic disease (such as obesity or diabetes), cardiovascular disease, bone disease, tumor (such as cancer), reproductive system disease, mental disease, viral infection, asthma or liver disease.

The present disclosure also provides a use of the above-mentioned Compound I, the pharmaceutically acceptable salt thereof, the tautomer thereof, the crystal form thereof, the solvate thereof or the prodrug thereof in manufacturing a ChemR23 agonist.

The present disclosure also provides a pharmaceutical composition comprising the above-mentioned Compound I, the pharmaceutically acceptable salt thereof, the tautomer thereof, the crystal form thereof, the solvate thereof or the prodrug thereof, and a pharmaceutically acceptable excipient.

The pharmaceutically acceptable excipients can be those widely used in drug manufacture field. The excipient is mainly used to provide a safe, stable and functionalized pharmaceutical composition, and can also provide a method which makes the active ingredients dissolved at a desired rate after the subject receives administration or promotes the efficacy of absorption of the active ingredients after the subject is administered with the composition. The excipient can be an inert filler, or provide a certain function, such as stabilizing the overall pH value of the composition or preventing the degradation of the active ingredients of the composition. The pharmaceutically acceptable excipient may comprise the excipients selected from the group consisting of: binder, suspending agent, emulsifier, diluent, filler, granulating agent, adhesive, disintegrating agent, lubricant, anti-adhesive agent, glidant, wetting agent, gelling agent, absorption retarder, dissolution inhibitor, reinforcing agent, adsorbent, buffer, chelating agent, preservative, colorant, flavoring agent and sweetening agent.

The pharmaceutical composition of the present disclosure can be prepared according to the disclosure using any method known to those skilled in the art, such as conventional mixing, dissolving, granulating, emulsifying, grinding, encapsulating, embedding or lyophilization.

The pharmaceutical composition of the present disclosure can be formulated into any form for administration, including injection (intravenous), mucosal, oral administration (solid and liquid preparation), inhalation, ocular administration, rectal administration, topical or parenteral (infusion, injection, implantation, subcutaneous, vein, artery, intramuscular) administration. The pharmaceutical composition of the present disclosure can also be a controlled release or delayed release preparation (e.g., liposome or microsphere). Examples of solid oral preparations include but not limited to powder, capsule, caplet, soft capsule and tablet. Examples of liquid preparations for oral or mucosal administration include but not limited to suspension, emulsion, elixir and solution. Examples of preparations for topical administration include but not limited to emulsion, gel, ointment, cream, patch, paste, foam, lotion, drops or serum preparation. Examples of preparations for parenteral administration include but not limited to injection solution, dry preparation which can be dissolved or suspended in a pharmaceutically acceptable carrier, injection suspension and injection emulsion. Examples of other suitable preparations of the pharmaceutical composition, include but not limited to eye drops and other ophthalmic preparations; aerosol, such as nasal spray or inhalation; liquid dosage forms suitable for parenteral administration; suppository and pastille.

The present disclosure provides a peptide compound of formula II, a pharmaceutically acceptable salt thereof, a tautomer thereof, a solvate thereof, a crystal form thereof or a prodrug thereof; the Compound II is selected from the group consisting of

| Peptide No. | | Sequence | SEQ ID NO: |
|---|---|---|---|
| YW-96 | MC9(D-Tyr147, S-Pip150, D-S151, D-A154, Tic155) | (D-Tyr)-Phe-Leu-(S-Pip)-(D-Ser)-Gln-Phe-(D-Ala)-Tic-Ser | 67 |
| YW-97 | MC9(D-F147, D-S151, D-A154, Tic155) | (D-Phe)-Phe-Leu-Pro-(D-Ser)-Gln-Phe-(D-Ala)-Tic-Ser | 68 |
| YW-103 | MC9(D-NMeY147, D-S151, D-A154, Tic155) | (D-NMe-Tyr)-Phe-Leu-Pro-(D-Ser)-Gln-Phe-(D-Ala)-Tic-Ser | 69 |
| YW-104 | MC9(D-Y147, NMeF148, D-S151, D-A154, Tic155) | (D-Tyr)-(NMe-Phe)-Leu-Pro-(D-Ser)-Gln-Phe-(D-Ala)-Tic-Ser | 70 |
| YW-110 | MC9(D-Y147, D-S151, D-A154, Tic155, NMeS156) | (D-Tyr)-Phe-Leu-Pro-(D-Ser)-Gln-Phe-(D-Ala)-Tic-(NMe-Ser) | 71 |
| YW-112 | MC9(D-Y147, Pro(5Ph)150, D-S151, D-A154, Tic155) | (D-Tyr)-Phe-Leu-Pro(5-phenyl)-(D-Ser)-Gln-Phe-(D-Ala)-Tic-Ser | 72 |
| YW-113 | MC9(D-Y147, Pro(4Ph)150, D-S151, D-A154, Tic155) | (D-Tyr)-Phe-Leu-Pro(4-phenyl)-(D-Ser)-Gln-Phe-(D-Ala)-Tic-Ser | 73 |
| YW-114 | MC9(D-Y147, Thz150, D-S151, D-A154, Tic155) | (D-Tyr)-Phe-Leu-Thz-(D-Ser)-Gln-Phe-(D-Ala)-Tic-Ser | 74 |
| YW-115 | MC9(D-Y147, Aze150, D-S151, D-A154, Tic155) | (D-Tyr)-Phe-Leu-Aze-(D-Ser)-Gln-Phe-(D-Ala)-Tic-Ser | 75 |
| YW-117 | MC9(D-Y147, D-S151, 1Nal153, D-A154, Tic155) | (D-Tyr)-Phe-Leu-Pro-(D-Ser)-Gln-1Nal-(D-Ala)-Tic-Ser | 76 |
| YW-118 | MC9(D-Y147, D-S151, 2Nal153, D-A154, Tic155) | (D-Tyr)-Phe-Leu-Pro-(D-Ser)-Gln-2Nal-(D-Ala)-Tic-Ser | 77 |
| YW-119 | MC9(D-Y147, D-S151, Bpa153, D-A154, Tic155) | (D-Tyr)-Phe-Leu-Pro-(D-Ser)-Gln-Bpa-(D-Ala)-Tic-Ser | 78 |
| YW-149 | MC9(D-Y147, D-S151, D-A154, D-Tic155) | (D-Tyr)-Phe-Leu-Pro-(D-Ser)-Gln-Phe-(D-Ala)-(D-Tic)-Ser | 79 |
| YW-150 | MC9(D-Y147, D-S151, D-A154, Tilc155) | (D-Tyr)-Phe-Leu-Pro-(D-Ser)-Gln-Phe-(D-Ala)-Tilc-Ser | 80 |
| YW-151 | MC9(D-Y147, D-S151, D-A154, D-Tilc155) | (D-Tyr)-Phe-Leu-Pro-(D-Ser)-Gln-Phe-(D-Ala)-(D-Tilc)-Ser | 81 |

-continued

| Peptide No. | | Sequence | SEQ ID NO: |
|---|---|---|---|
| YW-154 | MC9(D-NMeY147, D-S151, D-A154, D-Tilc155) | (D-NMe-Tyr)-Phe-Leu-Pro-(D-Ser)-Gln-Phe-(D-Ala)-(D-Ti lc)-Ser | 82 |
| YW-158 | MC9(D-Y147, D-S151, D-A154, TP5C155) | (D-Tyr)-Phe-Leu-Pro-(D-Ser)-Gln-Phe-(D-Ala)-TP5C-Ser | 83 |
| YW-159 | MC9(D-Y147, D-S151, D-A154, TP6C155) | (D-Tyr)-Phe-Leu-Pro-(D-Ser)-Gln-Phe-(D-Ala)-TP6C-Ser | 84 |
| YW-189 | MC9(D-Y147, D-S151, D-A154, Tic155, NH2) | (D-Tyr)-Phe-Leu-Pro-(D-Ser)-Gln-Phe-(D-Ala)-Tic-Ser-NH2 | 85 |
| YW-196 | MC9(D-Y147, Nval49, D-S151, D-A154, Tic155) | (D-Tyr)-Phe-Nva-Pro-(D-Ser)-Gln-Phe-(D-Ala)-Tic-Ser | 86 |
| YW-197 | MC9(D-Y147, Nle149, D-S151, D-A154, Tic155) | (D-Tyr)-Phe-Nle-Pro-(D-Ser)-Gln-Phe-(D-Ala)-Tic-Ser | 87 |

The present disclosure also provides a use of the above-mentioned Compound II, the pharmaceutically acceptable salt thereof, the tautomer thereof, the crystal form thereof, the solvate thereof or the prodrug thereof in manufacturing a medicament, the medicament is for treating and/or preventing a disease associated with ChemR23.

The "disease associated with ChemR23" include, but is not limited to, for example, immune disease, inflammatory disease, metabolic disease (such as obesity or diabetes), cardiovascular disease, bone disease, tumor (such as cancer), reproductive system disease, mental disease, viral infection, asthma or liver disease.

The present disclosure also provides a use of the above-mentioned Compound II, the pharmaceutically acceptable salt thereof, the tautomer thereof, the crystal form thereof, the solvate thereof or the prodrug thereof in manufacturing a ChemR23 agonist.

The present disclosure also provides a pharmaceutical composition comprising the above-mentioned Compound II, the pharmaceutically acceptable salt thereof, the tautomer thereof, the crystal form thereof, the solvate thereof or the prodrug thereof, and a pharmaceutically acceptable excipient.

The pharmaceutically acceptable excipients can be those widely used in drug manufacture field. The excipient is mainly used to provide a safe, stable and functionalized pharmaceutical composition, and can also provide a method which makes the active ingredients dissolved at a desired rate after the subject receives administration or promotes the efficacy of absorption of the active ingredients after the subject is administered with the composition. The excipient can be an inert filler, or provide a certain function, such as stabilizing the overall pH value of the composition or preventing the degradation of the active ingredients of the composition. The pharmaceutically acceptable excipient may comprise the excipients selected from the group consisting of: binder, suspending agent, emulsifier, diluent, filler, granulating agent, adhesive, disintegrating agent, lubricant, anti-adhesive agent, glidant, wetting agent, gelling agent, absorption retarder, dissolution inhibitor, reinforcing agent, adsorbent, buffer, chelating agent, preservative, colorant, flavoring agent and sweetening agent.

The pharmaceutical composition of the present disclosure can be prepared according to the disclosure using any method known to those skilled in the art, such as conventional mixing, dissolving, granulating, emulsifying, grinding, encapsulating, embedding or lyophilization.

The pharmaceutical composition of the present disclosure can be formulated into any form for administration, including injection (intravenous), mucosal, oral administration (solid and liquid preparation), inhalation, ocular administration, rectal administration, topical or parenteral (infusion, injection, implantation, subcutaneous, vein, artery, intramuscular) administration. The pharmaceutical composition of the present disclosure can also be a controlled release or delayed release preparation (e.g., liposome or microsphere). Examples of solid oral preparations include but not limited to powder, capsule, caplet, soft capsule and tablet. Examples of liquid preparations for oral or mucosal administration include but not limited to suspension, emulsion, elixir and solution. Examples of preparations for topical administration include but not limited to emulsion, gel, ointment, cream, patch, paste, foam, lotion, drops or serum preparation. Examples of preparations for parenteral administration include but not limited to injection solution, dry preparation which can be dissolved or suspended in a pharmaceutically acceptable carrier, injection suspension and injection emulsion. Examples of other suitable preparations of the pharmaceutical composition, include but not limited to eye drops and other ophthalmic preparations; aerosol, such as nasal spray or inhalation; liquid dosage forms suitable for parenteral administration; suppository and pastille.

The present disclosure provides a peptide compound of formula III, a pharmaceutically acceptable salt thereof, a tautomer thereof, a solvate thereof, a crystal form thereof or a prodrug thereof:

XX0-XX1-XX2-XX3-XX4-XX5-XX6-XX7-XX8-XX9-XX10-P   (III)

wherein, XX0 is $R^{0-2}$,

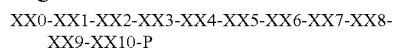

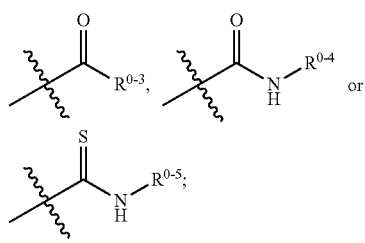

$R^{0-2}$ is a $C_1$-$C_6$ alkyl substituted or unsubstituted by $R^{0-2-1}$ (the number of $R^{0-2-1}$ can be one or more than one {e.g., 1, 2, 3, 4 or 5}; when a plurality of $R^{0-2-1}$ are present, they are the same or different; each $R^{0-2-1}$ can be independently at the terminal or nonterminal site of the $C_1$-$C_6$ alkyl; the $C_1$-$C_6$ alkyl can be a $C_1$-$C_4$ alkyl; the $C_1$-$C_4$ alkyl can be methyl, ethyl, n-propyl, isopropyl, n-butyl, isobutyl, sec-butyl or tert-butyl; the "$C_1$-$C_6$ alkyl substituted by $R^{0-2-1}$" is, for example, 3,5-dihydroxybenzyl or 3-phenylpropyl);

each $R^{0-2-1}$ is independently phenyl substituted or unsubstituted by hydroxyl (the number of the hydroxyl can be one or more than one {e.g., 1, 2, 3, 4 or 5}; each hydroxyl can be independently in ortho, meta or para position of the phenyl; the "phenyl substituted by hydroxyl" is, for example, 3,5-dihydroxyphenyl);

$R^{0-3}$ is a $C_1$-$C_8$ alkyl substituted or unsubstituted by $R^{0-3-1}$ (the number of $R^{0-3-1}$ can be one or more than one {e.g., 1, 2, 3, 4 or 5}; when a plurality of $R^{0-3-1}$ are present, they are the same or different; each $R^{0-3-1}$ can be independently at the terminal or nonterminal site of the $C_1$-$C_8$ alkyl; the $C_1$-$C_8$ alkyl can be a $C_1$-$C_4$ alkyl or n-pentyl; the $C_1$-$C_4$ alkyl can be methyl, ethyl, n-propyl, isopropyl, n-butyl, isobutyl, sec-butyl or tert-butyl; the "$C_1$-$C_8$ alkyl substituted by $R^{0-3-1}$" is, for example, 2-phenylethyl, 3-phenylpropyl, 4-phenylbutyl, 4-phenylbenzyl, diphenylmethyl, 3,4-dihydroxybenzyl, 3,5-dihydroxybenzyl, biphenyl-4-ylmethyl or cyclohexylmethyl), or a phenyl substituted or unsubstituted by $R^{0-3-2}$ (the number of $R^{0-3-2}$ can be one or more than one {e.g., 1, 2, 3, 4 or 5}; when a plurality of $R^{0-3-2}$ are present, they are the same or different; each $R^{0-3-2}$ can be independently in the ortho, meta or para position of the phenyl; the "phenyl substituted by $R^{0-3-2}$" is, for example, 3,5-dihydroxyphenyl, 2,3-dihydroxyphenyl, 2,6-dihydroxyphenyl, 2,3,4-trihydroxyphenyl, 2,3,5-trihydroxyphenyl or 4-trifluoromethylphenyl);

each $R^{0-3-1}$ is independently phenyl substituted or unsubstituted by hydroxyl (the number of the hydroxyl can be one or more than one {e.g., 1, 2, 3, 4 or 5}; each hydroxyl can be independently in ortho, meta or para position of the phenyl; the "phenyl substituted by hydroxyl" is, for example, 3,4-dihydroxyphenyl or 3,5-dihydroxyphenyl), a biphenyl, or a $C_3$-$C_6$ cycloalkyl (e.g., cyclohexyl);

each $R^{0-3-2}$ is independently hydroxyl or a $C_1$-$C_4$ alkyl substituted by halogen (the number of the "halogen" can be one or more than one{e.g., 1, 2, 3, 4 or 5}; each "halogen" can be independently fluorine, chlorine or bromine; when a plurality of halogens are present, they are the same or different; the $C_1$-$C_4$ alkyl can be methyl, ethyl, n-propyl, isopropyl, n-butyl, isobutyl, sec-butyl or tert-butyl; the "$C_1$-$C_4$ alkyl substituted by halogen" is, for example, trifluoromethyl);

$R^{0-4}$ is a $C_1$-$C_8$ alkyl substituted or unsubstituted by $R^{0-4-1}$ (the number of $R^{0-4-1}$ can be one or more than one {e.g., 1, 2, 3, 4 or 5}; when a plurality of $R^{0-4-1}$ are present, they are the same or different; each $R^{0-4-1}$ can be independently at the terminal or nonterminal site of the $C_1$-$C_8$ alkyl; the $C_1$-$C_8$ alkyl can be a $C_1$-$C_4$ alkyl or n-pentyl; the $C_1$-$C_4$ alkyl can be methyl, ethyl, n-propyl, isopropyl, n-butyl, isobutyl, sec-butyl or tert-butyl; the "$C_1$-$C_8$ alkyl substituted by $R^{0-4-1}$" is, for example, 2-phenylethyl, 3-phenylpropyl, 4-phenylbutyl, 4-phenylbenzyl, diphenylmethyl, 3,4-dihydroxybenzyl, 3,5-dihydroxybenzyl or cyclohexylmethyl);

each $R^{0-4-1}$ is independently phenyl substituted or unsubstituted by hydroxyl (the number of the hydroxyl can be one or more than one {e.g., 1, 2, 3, 4 or 5}; each hydroxyl can be independently in ortho, meta or para position of the phenyl; the "phenyl substituted by hydroxyl" is, for example, 3,4-dihydroxyphenyl or 3,5-dihydroxyphenyl), or a $C_3$-$C_6$ cycloalkyl (e.g., cyclohexyl);

$R^{0-5}$ is a $C_1$-$C_8$ alkyl substituted or unsubstituted by $R^{0-5-1}$ (the number of $R^{0-5-1}$ can be one or more than one {e.g., 1, 2, 3, 4 or 5}; when a plurality of $R^{0-5-1}$ are present, they are the same or different; each $R^{0-5-1}$ can be independently at the terminal or nonterminal site of the $C_1$-$C_8$ alkyl; the $C_1$-$C_8$ alkyl can be a $C_1$-$C_4$ alkyl or n-pentyl; the $C_1$-$C_4$ alkyl can be methyl, ethyl, n-propyl, isopropyl, n-butyl, isobutyl, sec-butyl or tert-butyl; the "$C_1$-$C_8$ alkyl substituted by $R^{0-5-1}$" is, for example, 2-phenylethyl, 3-phenylpropyl, 4-phenylbutyl, 4-phenylbenzyl, diphenylmethyl, 3,4-dihydroxybenzyl, 3,5-dihydroxybenzyl or cyclohexylmethyl);

each $R^{0-5-1}$ is independently phenyl substituted or unsubstituted by hydroxyl (the number of the hydroxyl can be one or more than one {e.g., 1, 2, 3, 4 or 5}; each hydroxyl can be independently in ortho, meta or para position of the phenyl; the "phenyl substituted by hydroxyl" is, for example, 3,4-dihydroxyphenyl or 3,5-dihydroxyphenyl), or a $C_3$-$C_6$ cycloalkyl (e.g., cyclohexyl);

XX1 is D-Tyr, of which the amino group is substituted or unsubstituted by one $C_1$-$C_4$ alkyl (e.g., methyl, ethyl, n-propyl, isopropyl, n-butyl, isobutyl, sec-butyl or tert-butyl, also e.g., methyl) (the "substituted amino acid" is, for example, D-NMeTyr);

XX2 is an amino acid selected from the group consisting of

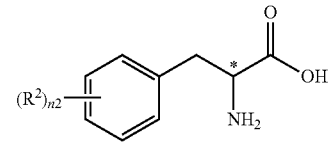

{e.g., Phe, Phe(4-Cl) or Phe(4-Me)}; n2 is 0 or 1, $R^2$ is a $C_1$-$C_4$ alkyl (e.g., methyl, ethyl, n-propyl, isopropyl, n-butyl or isobutyl) or halogen (e.g., fluorine or chlorine), "*" labeled carbon atom is a chiral carbon atom, which is in R-configuration or S-configuration ($R^2$ can be in the ortho, meta or para position of the phenyl, for example, when n2 is 1, $R^2$ can be in the para position of the phenyl; also e.g.,

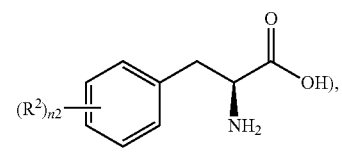

of which the amino group is substituted or unsubstituted by one $C_1$-$C_4$ alkyl (e.g., methyl, ethyl, n-propyl, isopropyl, n-butyl, isobutyl, sec-butyl or tert-butyl) (the "substituted amino acid" is, for example, NMePhe);

XX3 is

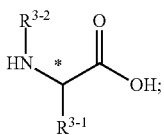

wherein, "*" labeled carbon atom is a chiral carbon atom, which is in R-configuration or S-configuration (e.g.,

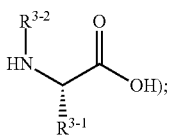

$R^{3-1}$ is a $C_4$-$C_5$ alkyl (e.g., n-butyl, isobutyl, sec-butyl, tert-butyl, n-pentyl or 3-methylbutyl) or benzyl; $R^{3'}$ is hydrogen or a $C_1$-$C_4$ alkyl (e.g., methyl, ethyl, n-propyl, isopropyl, n-butyl, isobutyl, sec-butyl or tert-butyl); (the

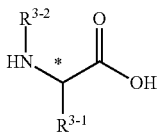

is, for example, Leu, NMe-Leu, NMe-Phe, NMe-Ho-Leu, NEt-Leu, NPr-Leu, NiPr-Leu, Nbu-Leu, NMe-Nle or NMe-Ile);

XX4 is

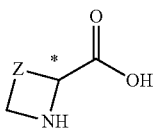

(e.g.,

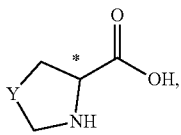

Y is $—(CR^{4-1}R^{4-2})—$ {e.g., $—CH_2—$, $—CH(OH)—$ or $—CF_2$}, $—(CH_2)_2—$ or $—S—$; also e.g., Aze, Thz, Hyp, Pro, Pro(5Ph), Pro(4Ph), Pro(diF) or HoPro); "*" labeled carbon atom is a chiral carbon atom, which is in R-configuration or S-configuration (e.g.,

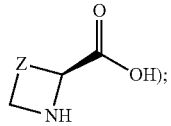

Z is $—(CR^{4-1}R^{4-2})_{n4}—$ {e.g., $—CH_2—$, $—(CH_2)_2—$, $—CH(OH)—CH_2—$, $—CF_2—CH_2—$, $—CHPh—CH_2—$, $—CH_2—CHPh—$ or $—(CH_2)_3—$} or $—S—(CR^{4-3}R^{4-4})_{n4'}—$ {e.g., $—S—CH_2—$}; the right terminal sites of the $—(CR^{4-1}R^{4-2})_{n4}—$ and the $—S—(CR^{4-3}R^{4-4})_{n4'}—$ are linked to the chiral carbon atom; n4 is 1-3 (e.g., 1, 2 or 3), n4' is 1 or 2; each of $R^{4-1}$, $R^{4-2}$, $R^{4-3}$, and $R^{4-4}$ is independently hydrogen, hydroxyl, halogen (e.g., fluorine or chlorine) or phenyl;

XX5 is D-Ser;
XX6 is Gln;
XX7 is

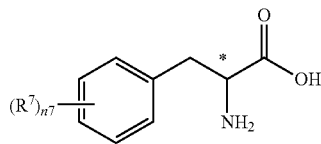

{e.g., Phe, Phe(3-Cl), Phe(3-Me), Phe(3-OMe), Phe(4-OMe), Phe(4-Me) or Phe(4-Cl)}; n7 is 0 or 1, $R^7$ is a $C_1$-$C_4$ alkyl (e.g., methyl, ethyl, n-propyl, isopropyl, n-butyl or isobutyl), a $C_1$-$C_4$ alkoxy (e.g., methoxy, ethoxy, n-propoxy, isopropoxy, n-butoxy or isobutoxy) or halogen (e.g., fluorine or chlorine), "*" labeled carbon atom is a chiral carbon atom, which is in R-configuration or S-configuration ($R^7$ can be in the ortho, meta or para position of the phenyl, for example, when n7 is 1, $R^7$ can be in the para position of the phenyl; also e.g.,

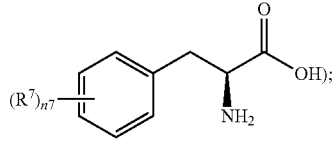

XX8 is D-Ala;
XX9 is Tic;
XX10 is Ser, of which the amino group is substituted or unsubstituted by one $C_1$-$C_4$ alkyl (e.g., methyl, ethyl, n-propyl, isopropyl, n-butyl, isobutyl, sec-butyl or tert-butyl) (the "substituted amino acid" is, for example, NMe-Ser);
P is hydroxyl or amino group.

In one embodiment, Compound III can be selected from the group consisting of

| Peptide No. | | Sequence | SEQ ID NO: |
|---|---|---|---|
| YW-71 | MC9(3PPA, D-Y147, D-S151, D-A154, Tic155) | (3-Phenylpropanoyl)-(D-Tyr)-Phe-Leu-Pro-(D-Ser)-Gln-Phe-(D-Ala)-Tic-Ser | 88 |

-continued

| Peptide No. | | Sequence | SEQ ID NO: |
|---|---|---|---|
| YW-72 | MC9[phenethylcarbamoyl-D-Y147, D-S151, D-A154, Tic155] | (Phenethylcarbamoyl)-(D-Tyr)-Phe-Leu-Pro-(D-Ser)-Gln-Phe-(D-Ala)-Tic-Ser | 89 |
| YW-73 | MC9[phenethylcarbamothioyl-D-Y147, D-S151, D-A154, Tic155] | (Phenethylcarbamothioyl)-(D-Tyr)-Phe-Leu-Pro-(D-Ser)-Gln-Phe-(D-Ala)-Tic-Ser | 90 |
| YW-74 | MC9(3-phenylpropyl-D-Y147, D-S151, D-A154, Tic155) | 3-Phenylpropyl-(D-Tyr)-Phe-Leu-Pro-(D-Ser)-Gln-Phe-(D-Ala)-Tic-Ser | 91 |
| YW-75 | MC9(4PhBA, D-Y147, D-S151, D-A154, Tic155) | (4-Phenylbutanoyl)-(D-Tyr)-Phe-Leu-Pro-(D-Ser)-Gln-Phe-(D-Ala)-Tic-Ser | 92 |
| YW-76 | MC9(5PhVA, D-Y147, D-S151, D-A154, Tic155) | (5-Phenylpentanoyl)-(D-Tyr)-Phe-Leu-Pro-(D-Ser)-Gln-Phe-(D-Ala)-Tic-Ser | 93 |
| YW-77 | MC9(4BPhAA, D-Y147, D-S151, D-A154, Tic155) | (4-Biphenylacetyl)-(D-Tyr)-Phe-Leu-Pro-(D-Ser)-Gln-Phe-(D-Ala)-Tic-Ser | 94 |
| YW-78 | MC9(DPhAA, D-Y147, D-S151, D-A154, Tic155) | (Diphenylacetyl)-(D-Tyr)-Phe-Leu-Pro-(D-Ser)-Gln-Phe-(D-Ala)-Tic-Ser | 95 |
| YW-79 | MC9(35HBA, D-Y147, D-S151, D-A154, Tic155) | (3,5-Dihydroxybenzoyl)-(D-Tyr)-Phe-Leu-Pro-(D-Ser)-Gln-Phe-(D-Ala)-Tic-Ser | 96 |
| YW-127 | MC9(23HBA, D-Y147, D-S151, D-A154, Tic155) | 2,3-Dihydroxybenzoyl-(D-Tyr)-Phe-Leu-Pro-(D-Ser)-Gln-Phe-(D-Ala)-Tic-Ser | 97 |
| YW-128 | MC9(26HBA, D-Y147, D-S151, D-A154, Tic155) | 2,6-Dihydroxybenzoyl-(D-Tyr)-Phe-Leu-Pro-(D-Ser)-Gln-Phe-(D-Ala)-Tic-Ser | 98 |
| YW-129 | MC9(234HBA, D-Y147, D-S151, D-A154, Tic155) | 2,3,4-Trihydroxybenzoyl-(D-Tyr)-Phe-Leu-Pro-(D-Ser)-Gln-Phe-(D-Ala)-Tic-Ser | 99 |
| YW-131 | MC9(35HPA, D-Y147, D-S151, D-A154, Tic155) | 3,5-Dihydroxyphenylacetyl-(D-Tyr)-Phe-Leu-Pro-(D-Ser)-Gln-Phe-(D-Ala)-Tic-Ser | 100 |
| YW-132 | MC9(34HPA, D-Y147, D-S151, D-A154, Tic155) | 3,4-Dihydroxyphenylacetyl-(D-Tyr)-Phe-Leu-Pro-(D-ser)-Gln-Phe-(D-Ala)-Tic-Ser | 101 |

The present disclosure also provides a use of the above-mentioned Compound III, the pharmaceutically acceptable salt thereof, the tautomer thereof, the crystal form thereof, the solvate thereof or the prodrug thereof in manufacturing a medicament, the medicament is for treating and/or preventing a disease associated with ChemR23.

The "disease associated with ChemR23" include, but is not limited to, for example, immune disease, inflammatory disease, metabolic disease (such as obesity or diabetes), cardiovascular disease, bone disease, tumor (such as cancer), reproductive system disease, mental disease, viral infection, asthma or liver disease.

The present disclosure also provides a use of the above-mentioned Compound III, the pharmaceutically acceptable salt thereof, the tautomer thereof, the crystal form thereof, the solvate thereof or the prodrug thereof in manufacturing a ChemR23 agonist.

The present disclosure also provides a pharmaceutical composition comprising the above-mentioned Compound III, the pharmaceutically acceptable salt thereof, the tautomer thereof, the crystal form thereof, the solvate thereof or the prodrug thereof, and a pharmaceutically acceptable excipient.

The pharmaceutically acceptable excipients can be those widely used in drug manufacture field. The excipient is mainly used to provide a safe, stable and functionalized pharmaceutical composition, and can also provide a method which makes the active ingredients dissolved at a desired rate after the subject receives administration or promotes the efficacy of absorption of the active ingredients after the subject is administered with the composition. The excipient can be an inert filler, or provide a certain function, such as stabilizing the overall pH value of the composition or preventing the degradation of the active ingredients of the composition. The pharmaceutically acceptable excipient may comprise the excipients selected from the group consisting of: binder, suspending agent, emulsifier, diluent, filler, granulating agent, adhesive, disintegrating agent, lubricant, anti-adhesive agent, glidant, wetting agent, gelling agent, absorption retarder, dissolution inhibitor, reinforcing agent, adsorbent, buffer, chelating agent, preservative, colorant, flavoring agent and sweetening agent.

The pharmaceutical composition of the present disclosure can be prepared according to the disclosure using any method known to those skilled in the art, such as conventional mixing, dissolving, granulating, emulsifying, grinding, encapsulating, embedding or lyophilization.

The pharmaceutical composition of the present disclosure can be formulated into any form for administration, including injection (intravenous), mucosal, oral administration (solid and liquid preparation), inhalation, ocular administration, rectal administration, topical or parenteral (infusion, injection, implantation, subcutaneous, vein, artery, intramuscular) administration. The pharmaceutical composition of the present disclosure can also be a controlled release or delayed release preparation (e.g., liposome or microsphere). Examples of solid oral preparations include but not limited to powder, capsule, caplet, soft capsule and tablet. Examples of liquid preparations for oral or mucosal administration include but not limited to suspension, emulsion, elixir and solution. Examples of preparations for topical administration include but not limited to emulsion, gel, ointment, cream, patch, paste, foam, lotion, drops or serum preparation. Examples of preparations for parenteral administration include but not limited to injection solution, dry preparation which can be dissolved or suspended in a pharmaceutically acceptable carrier, injection suspension and injection emulsion. Examples of other suitable preparations of the pharmaceutical composition, include but not limited to eye drops and other ophthalmic preparations; aerosol, such as nasal spray or inhalation; liquid dosage forms suitable for parenteral administration; suppository and pastille.

The above preferred conditions can be arbitrarily combined without departing from the general knowledge in the art to obtain the preferred embodiments of the present disclosure.

The reagents and starting materials used in the present disclosure are commercially available.

Unless otherwise specified, the terms used in the present disclosure have the following meanings:

In the structural formula, when XX0 is hydrogen, $R^{0-2}$ or

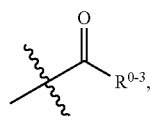

"XX0-XX1" refers to a group formed by the linking of XX0 and the amino group in XX1 (when multiple amino groups are present in one amino acid, it can be an amino group on a chiral carbon atom or a primary amino group), that is, an hydrogen atom in the amino group of XX1 is substituted by XX0. "The linking of

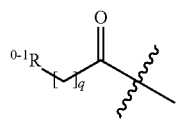

and PEG in XX0" is the same as above. For example, when XX0 is methyl and XX1 is Phe, "XX0-XX1" refers to

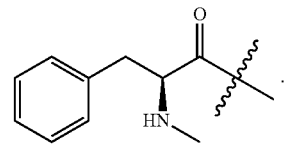 [SMILES: *C(=O)[C@H](Cc1ccccc1)NC]

In the structural formula, "XX1-XX2" refers to a group containing

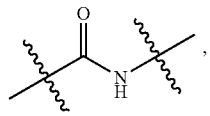 [SMILES: *NC(*)=O]

which is formed by linking of the carboxyl group in XX1 (when multiple carboxyl groups are present in one amino acid, it can be a carboxyl group on a chiral carbon atom) and the amino group in XX2 (when multiple amino groups are present in one amino acid, it can be an amino group on a chiral carbon atom or a primary amino group). "AA0-AA0", "AA0-XX1", "XX2-XX3", "XX3-XX4", "XX4-XX5", "XX5-XX6", "XX6-XX7", "XX7-XX8", "XX8"-XX9", "XX9-XX10" and "PEG-AA0" are the same as above. For example, when XX6 is Phe and XX7 is Gly, "XX6-XX7" refers to

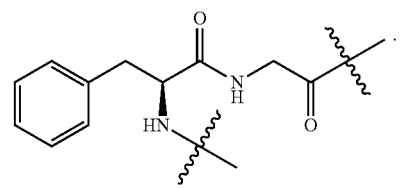 [SMILES: *N[C@@H](Cc1ccccc1)C(=O)NCC(*)=O]

In the structural formula, "XX10-P" refers to a group formed by the substitution of —OH in the carboxyl group (—COOH) in XX10 by P. For example, when XX10 is Phe and P is —NH$_2$, "XX10-P" refers to

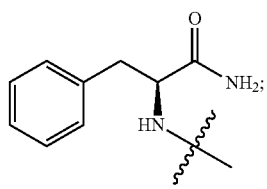 [SMILES: *N[C@@H](Cc1ccccc1)C(N)=O]

when XX10 is Phe and P is —OH, "XX10-P" refers to Phe itself

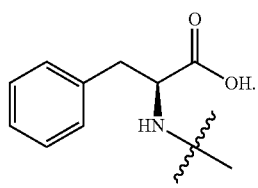 [SMILES: *N[C@@H](Cc1ccccc1)C(=O)O]

If the right end of the specific sequence ends with amino acid (XX10) and —P is not indicated, then P refers to —OH.

The conventional one-letter or three-letter codes for representing amino acids are used to define the peptide molecules of the present disclosure. The term "amino acid" includes water-soluble organic compounds having a carboxyl group (—COOH) and an amino group (—NH$_2$) attached to an α-carbon atom. The amino acid can be represented by the formula R—CH(NH$_2$)COOH. The R group is a hydrogen or an organic group, which determines the nature of any particular amino acids. When R is not a hydrogen, the tetrahedral arrangement of four different groups around the α-carbon atom renders the amino acid optically active. The two mirror images are referred to as the L-isomer and the D-isomer. Typically, only L-amino acids are the components of proteins (such as eukaryotic proteins).

Unless otherwise specified, the peptide molecule of the present disclosure comprises L-amino acid. When a D-amino acid is present in the peptide molecule of the present disclosure, it is represented by a conventional one-letter amino acid code with the prefix "(D)".

As described, the molecule of the present disclosure can comprise a peptide sequence having an "arbitrary D-amino acid" at a specific position or consist of a peptide sequence having an "arbitrary D-amino acid" at a specific position.

The "arbitrary D-amino acid" includes any natural or non-natural (e.g., chemically modified) D-amino acid at a specific position in the sequence. Examples of natural D-amino acids are as follows: D-alanine, D-aspartic acid, D-cysteine, D-glutamic acid, D-phenylalanine, D-glycine, D-histidine, D-isoleucine, D-lysine, D-leucine; D-methionine, D-asparagine, D-proline, D-glutamine, D-arginine, D-serine, D-threonine; D-valine, D-tryptophan, D-tyrosine. Examples of non-natural D-amino acids are as follows: naphthylalanine, D-pyridylalanine, D-tert-butylserine, D-ornithine, D-ε-aminolysine, D-homoarginine, D-α methyl leucine and the protons in these or other unnatural amino acids substituted by halogens (such as F).

By forming a peptide bond, the amino acids are combined to form a short chain (peptide) or a long chain (polypeptide). Proteins and/or peptides are known to consist of approximately 20 common amino acids with different flow ratios, the sequence of which determines the shape, properties and biological effects of the proteins and/or peptides. The amino acid residues in such peptides or polypeptide chains are usually represented by their arrangement on the chain, and the first position (i.e., position 1) is designated as the N-terminal amino acid of the chain.

TABLE 1

Explanation of amino acid abbreviations

| Abbreviation | Full name |
| --- | --- |
| Ala, A | Alanine |
| Cys, C | Cysteine |
| Asp, D | Aspartic acid |
| Glu, E | Glutamic acid |
| Phe, F | Phenylalanine |
| Gly, G | Glycine |
| His, H | Histidine |
| Ile, I | Isoleucine |
| NMeIle, NMe-Ile | N-methylisoleucine |
| Lys, K | Lysine |
| Leu, L | Leucine |
| Met, M | Methionine |
| Asn, N | Asparagine |
| Pro, P | Proline |
| Gln, Q | Glutamine |
| Arg, R | Arginine |
| Ser, S | Serine |
| Thr, T | Threonine |
| Val, V | Valine |
| Trp, W | Tryptophan |
| Tyr, Y | Tyrosine |
| D-Ala | D-alanine |
| D-Cys | D-cysteine |
| D-Asp | D-aspartic acid |
| D-Glu | D-glutamic acid |
| D-Phe | D-phenylalanine |
| D-Gly | D-glycine |
| D-His | D-histidine |
| D-Ile | D-isoleucine |
| D-Lys | D-lysine |
| D-Leu | D-leucine |
| D-Met | D-methionine |
| D-Asn | D-asparagine |
| D-Pro | D-proline |
| D-Gln | D-glutamine |
| D-Arg | D-arginine |
| D-Ser, DS | D-serine |
| D-Thr | D-threonine |
| D-Val | D-valine |
| D-Trp | D-tryptophan |
| D-Tyr, DY | D-tyrosine |
| D-Tyr(3F), DY(3F) | 3-fluoro-D-tyrosine |
| Ac | Acetyl |
| Tic | L-1,2,3,4-tetrahydroisoquinoline-3-carboxylic acid |
| Tic(6-Me) | L-6-methyl-1,2,3,4- |

TABLE 1-continued

Explanation of amino acid abbreviations

| Abbreviation | Full name |
|---|---|
| | tetrahydroisoquinoline-3-carboxylic acid |
| D-Tic | D-1,2,3,4-tetrahydroisoquinoline-3-carboxylic acid |
| BetaAla, Beta-Ala, betaA βAla | β-alanine |
| NMe-Phe, NMePhe, NMeF | N-methylphenylalanine |
| A6c | 1-Aminocyclohexylic acid |
| Ac-Lys | Acetyl lysine |
| Ahx | 6-Aminocaproic acid |
| Ala(dip) | 3,3-Diphenylalanine |
| Aze | (S)-azetidine-2-carboxylic acid |
| Bip | L-4,4'-biphenylalanine |
| Bpa | (4-Benzoyl)-phenylalanine |
| Cha | 3-Cyclohexylalanine |
| Chc | 1-Amino-cyclohexanecarboxylic acid |
| Cha | β- cyclohexyl-alanine |
| Hyp | Trans-4-hydroxyproline |
| Ica | 2,3-Dihydro-/H-isoindole-1-carboxylic acid |
| Idc | L-porphyrin-2-carboxylic acid |
| Lys(N3) | 6-Azido-leucine |
| MeA6c | 1-Aminomethyl-cyclohexylcarboxylic acid |
| 1Nal, Nal1, Nal-1, 1-Nal | 1-Naphthylalanine, |
| 2Nal, Nal2, Nal-2, 2-Nal | 2-Naphthylalanine, |
| Nle | Norleucine |
| Nva | Norvaline |
| Oic | L-octahydroindole-2-carboxylic acid |
| Palm | Palmitoyl |
| PEG8 | 1-Amino-3,6,9,12,15,18,21,24-octaoxa-heptacosanoic acid |
| Phe(4-Me), F(4-Me) | 4-Methylphenylalanine |
| Phe(4-Cl), F(4-Cl) | 4-Chlorophenylalanine |
| Phe(3-Me) | 3-Methylphenylalanine |
| Phe(3-Cl) | 3-Chlorophenylalanine |

TABLE 1-continued

Explanation of amino acid abbreviations

| Abbreviation | Full name |
| --- | --- |
| Phe(3-OMe) | 3-Methoxyphenylalanine |
| Phe(4-OMe) | 4-Methoxyphenylalanine |
| Phe(4-NO2) | 4-Nitrophenylalanine |
| Pra | Propargyl glycine |
| Pro(4Ph) | (2S,4S)-4-phenylproline |
| Pro(5Ph), Pro(5-Phenyl) | (2S,5R)-5-phenylpyrrolidine-2-carboxylic acid |
| Pro(diF), DiFluorPro | 4,4-Difluoroproline |
| Pro(4R-F) | Trans-4-fluoroproline |
| Thz | 4-Thioproline |
| Tic(OH) | 7-Hydroxy-(S)-1,2,3,4-tetrahydroisoquinoline-3-carboxylic acid |
| azaTic | 3,4-Dihydropyridazine-2(H)-formic acid |
| Ti1c | (S)-1,2,3,4-tetrahydroisoquinolinoline-1-carboxylic acid |
| D-Ti1c | (R)-1,2,3,4-tetrahydroisoquinolinoline-1-carboxylic acid |
| TP5C | (S)-4,5,6,7-tetrahydrothieno[2,3-c]pyridine-5-carboxylic acid |
| TP6C | (S)-4,5,6,7-tetrahydrothieno[2,3-c]pyridine-6-carboxylic acid |
| DiMe-DY, DiMe-(D-Tyr) | D-N,N-dimethyltyrosine |
| D-Oic | D-octahydroindole-2-carboxylic acid |
| D-Hyp | D-trans-4-hydroxyproline |
| D-Tyr(3F) | D-3-fluoro-tyrosine |
| NAsp | N-(carboxymethyl)glycine |
| D-NMeAla, D-NMeA, NMe-D-Ala, NMe-D-A | D-N-methylalanine |
| NMeGln, NMe-Gln | N-methylglutamine |
| NGln | N-(2-carbamoylethyl)glycine |
| NMeLeu, NMe-Leu, NMeL | N-methylleucine |
| NMeHoLeu, NMe-HoLeu, NMeHL, NMe-HomoLeu | N-methyl perleucine (a-amino acid) |
| NLeu | N-(2-methylpropyl)glycine |
| NMeNle, NMe-Nle | N-methylnorleucine |
| D-NMePhe | D-N-methylproline |
| NMe-Ser, NMeSer | N-methylserine |
| D-NMeSer, NMe-D-Ser | D-N-methylserine |
| NMeSer, NMeS, NMe-Ser | N-methyl serine |
| D-NMeTyr, D-NMeY, NMe-D-Tyr, NMe-D-Y, | D-N-methyltyrosine |
| NMeVal, NMe-Val | N-methylvaline |
| HoPhe, HomoPhe | Homophenylalanine (α-amino acid) |
| HoPro, S-Pip, HomoPro | S-homoproline, (S)-piperidine-2-carboxylic acid |
| HoSer, HomoSer | Homoserine (α-amino acid) |
| NMe-HoSer | S-N-methyl homoserine |
| NHoSer, NHomoSer | N-(hydroxyethyl)glycine |
| D-HoSer, D-HomoSer | D-homoserine (α-amino acid) |
| NMe-HoSer, NMeHoSer, NMe-Hser, NMeHoS, NMe-HoS, NMe-HoS NMeHomoSer, NMeHomoS, NMe-HomoS, NMe-HomoSer | N-methyl homoserine (α-amino acid) |
| NEt-Leu, NEtLeu, | N-ethyl leucine |
| NiPr-Leu, NiPrLeu, | N-isopropyl leucine |
| NBu-Leu, NBuLeu, | N-n-butyl leucine |
| NPr-Leu, NPrLeu, | N-n-propyl leucine |
| 4-biphenyl acetyl | ![structure of 4-biphenyl acetyl group] |
| 3-Phenylpropanoyl | 3-Phenylpropyl |
| 3,5-Dihydroxybenzyl | 3,5-Dihydroxybenzyl |
| 3PPA | 3-Phenylpropionyl |

TABLE 1-continued

Explanation of amino acid abbreviations

| Abbreviation | Full name |
| --- | --- |
| cyc | The amino group of the N-terminal amino acid and the carboxyl group of the C-terminal amino acid are condensed to form an amide bond for cyclization. |
| Cyc-S | The amino group of the N-terminal amino acid and the carboxyl group of the C-terminal amino acid side chain are condensed to form an amide bond for cyclization. |
| 153ψ(CH$_2$NH)154 | The —CON— bond between the 153$^{rd}$ and 154$^{th}$ amino acids is substituted by —CH$_2$NH—bond. |

The term "pharmaceutically acceptable salt" herein refers to a pharmaceutically acceptable organic or inorganic salt. Examples of the salt include but are not limited to: sulfate, citrate, acetate, oxalate, chloride, bromide, iodide, nitrate, hydrosulfate, phosphate, acid phosphate, isonicotinic acid salt, lactate, salicylic acid salt, acid citrate, tartrate, oleate, tannate, pantothenate, bitartrate, ascorbate, succinate, maleate, gentisinate, fumarate, gluconate, glucuronate, saccharate, formate, benzoate, glutamate, methane sulfonate, ethane sulfonate, benzene sulfonate, p-toluene sulfonate, and embonate (i.e., 1-1-methylene-bis(2-hydroxy-3-naphthoate)). The compounds of the present disclosure may form pharmaceutically acceptable salts with various amino acids. Suitable alkali salts include but are not limited to, aluminum salt, calcium salt, lithium salt, magnesium salt, potassium salt, sodium salt, zinc salt, bismuth salt and diethanolamine salt. For a review of the pharmaceutically acceptable salts, see *Handbook of Pharmaceutical Salts: Properties, Selection, and Use* (P Heinrich Stahl and Camille G. Wermuth, ed., Wiley-VCH, 2002).

As used herein, the term "crystal form" refers to one or more crystal structures formed by the different arrangement of molecules in the lattice space when crystallized.

The term "solvate" refers to a crystal form, in addition to the active molecules, which further comprises one or more solvent molecule(s) incorporated into the crystal structure. The solvate may include a stoichiometric amount or a non-stoichiometric amount of solvent, and the solvent molecule in the solvent may exist in an ordered or non-ordered arrangement. The solvate containing a non-stoichiometric amount of solvent molecules may be obtained by the loss of at least part of solvent molecule (but not all) from the solvate. In a particular embodiment, a solvate refers to a hydrate, which means the crystal of the compound further comprises water molecules.

The term "prodrug" refers to a derivative of the compound comprising a biologically reactive functional group such that the biological reactive functional group can be cleaved from the compound or react in other ways to give the compound under biological conditions (in vivo or in vitro). Usually, the prodrug is inactive, or at least has lower activity than the compound itself, so that the compound exhibits its activity until it is cleaved from the biologically reactive functional group. The biologically reactive functional group can be hydrolyzed or oxidized under biological conditions to give the compound. For instance, the prodrug may contain a biologically hydrolysable group. Examples of the biologically hydrolysable group include but are not limited to: a biologically hydrolysable phosphate, a biologically hydrolysable ester, a biologically hydrolysable amide, a biologically hydrolysable carbonic ester, a biologically hydrolysable carbamate and a biologically hydrolysable ureide. For a review of the prodrug, see, for example, J. Rautio et al., *Nature Reviews Drug Discovery* (2008) 7, 255-270 and *Prodrugs: Challenges and Rewards* (V. Stella et al. ed., Springer, 2007).

The positive progress of the present disclosure is that the peptide compound of the present disclosure has better stability and better activity.

DETAILED DESCRIPTION OF THE PREFERRED EMBODIMENT

The following embodiments further illustrate the present disclosure, but the present disclosure is not limited thereto. The present disclosure has been described in detail in the text, and its specific embodiments have also been disclosed, for one skilled in the art, it is obvious to modify and improve the embodiments of the present disclosure within the spirit and scope of the present disclosure.

Peptide sequences of the present disclosure can be synthesized by the Fmoc-polyamide solid-phase peptide synthesis method as described in Lu et al. (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using N,N-dimethylformamide containing 20% piperidine. Side-chain functionalities may be protected as their butyl ethers (in the case of serine, threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). When the C-terminal residue is glutamine or asparagine, the 4,4'-dimethoxybenzhydryl group is used to protect the side chain amino functionality. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mixture. Scavengers commonly used are ethanedithiol, phenol, anisole and water, the exact choice depending on the constituent amino acids of the peptide being synthesized. Trifluoroacetic acid is removed by evaporation in vacuum, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometry analysis.

The peptide sequences of the molecules of the present disclosure can also be synthesized using liquid phase methods well known to those skilled in the chemical and biochemical arts.

Embodiment 1

Preparation of (D-Tyr)-Phe-Leu-Pro-(D-Ser)-Gln-Phe-(D-Ala)-Tic-Ser (Compound YW-3) (SEQ ID NO: 102)

Step 1: The polypeptide was synthesized by standard Fmoc chemistry, and the basic procedure was as follows. 600 mg of commercially available 2-CTC resin (1.4 mol/g) was swollen in DCM (10 mL) for 30 minutes, followed by addition of Fmoc-Ser(tBu)-OH (120 mg, 0.31 mmol) and DIPEA (1 mL, 5.7 mmol), and treated at room temperature for 3 hours, followed by addition of methanol (0.5 mL) and vibration for 1 hour to block the unreacted resin. The resin was washed with DMF, followed by addition of 20% piperidine/DMF solution (10 mL), and reacted for 20 minutes, and such procedure was repeated twice to remove Fmoc. The resin was washed with DMF, followed by addition of 10 mL of solution of Fmoc-Tic-OH (359 mg, 0.9 mmol), HATU (342 mg, 0.9 mmol) and HOBT (121 mg, 0.9 mmol) in DMF, then DIPEA (350 mg, 2.7 mmol) was added, and reacted at room temperature for 2 hours to obtain Fmoc-Tic-Ser(tBu)-2-CTC resin. Other amino acids were introduced in a similar manner to obtain [D-Tyr(tBu)]-Phe-Leu-Pro-[D-Ser(tBu)]-Gln(Trt)-Phe-(D-Ala)-Tic-Ser(tBu)-CTC resin (SEQ ID NO: 121-CTC resin). The resin was washed with DCM, methanol and methyl tert-butyl ether, and then dried to obtain 760 g of yellow resin.

Step 2 (Conventional peptide cleavage method): The dried resin was added to 10 mL of TFA/TIS/H$_2$O (90/5/5) solution, followed by vibration for 2 hours, and the resin was isolated by filtration. The resin was washed with 2 mL of TFA/TIS/H$_2$O (90/5/5) solution. The filtrate was combined, followed by addition of diethyl ether (70 mL), and allowed to stand at room temperature for 30 minutes. The obtained mixture was centrifuged at 3000 rpm for 1 minute, and the crude polypeptide was washed with diethyl ether (50 mL×2) and dried.

Step 3: The crude product was subjected to a linear gradient elution (10 minutes) at a flow rate of 50 mL/min. The eluent A/B: 80/20-55/45 was: eluent A: 0.05% solution of TFA in water; eluent B: 0.05% solution of TFA in acetonitrile. The preparative HPLC was performed on Sunfire C18, 10 μm, 120 Å column (3×100 mm). The fractions containing the product were collected and lyophilized to obtain a white solid in 500 mg.

Mass spectrometry [M+2H]$^{2+}$/2: 609.9.

Embodiment 2

Preparation of 3-phenylpropanoyl-(D-Tyr)-Phe-Leu-Pro-(D-Ser)-Gln-Phe-(D-Ala)-Tic-Ser-OH (Compound YW-71) (SEQ ID NO: 88)

The resin obtained in the step 1 of Embodiment 1 was swollen with DMF, and then condensed with 3-phenylpropanoic acid (3 equivalent). The condensation reaction was performed under HBTU/HOBt/DIPEA condition, using DMF as the solvent, and the mixture was reacted at room temperature for 3 hours. The resin was dried after washing. The desired polypeptide was cleaved from the resin by the method of step 2, followed by deprotection. The crude product YW-71 was purified by HPLC, eluted with a linear gradient (8.5 min) at a flow rate of 30 mL/min. The eluent A/B: 53/47-44/56 was: eluent A: 0.05% solution of TFA in water; eluent B: 0.05% solution of TFA in acetonitrile. The preparative HPLC was performed on SHIMADAZU C18, 10 μm, 120 Å column (2×21.2×250 mm). The fractions containing the product were collected and lyophilized to obtain a white solid in 20.2 mg.

Embodiment 3

Preparation of Phenethylcarbamoyl-(D-Tyr)-Phe-Leu-Pro-(D-Ser)-Gln-Phe-(D-Ala)-Tic-Ser-OH (Compound YW-72) (SEQ ID NO: 89)

The crude product of Embodiment 1 with phenylethyl isocyanate (132 mg, 0.9 mmol) and diisopropylethylamine (113 mg, 0.9 mmol) were dissolved in DMF (4 mL) without purification, and vibrated for 2 hours to obtain a reaction solution containing the product phenethylcarbamothioyl-(D-Tyr)-Phe-Leu-Pro-(D-Ser)-Gln-Phe-(D-Ala)-Tic-Ser. The crude product was subjected to a linear gradient elution (8.5 min) at a flow rate of 30 mL/min. The eluent A/B: 53/47-44/56 was: eluent A: 0.05% solution of TFA in water; eluent B: 0.05% solution of TFA in acetonitrile. The preparative HPLC was performed on 2×Sunfire C18, 5 μm, 120 Å column (19×150 mm). The fractions containing the product were collected and lyophilized to give a white solid in 80 mg.

Mass spectrometry [M+2H]$^{2+}$/2: 683.5.

Embodiment 4

Preparation of Phenethylcarbamothioyl-(D-Tyr)-Phe-Leu-Pro-(D-Ser)-Gln-Phe-(D-Ala)-Tic-Ser-OH (Compound YW-73) (SEQ ID NO: 90)

The crude product of Embodiment 1 with phenyl isothiocyanate (40 mg, 0.3 mmol) and diisopropylethylamine (113 mg, 0.9 mmol) were dissolved in DMF (4 mL) without purification, and vibrated for 2 hours to obtain a reaction solution containing the product phenethyl isothiocyanate-(D-Tyr)-Phe-Leu-Pro-(D-Ser)-Gln-Phe-(D-Ala)-Tic-Ser.

The crude product was subjected to a linear gradient elution (8.5 min) at a flow rate of 20 mL/min. The eluent A/B: 51/49-44/56 was: eluent A: 0.07% solution of ammonium bicarbonate in water and 0.05% ammonia in water; eluent B: acetonitrile. The preparative HPLC was performed on 2×Sunfire C18, 5 µm, 120 Å column (19×150 mm). The fractions containing the product were collected and lyophilized to give a white solid in 13.7 mg.

Mass spectrometry $[M+2H]^{2+}/2$: 691.5

Embodiment 5

Preparation of 3-Phenylpropyl-(D-Tyr)-Phe-Leu-Pro-(D-Ser)-Gln-Phe-(D-Ala)-Tic-Ser-OH (Compound YW-74) (SEQ ID NO: 91)

A solution of 3-phenylpropanal (50 mg, 0.37 mmol) and acetic acid (20 mg) in DMF (5 mL) was added into the fully protected [D-Tyr(tBu)]-Phe-Leu-Pro-[D-Ser(tBu)]-Gln(Trt)-Phe-(D-Ala)-Tic-Ser(tBu)-CTC resin (SEQ ID NO: 121-CTC resin) obtained in step 1 of Embodiment 1. The mixture was reacted at room temperature for 0.5 hour, followed by addition of sodium borohydride (47 mg, 1.24 mmol), and reacted at room temperature for 2.5 hours. The resin was washed with DCM, methanol, methyl tert-butyl ether and then dried to obtain a yellow resin in 370 mg.

The dried resin was added into 5 mL of TFA/TIS/$H_2O$ (95/2.5/2.5) solution, followed by vibration for 2.5 hours. The resin was isolated by filtration and washed with 2 mL of TFA/TIS/$H_2O$ (90/5/5) solution. The filtrate was combined, and diethyl ether (50 mL) was added into the filtrate and allowed to stand at room temperature for 30 minutes. The obtained mixture was centrifuged at 3000 rpm for 1 minute and the supernatant was removed. The obtained precipitate was dissolved in DMF, and subjected to a linear gradient elution (10 min) at a flow rate of 20 mL/min. The eluent A/B: 69/31-63/37 was: eluent A: 0.05% solution of TFA in water; eluent B: 0.05% solution of TFA in acetonitrile. The preparative HPLC was performed on Sunfire C18, 5 µm, 120 Å column (19×150 mm). The fractions containing the product were collected and lyophilized to obtain a white solid in 13.7 mg.

Mass spectrometry $[M+2H]^{2+}/2$: 669.2.

Embodiment 6

Preparation of 4-Phenylbutanoyl-(D-Tyr)-Phe-Leu-Pro-(D-Ser)-Gln-Phe-(D-Ala)-Tic-Ser-OH (Compound YW-75) (SEQ ID NO: 92)

Referring to the synthesis method similar to that of Embodiment 2, 4-phenylpropanoic acid (3 equivalent) was used for condensation and the condensation reaction was performed under HBTU/HOBt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-75 was purified by HPLC, eluted with a linear gradient (8.5 min) at a flow rate of 30 mL/min. The eluent A/B: 51.5/48.5-43/57 was: eluent A: 0.05% solution of TFA in water; eluent B: 0.05% solution of TFA in acetonitrile. The preparative HPLC was performed on SHIMADAZU C18, 10 µm, 120 Å column (2×21.2×250 mm). The fractions containing the product were collected and lyophilized to obtain a white solid in 20.6 mg.

Embodiment 7

Preparation of 5-phenylvaleroyl-(D-Tyr)-Phe-Leu-Pro-(D-Ser)-Gln-Phe-(D-Ala)-Tic-Ser-OH (Compound YW-76) (SEQ ID NO: 93)

Referring to the synthesis method similar to that of Embodiment 2, 5-phenylvaleric acid (3 equivalent) was used for condensation and the condensation reaction was performed under HBTU/HOBt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-76 was purified by HPLC, eluted with a linear gradient (8.5 min) at a flow rate of 30 mL/min. The eluent A/B: 49/51-41/59 was: eluent A: 0.05% solution of TFA in water; eluent B: 0.05% solution of TFA in acetonitrile. The preparative HPLC was performed on SHIMADAZU C18, 10 µm, 120 Å column (2×21.2×250 mm). The fractions containing the product were collected and lyophilized to obtain a white solid in 20.7 mg.

Embodiment 8

Preparation of 4-biphenylacetyl-(D-Tyr)-Phe-Leu-Pro-(D-Ser)-Gln-Phe-(D-Ala)-Tic-Ser-OH (Compound YW-77) (SEQ ID NO: 94)

Referring to the synthesis method similar to that of Embodiment 2, 4-biphenyl acetic acid (3 equivalent) was used for condensation and the condensation reaction was performed under HBTU/HOBt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-77 was purified by HPLC, eluted with a linear gradient (8.5 min) at a flow rate of 30 mL/min. The eluent A/B: 48/52-40/60 was: eluent A: 0.05% solution of TFA in water; eluent B: 0.05% solution of TFA in acetonitrile. The preparative HPLC was performed on SHIMADAZU C18, 10 µm, 120 Å column (2×21.2×250 mm). The fractions containing the product were collected and lyophilized to obtain a white solid in 20.8 mg.

Embodiment 9

Preparation of diphenylacetyl-(D-Tyr)-Phe-Leu-Pro-(D-Ser)-Gln-Phe-(D-Ala)-Tic-Ser-OH (Compound YW-78) (SEQ ID NO: 95)

Referring to the synthesis method similar to that of Embodiment 2, diphenylacetic acid (3 equivalent) was used for condensation and the condensation reaction was performed under HBTU/HOBt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-78 was purified by HPLC, eluted with a linear gradient (8.5 min) at a flow rate of 30 mL/min. The eluent A/B: 49/51-41/59 was: eluent A: 0.05% solution of TFA in water; eluent B: 0.05% solution of TFA in acetonitrile. The preparative HPLC was performed on SHIMADAZU C18, 10 µm, 120 Å column (2×21.2×250 mm).

Embodiment 10

Preparation of 3,5-dihydroxybenzoyl-(D-Tyr)-Phe-Leu-Pro-(D-Ser)-Gln-Phe-(D-Ala)-Tic-Ser-OH (Compound YW-79) (SEQ ID NO: 96)

Referring to the synthesis method similar to that of Embodiment 2, 3,5-dihydroxybenzoic acid (3 equivalent) was used for condensation and the condensation reaction was performed under HBTU/HOBt/DIPEA condition using DMF as the solvent, and the mixture was reacted at room temperature for 5 hours. The resin was dried after washing. The desired polypeptide was cleaved from the resin by the method of step 2 in Embodiment 1, followed by deprotection. The crude product YW-79 was purified by HPLC, eluted with a linear gradient (8.5 min) at a flow rate of 30 mL/min. The eluent A/B: 60/40-53/47 was: eluent A: 0.05% solution of TFA in water; eluent B: 0.05% solution of TFA in acetonitrile. The preparative HPLC was performed on SHIMADAZU C18, 10 μm, 120 Å column (2×21.2×250 mm). The fractions containing the product were collected and lyophilized to obtain a white solid in 21.3 mg.

Embodiment 11

Preparation of (D-Tyr)-Phe-Leu-Pro-(D-Ser)-Gln-Phe-(D-Ala)-HoPro-Ser-OH (Compound YW-90) (SEQ ID NO: 103)

Referring to the synthesis method similar to that of Embodiment 1, Fmoc-Tic was replaced with Fmoc-HoPro-OH (3 equivalent) for condensation and the condensation reaction was performed under HBTU/HOBt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-90 was purified by HPLC, eluted with a linear gradient (10 min) at a flow rate of 25 mL/min. The eluent A/B: 76/24-68/32 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 9.8 mg.

Embodiment 12

Preparation of (D-Tyr)-Phe-Leu-Pro-(D-Ser)-Gln-Phe-(D-Ala)-Pro(5Ph)-Ser-OH (Compound YW-91) (SEQ ID NO: 104)

Referring to the synthesis method similar to that of Embodiment 1, Fmoc-Tic was replaced with Fmoc-Pro(5Ph)-OH (3 equivalent) for condensation and the condensation reaction was performed under HBTU/HOBt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-91 was purified by HPLC, eluted with a linear gradient (10 min) at a flow rate of 20 mL/min. The eluent A/B: 73/27-63/37 was: eluent A: 0.05% solution of TFA in water; eluent B: 0.05% solution of TFA in acetonitrile. The preparative HPLC was performed on Sunfire C18, 5 μm, 120 Å column (19×150 mm). The fractions containing the product were collected and lyophilized to obtain a white solid in 20.1 mg.

Embodiment 13

Preparation of (D-Tyr)-Phe-Leu-Pro-(D-Ser)-Gln-Phe-(D-Ala)-Pro(4Ph)-Ser-OH (Compound YW-92) (SEQ ID NO: 105)

Referring to the synthesis method similar to that of Embodiment 1, Fmoc-Tic was replaced with Fmoc-Pro(4Ph)-OH (3 equivalent) for condensation and the condensation reaction was performed under HBTU/HOBt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-92 was purified by HPLC, eluted with a linear gradient (10 min) at a flow rate of 20 mL/min. The eluent A/B: 70/30-60/40 was: eluent A: 0.05% solution of TFA in water; eluent B: 0.05% solution of TFA in acetonitrile. The preparative HPLC was performed on Sunfire C18, 5 μm, 120 Å column (19×150 mm). The fractions containing the product were collected and lyophilized to obtain a white solid in 20.1 mg.

Embodiment 14

Preparation of (D-Tyr)-Phe-Leu-Pro-(D-Ser)-Gln-Phe-(D-Ala)-(S)-isoindoline-1-carboxyl-Ser-OH (Compound YW-93) (SEQ ID NO: 106)

Referring to the synthesis method similar to that of Embodiment 1, Fmoc-Tic was replaced with Fmoc-(S)-isoindoline-1-carboxylic acid (3 equivalent) for condensation and the condensation reaction was performed under HBTU/HOBt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-93 was purified by HPLC, eluted with a linear gradient (10 min) at a flow rate of 25 mL/min. The eluent A/B: 74/26-64/36 was: eluent A: 0.05% solution of TFA in water; eluent B: 0.05% solution of TFA in acetonitrile. The preparative HPLC was performed on Phenomenex Gemini C18, 10 μm, 110 Å column (21.2×250 mm). The fractions containing the product were collected and lyophilized to obtain 24.9 mg of P1 as a white solid and 23.0 mg of P2 as a white solid.

Embodiment 15

Preparation of (D-Tyr)-Phe-Leu-Pro-(D-Ser)-Gln-Phe-(D-Ala)-Ala(dip)-Ser-OH (Compound YW-94) (SEQ ID NO: 107)

Referring to the synthesis method similar to that of Embodiment 1, Fmoc-Tic was replaced with Fmoc-Ala(dip)-OH (3 equivalent) for condensation and the condensation reaction was performed under HBTU/HOBt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-94 was purified by HPLC, eluted with a linear gradient (10 min) at a flow rate of 20 mL/min. The eluent A/B: 69/31-63/37 was: eluent A: 0.05% solution of TFA in water; eluent B: 0.05% solution of TFA in acetonitrile. The preparative HPLC was performed on Sunfire C18, 5 μm, 120 Å column (19×150 mm). The fractions containing the product were collected and lyophilized to obtain a white solid in 20.2 mg.

Embodiment 16

Preparation of (D-Tyr)-Phe-Leu-Pro-(D-Ser)-Gln-Phe-(D-Ala)-Bip-Ser-OH (Compound YW-95) (SEQ ID NO: 108)

Referring to the synthesis method similar to that of Embodiment 1, Fmoc-Tic was replaced with Fmoc-Bip-OH (3 equivalent) for condensation and the condensation reaction was performed under HBTU/HOBt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-95 was purified by HPLC, eluted with a linear gradient (8.5 min) at a flow rate of 30 mL/min. The eluent A/B: 61/39-55/45 was: eluent A: 0.05% solution of TFA in water; eluent B: 0.05% solution of TFA in acetonitrile. The preparative HPLC was performed on SHIMADAZU C18, 10 μm, 120 Å column (2×21.2×250 mm). The fractions containing the product were collected and lyophilized to obtain a white solid in 20.6 mg.

Embodiment 17

Preparation of (D-Tyr)-Phe-Leu-Pro-(D-Ser)-Gln-Phe-(D-Ala)-Bip-Ser-OH (Compound YW-96) (SEQ ID NO: 67)

Referring to the synthesis method similar to that of Embodiment 1, Fmoc-Pro was replaced with Fmoc-HoPro-OH (3 equivalent) for condensation and the condensation reaction was performed under HBTU/HOBt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-96 was purified by HPLC, eluted with a linear gradient (10 min) at a flow rate of 20 mL/min. The eluent A/B: 72/28-66/34 was: eluent A: 0.05% solution of TFA in water; eluent B: 0.05% solution of TFA in acetonitrile. The preparative HPLC was performed on Sunfire C18, 5 μm, 120 Å column (19×150 mm). The fractions containing the product were collected and lyophilized to obtain a white solid in 6.0 mg.

Embodiment 18

Preparation of (D-Phe)-Phe-Leu-Pro-(D-Ser)-Gln-Phe-(D-Ala)-Tic-Ser-OH (Compound YW-97) (SEQ ID NO: 68)

Referring to the synthesis method similar to that of Embodiment 1, Fmoc-D-Tyr was replaced with Fmoc-D-Phe (3 equivalent) for condensation and the condensation reaction was performed under HBTU/HOBt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-97 was purified by HPLC, eluted with a linear gradient (10 min) at a flow rate of 25 mL/min. The eluent A/B: 61/39-54/46 was: eluent A: 0.05% solution of TFA in water; eluent B: 0.05% solution of TFA in acetonitrile. The preparative HPLC was performed on Sunfire C18, 10 μm, 120 Å column (19×250 mm). The fractions containing the product were collected and lyophilized to obtain a white solid in 38.4 mg.

Embodiment 19

Preparation of (D-Tyr)-Phe-(NMe-Leu)-Pro-(D-Ser)-Gln-Phe-(D-Ala)-Tic-Ser-OH (Compound YW-98) (SEQ ID NO: 1)

Referring to the synthesis method similar to that of Embodiment 1, Fmoc-Leu was replaced with Fmoc-NMe-Leu (3 equivalent) for condensation and the condensation reaction was performed under HATU/HOAt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-98 was purified by HPLC, eluted with a linear gradient (10 min) at a flow rate of 25 mL/min. The eluent A/B: 73/27-63/37 was: eluent A: 0.05% solution of TFA in water; eluent B: 0.05% solution of TFA in acetonitrile. The preparative HPLC was performed on Sunfire C18, 5 μm, 120 Å column (19×150 mm). The fractions containing the product were collected and lyophilized to obtain a white solid in 24.9 mg.

Embodiment 20

Preparation of (D-Tyr)-Phe-(NMe-Val)-Pro-(D-Ser)-Gln-Phe-(D-Ala)-Tic-Ser-OH (Compound YW-99) (SEQ ID NO: 109)

Referring to the synthesis method similar to that of Embodiment 1, Fmoc-Leu was replaced with Fmoc-NMe-Val (3 equivalent) for condensation and the condensation reaction was performed under HATU/HOAt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-99 was purified by HPLC, eluted with a linear gradient (10 min) at a flow rate of 20 mL/min. The eluent A/B: 76/24-70/30 was: eluent A: 0.05% solution of TFA in water; eluent B: 0.05% solution of TFA in acetonitrile. The preparative HPLC was performed on Sunfire C18, 5 μm, 120 Å column (19×150 mm). The fractions containing the product were collected and lyophilized to obtain a white solid in 19.5 mg.

Embodiment 21

Preparation of (D-Tyr)-Phe-(NMe-Phe)-Pro-(D-Ser)-Gln-Phe-(D-Ala)-Tic-Ser-OH (Compound YW-100) (SEQ ID NO: 2)

Referring to the synthesis method similar to that of Embodiment 1, Fmoc-Leu was replaced with Fmoc-NMe-Phe (3 equivalent) for condensation and the condensation reaction was performed under HATU/HOAt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-100 was purified by HPLC, eluted with a linear gradient (8.5 min) at a flow rate of 30 mL/min. The eluent A/B: 65/35-59/41 was: eluent A: 0.05% solution of TFA in water; eluent B: 0.05% solution of TFA in acetonitrile. The preparative HPLC was performed on SHIMADAZU C18, 10 μm, 120 Å column (2×21.2×250 mm). The fractions containing the product were collected and lyophilized to obtain a white solid in 5.8 mg.

Embodiment 22

Preparation of (D-Tyr)-Phe-(NMe-HoLeu)-Pro-(D-Ser)-Gln-Phe-(D-Ala)-Tic-Ser-OH (Compound YW-101) (SEQ ID NO: 3)

Referring to the synthesis method similar to that of Embodiment 1, Fmoc-Leu was replaced with Fmoc-NMe-HoLeu (3 equivalent) for condensation and the condensation reaction was performed under HATU/HOAt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-101 was purified by HPLC, eluted with a linear gradient (8.5 min) at a flow rate of 30 mL/min. The eluent A/B: 65/35-59/41 was: eluent A: 0.05% solution of TFA in water; eluent B: 0.05% solution of TFA in acetonitrile. The preparative HPLC was performed on SHIMADAZU C18, 10 μm, 120 Å column (2×21.2×250 mm). The fractions containing the product were collected and lyophilized to obtain a white solid in 25.2 mg.

Embodiment 23

Preparation of (D-Tyr)-Phe-NLeu-Pro-(D-Ser)-Gln-Phe-(D-Ala)-Tic-Ser-OH (Compound YW-102) (SEQ ID NO: 110)

Step 1: 600 mg of commercially available 2-CTC resin (1.4 mol/g) was swollen in DCM (10 mL) for 30 minutes, followed by addition of Fmoc-Ser(tBu)-OH (120 mg, 0.31 mmol) and DIPEA (1 mL, 5.7 mmol), and treated at room temperature for 3 hours, followed by addition of methanol (0.5 mL) and vibration for 1 hour to block the unreacted resin. The resin was washed with DMF, followed by addition of 20% piperidine/DMF solution (10 mL), and reacted for 20 minutes, and such procedure was repeated twice to remove Fmoc. The resin was washed with DMF, followed by addition of 10 mL of solution of Fmoc-Tic-OH (600 mg, 1.5 mmol), HATU (570 mg, 1.5 mmol) and HOBT (202 mg, 1.5 mmol) in DMF, then DIPEA (580 mg, 4.5 mmol) was added, and reacted at room temperature for 2 hours to obtain Fmoc-Tic-Ser(tBu)-2-CTC. Other amino acids were introduced in a similar manner to obtain Pro-[D-Ser(tBu)]-Gln (Trt)-Phe-(D-Ala)-Tic-Ser(tBu)-CTC resin (SEQ ID NO: 122-CTC resin).

Step 2: A solution of bromoacetic acid (348 mg, 2.5 mmol) and DIC (630 mg, 5 mmol) in DMF (10 mL) was added into the above resin, and the mixture was reacted at room temperature for 1 hour, followed by filtration. The resin was washed with DMF (10 mL×6). A solution of 2-methylpropylamine hydrochloride (413 mg, 3.77 mmol), triethylamine (760 mg, 7.52 mmol) and DMSO (1 mL) in DMF (10 mL) was then added into the resin, and the mixture was reacted at room temperature for 3 hours. The resin was washed with DMF (10 mL×6) to obtain NLeu-Pro-[D-Ser(tBu)]-Gln(Trt)-Phe-(D-Ala)-Tic-Ser(tBu)-CTC resin (SEQ ID NO: 123-CTC resin).

Step 3: The last 2 amino acids were attached to the above resin by Fmoc deprotection and amino acid coupling reaction alternately. The resin was washed with DCM, methanol, methyl tert-butyl ether and then dried to obtain a yellow resin in 866 mg.

Step 4: The dried resin was added to 10 mL of TFA/TIS/H$_2$O (90/5/5) solution, followed by vibration for 2.5 hours, and the resin was isolated by filtration. The resin was washed with 2 mL of TFA/TIS/H$_2$O (90/5/5) solution. The filtrate was combined, followed by addition of diethyl ether (50 mL), and allowed to stand at room temperature for 30 minutes. The obtained mixture was centrifuged at 3000 rpm for 1 minute and the supernatant was removed. The obtained precipitate was dissolved in DMF, followed by a linear gradient elution (10 min) at a flow rate of 20 mL/min. The eluent AB: 71/29-65/35 was: eluent A: 0.05% solution of TFA in water; eluent B: 0.05% solution of TFA in acetonitrile. The preparative HPLC was performed on Sunfire C18, 5 μm, 120 Å column (19×150 mm). The fractions containing the product were collected and lyophilized to obtain a white solid in 28 mg.

Mass spectrometry $[M+2]^{2+}/2$: 609.9.

Embodiment 24

Preparation of (D-NMe-Tyr)-Phe-Leu-Pro-(D-Ser)-Gln-Phe-(D-Ala)-Tic-Ser-OH (Compound YW-103) (SEQ ID NO: 69)

Referring to the synthesis method similar to that of Embodiment 1, Fmoc-D-Tyr was replaced with Fmoc-D-NMeTyr (3 equivalent) for condensation and the condensation reaction was performed under HATU/HOAt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-103 was purified by HPLC, eluted with a linear gradient (8.5 min) at a flow rate of 20 mL/min. The eluent A/B: 73/27-63/37 was: eluent A: 0.05% solution of TFA in water; eluent B: 0.05% solution of TFA in acetonitrile. The preparative HPLC was performed on Sunfire C18, 5 μm, 120 Å column (19×150 mm). The fractions containing the product were collected and lyophilized to obtain a white solid in 28.5 mg.

Embodiment 25

Preparation of (D-Tyr)-(NMe-Phe)-Leu-Pro-(D-Ser)-Gln-Phe-(D-Ala)-Tic-Ser-OH (Compound YW-104) (SEQ ID NO: 70)

Referring to the synthesis method similar to that of Embodiment 1, Fmoc-Phe was replaced with Fmoc-NMe-Phe (3 equivalent) for condensation and the condensation reaction was performed under HATU/HOAt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-104 was purified by HPLC, eluted with a linear gradient (8.5 min) at a flow rate of 30 mL/min. The eluent A/B: 62/38-55/45 was: eluent A: 0.05% solution of TFA in water; eluent B: 0.05% solution of TFA in acetonitrile. The preparative HPLC was performed on SHIMADAZU C18, 10 µm, 120 Å column (2×21.2×250 mm). The fractions containing the product were collected and lyophilized to obtain a white solid in 28.6 mg.

Embodiment 26

Preparation of (D-Tyr)-(NMe-Phe)-(NMe-Leu)-Pro-(D-Ser)-Gln-Phe-(D-Ala)-Tic-Ser-OH (Compound YW-105) (SEQ ID NO: 4)

Referring to the synthesis method similar to that of Embodiment 1, Fmoc-Leu was replaced with Fmoc-NMe-Leu (3 equivalent) for condensation and the condensation reaction was performed under HATU/HOAt/DIPEA condition using DMF as the solvent, and the mixture was reacted at room temperature for 3 hours. Fmoc-Phe was replaced with Fmoc-NMe-Phe (3 equivalent) for condensation and the condensation reaction was performed under HATU/HOAt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-105 was purified by HPLC, eluted with a linear gradient (8.5 min) at a flow rate of 30 mL/min. The eluent A/B: 66.5/33.5-59/41 was: eluent A: 0.05% solution of TFA in water; eluent B: 0.05% solution of TFA in acetonitrile. The preparative HPLC was performed on SHIMADAZU C18, 10 µm, 120 Å column (2×21.2×250 mm). The fractions containing the product were collected and lyophilized to obtain a white solid in 20.3 mg.

Embodiment 27

Preparation of (D-Tyr)-Phe-Leu-Pro-(D-NMeSer)-Gln-Phe-(D-Ala)-Tic-Ser-OH (Compound YW-106) (SEQ ID NO: 111)

Referring to the synthesis method similar to that of Embodiment 1, Fmoc-D-Ser was replaced with Fmoc-NMe-D-Ser (3 equivalent) for condensation and the condensation reaction was performed under HATU/HOAt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-106 was purified by HPLC, eluted with a linear gradient (10 min) at a flow rate of 20 mL/min. The eluent A/B: 71/29-65/35 was: eluent A: 0.05% solution of TFA in water; eluent B: 0.05% solution of TFA in acetonitrile. The preparative HPLC was performed on Sunfire C18, 5 µm, 120 Å column (19×150 mm). The fractions containing the product were collected and lyophilized to obtain a white solid in 27.3 mg.

Embodiment 28

Preparation of (D-Tyr)-Phe-Leu-Pro-(D-Ser)-(NMe-Gln)-Phe-(D-Ala)-Tic-Ser-OH (Compound YW-107) (SEQ ID NO: 112)

Referring to the synthesis method similar to that of Embodiment 1, Fmoc-Gln was replaced with Fmoc-NMe-Gln (3 equivalent) for condensation and the condensation reaction was performed under HATU/HOAt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-107 was purified by HPLC, eluted with a linear gradient (10 min) at a flow rate of 20 mL/min. The eluent A/B: 70/30-63/37 was: eluent A: 0.05% solution of TFA in water; eluent B: 0.05% solution of TFA in acetonitrile. The preparative HPLC was performed on Sunfire C18, 5 µm, 120 Å column (19×150 mm). The fractions containing the product were collected and lyophilized to obtain a white solid in 29.1 mg.

Embodiment 29

Preparation of (D-Tyr)-Phe-Leu-Pro-(D-Ser)-NGln-Phe-(D-Ala)-Tic-Ser-OH (Compound YW-108) (SEQ ID NO: 113)

Referring to the step 1 of Embodiment 5, starting from 600 mg of commercially available 2-CTC resin (1.4 mol/g), various amino acids were introduced by standard Fmoc chemistry to obtain Phe-(D-Ala)-Tic-Ser(tBu)-CTC resin.

Step 2: A solution of bromoacetic acid (348 mg, 2.5 mmol) and DIC (630 mg, 5 mmol) in DMF (10 mL) was added into the above resin, and the mixture was reacted at room temperature for 1 hour, followed by filtration. The resin was washed with DMF (10 mL×6). A solution of 3-aminopropanamide hydrochloride (470 mg, 3.77 mmol), triethylamine (760 mg, 7.52 mmol) and DMSO (1 mL) in DMF (10 mL) was then added into the resin, and the mixture was reacted at room temperature for 3 hours. The resin was washed with DMF (10 mL×6) to obtain NGln-Phe-(D-Ala)-Tic-Ser(tBu)-CTC resin (SEQ ID NO: 124-CTC resin).

Step 3: The last 5 amino acids were attached to the above resin by Fmoc deprotection and amino acid coupling reaction alternately. The resin was washed with DCM, methanol, methyl tert-butyl ether and then dried to obtain a yellow resin in 900 mg.

Step 4: The dried resin was added to 10 mL of TFA/TIS/$H_2O$ (95/2.5/2.5) solution, followed by vibration for 2.5 hours, and the resin was isolated by filtration. The resin was washed with 2 mL of TFA/TIS/$H_2O$ (95/2.5/2.5) solution. The filtrate was combined, followed by addition of diethyl ether (50 mL), and allowed to stand at room temperature for 30 minutes. The obtained mixture was centrifuged at 3000 rpm for 1 minute and the supernatant was removed. The obtained precipitate was dissolved in DMF, followed by a linear gradient elution (10 min) at a flow rate of 20 mL/min. The eluent A/B: 71/29-65/35 was: eluent A: 0.05% solution of TFA in water; eluent B: 0.05% solution of TFA in acetonitrile. The preparative HPLC was performed on Sunfire C18, 5 um, 120 Å column (19×150 mm). The fractions containing the product were collected and lyophilized to obtain a white solid in 16 mg.

Mass spectrometry $[M+2]^{2+}/2$: 610.0.

Embodiment 30

Preparation of (D-Tyr)-Phe-Leu-Pro-(D-Ser)-Gln-Phe-(D-NMe-Ala)-Tic-Ser-OH (Compound YW-109) (SEQ ID NO: 114)

Referring to the synthesis method similar to that of Embodiment 1, Fmoc-D-Ala was replaced with Fmoc-D-NMe-Ala (3 equivalent) for condensation and the condensation reaction was performed under HATU/HOAt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-109 was purified by HPLC, eluted with a linear gradient (8.5 min) at a flow rate of 30 mL/min. The eluent A/B: 66.5/33.5-59/41 was: eluent A: 0.05% solution of TFA in water; eluent B: 0.05% solution of TFA in acetonitrile. The preparative HPLC was performed on SHIMADAZU C18, 10 μm, 120 Å column (2×21.2×150 mm). The fractions containing the product were collected and lyophilized to obtain a white solid in 28.2 mg.

Embodiment 31

Preparation of (D-Tyr)-Phe-Leu-Pro-(D-Ser)-Gln-Phe-(D-Ala)-Tic-(NMe-Ser)-OH (Compound YW-110) (SEQ ID NO: 71)

Referring to the synthesis method similar to that of Embodiment 1, Fmoc-Ser was replaced with Fmoc-NMe-Ser (3 equivalent) for condensation and the condensation reaction was performed under HATU/HOAt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-110 was purified by HPLC, eluted with a linear gradient (8.5 min) at a flow rate of 30 mL/min. The eluent A/B: 66/34-59/41 was: eluent A: 0.05% solution of TFA in water; eluent B: 0.05% solution of TFA in acetonitrile. The preparative HPLC was performed on SHIMADAZU C18, 10 μm, 120 Å column (2×21.2×150 mm). The fractions containing the product were collected and lyophilized to obtain a white solid in 22.8 mg.

Embodiment 32

Preparation of 3-phenylpropanoyl-(D-Tyr)-Phe-(NMe-Leu)-Pro-(D-Ser)-Gln-Phe-(D-Ala)-Tic-Ser-OH (Compound YW-111) (SEQ ID NO: 5)

Referring to the synthesis method similar to that of Embodiment 2 (YW-71), Fmoc-Leu was replaced with Fmoc-NMe-Leu (3 equivalent) for condensation and the condensation reaction was performed under HATU/HOAt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-111 was purified by HPLC, eluted with a linear gradient (10 min) at a flow rate of 20 mL/min. The eluent A/B: 60/40-50/50 was: eluent A: 0.05% solution of TFA in water; eluent B: 0.05% solution of TFA in acetonitrile. The preparative HPLC was performed on Sunfire C18, 5 μm, 120 Å column (19×150 mm). The fractions containing the product were collected and lyophilized to obtain a white solid in 28.8 mg.

Embodiment 33

Preparation of (D-Tyr)-Phe-Leu-Pro(5Ph)-(D-Ser)-Gln-Phe-(D-Ala)-Tic-Ser-OH (Compound YW-112) (SEQ ID NO: 72)

Referring to the synthesis method similar to that of Embodiment 1, Fmoc-Pro was replaced with Fmoc-Pro(5-Phenyl) (3 equivalent) for condensation and the condensation reaction was performed under HATU/HOAt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-112 was purified by HPLC, eluted with a linear gradient (10 min) at a flow rate of 20 mL/min. The eluent A/B: 66/34-59/41 was: eluent A: 0.05% solution of TFA in water; eluent B: 0.05% solution of TFA in acetonitrile. The preparative HPLC was performed on Sunfire C18, 5 μm, 120 Å column (19×150 mm). The fractions containing the product were collected and lyophilized to obtain a white solid in 23.5 mg.

Embodiment 34

Preparation of (D-Tyr)-Phe-Leu-Pro(4-Ph)-(D-Ser)-Gln-Phe-(D-Ala)-Tic-Ser-OH (Compound YW-113) (SEQ ID NO: 73)

Referring to the synthesis method similar to that of Embodiment 1, Fmoc-Pro was replaced with Fmoc-Pro(4-Phenyl) (3 equivalent) for condensation and the condensation reaction was performed under HATU/HOAt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-113 was purified by HPLC, eluted with a linear gradient (8.5 min) at a flow rate of 30 mL/min. The eluent A/B: 60/40-52/48 was: eluent A: 0.05% solution of TFA in water; eluent B: 0.05% solution of TFA in acetonitrile. The preparative HPLC was performed on SHIMADAZU C18, 10 μm, 120 Å column (2×21.2×250 mm). The fractions containing the product were collected and lyophilized to obtain a white solid in 26.9 mg.

Embodiment 35

Preparation of (D-Tyr)-Phe-Leu-Thz-(D-Ser)-Gln-Phe-(D-Ala)-Tic-Ser-OH (Compound YW-114) (SEQ ID NO: 74)

Referring to the synthesis method similar to that of Embodiment 1, Fmoc-Pro was replaced with Fmoc-Thz (3 equivalent) for condensation and the condensation reaction was performed under HATU/HOAt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-114 was purified by HPLC, eluted with a linear gradient (8.5 min) at a flow rate of 30 mL/min. The eluent A/B: 64/36-59/41 was: eluent A: 0.05% solution of TFA in water; eluent B: 0.05% solution of TFA in acetonitrile. The preparative HPLC was performed on SHIMADAZU C18, 10 μm, 120 Å column (2×21.2×250 mm). The fractions containing the product were collected and lyophilized to obtain a white solid in 7.1 mg.

Embodiment 36

Preparation of (D-Tyr)-Phe-Leu-Aze-(D-Ser)-Gln-Phe-(D-Ala)-Tic-Ser-OH (Compound YW-115) (SEQ ID NO: 75)

Referring to the synthesis method similar to that of Embodiment 1, Fmoc-Pro was replaced with Fmoc-Aze (3 equivalent) for condensation and the condensation reaction was performed under HATU/HOAt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-115 was purified by HPLC, eluted with a linear gradient (8.5 min) at a flow rate of 30 mL/min. The eluent A/B: 67/33-59/41 was: eluent A: 0.05% solution of TFA in water; eluent B: 0.05% solution of TFA in acetonitrile. The preparative HPLC was performed on SHIMADAZU C18, 10 μm, 120 Å column (2×21.2×250 mm). The fractions containing the product were collected and lyophilized to obtain a white solid in 25.7 mg.

Embodiment 37

Preparation of (D-Tyr)-Phe-Leu-Pro-(D-Ser)-Gln-1Nal-(D-Ala)-Tic-Ser-OH (Compound YW-117) (SEQ ID NO: 76)

Referring to the synthesis method similar to that of Embodiment 1, Fmoc-Phe was replaced with Fmoc-1-Nal (3 equivalent) for condensation and the condensation reaction was performed under HATU/HOAt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-117 was purified by HPLC, eluted with a linear gradient (10 min) at a flow rate of 25 mL/min. The eluent A/B: 68/32-58/42 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 25.8 mg.

Embodiment 38

Preparation of (D-Tyr)-Phe-Leu-Pro-(D-Ser)-Gln-2Nal-(D-Ala)-Tic-Ser-OH (Compound YW-118) (SEQ ID NO: 77)

Referring to the synthesis method similar to that of Embodiment 1, Fmoc-Phe was replaced with Fmoc-2Nal (3 equivalent) for condensation and the condensation reaction was performed under HATU/HOAt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-118 was purified by HPLC, eluted with a linear gradient (10 min) at a flow rate of 25 mL/min. The eluent A/B: 71/29-63/37 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 25.4 mg.

Embodiment 39

Preparation of (D-Tyr)-Phe-Leu-Pro-(D-Ser)-Gln-Bpa-(D-Ala)-Tic-Ser-OH (Compound YW-119) (SEQ ID NO: 78)

Referring to the synthesis method similar to that of Embodiment 1, Fmoc-Phe was replaced with Fmoc-Bpa (3 equivalent) for condensation and the condensation reaction was performed under HATU/HOAt/DIPEA condition using DMF as the solvent, and the mixture was reacted at room temperature for 3 hours. The resin was dried after washing. The desired polypeptide was cleaved from the resin by the method of step 2 in Embodiment 1, followed by deprotection. The crude product YW-119 was purified by HPLC, eluted with a linear gradient (10 min) at a flow rate of 25 mL/min. The eluent A/B: 72/28-62/38 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 24.4 mg.

Embodiment 40

Preparation of (D-Tyr)-Phe-(NMe-Leu)-Thz-(D-Ser)-Gln-Phe-(D-Ala)-Tic-Ser-OH (Compound YW-121) (SEQ ID NO: 6)

Referring to the synthesis method similar to that of Embodiment 1, Fmoc-Leu was replaced with Fmoc-NMe-Leu (3 equivalent) for condensation, the condensation reaction was performed under HATU/HOAt/DIPEA condition. Fmoc-Pro was replaced with Fmoc-Thz (3 equivalent) for condensation, the condensation reaction was performed under HBTU/HOBt/DIPEA condition, and the condensation and Fmoc deprotection conditions of other residues are consistent with Embodiment 1. The resin was dried after washing. The desired polypeptide was cleaved from the resin by the method of step 2 in Embodiment 1, followed by deprotection. The crude product YW-121 was purified by HPLC, eluted with a linear gradient (10 min) at a flow rate of 25 mL/min. The eluent A/B: 73/27-63/37 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 27.2 mg.

Embodiment 41

Preparation of (D-Tyr)-Phe-(NMe-Leu)-Thz-(D-Ser)-Gln-2Nal-(D-Ala)-Tic-Ser-OH (Compound YW-122) (SEQ ID NO: 7)

Referring to the synthesis method similar to that of Embodiment 40, Fmoc-Phe was replaced with Fmoc-2Nal (3 equivalent) for condensation, and the condensation reaction was performed under HATU/HOAt/DIPEA condition. The resin was dried after washing. The desired polypeptide was cleaved from the resin by the method of step 2 in Embodiment 1, followed by deprotection. The crude product YW-122 was purified by HPLC, eluted with a linear gradient (10 min) at a flow rate of 25 mL/min. The eluent A/B: 70/30-60/40 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 20.4 mg.

Embodiment 42

Preparation of (NMe-D-Tyr)-Phe-(NMe-Leu)-Thz-(D-Ser)-Gln-Phe-(D-Ala)-Tic-(NMe-Ser)-OH (Compound YW-124) (SEQ ID NO: 9)

Referring to the synthesis method similar to that of Embodiment 40, Fmoc-D-Tyr(tBu) was replaced with Fmoc-NMe-D-Tyr(tBu) (3 equivalent) for condensation, and the condensation reaction was performed under HATU/HOAt/DIPEA condition. Fmoc-Ser(tBu) was replaced with Fmoc-NMe-Ser(tBu) (3 equivalent) for condensation, and the condensation reaction was performed under HATU/HOAt/DIPEA condition. The resin was dried after washing. The desired polypeptide was cleaved from the resin by the method of step 2 in Embodiment 1, followed by deprotection. The crude product YW-124 was purified by HPLC, eluted with a linear gradient (10 min) at a flow rate of 25 mL/min. The eluent A/B: 73/27-63/37 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 12.8 mg.

Embodiment 43

Preparation of (D-NMe-Tyr)-Phe-(NMe-Leu)-Thz-(D-Ser)-Gln-2Nal-(D-Ala)-Tic-(NMe-Ser)-OH (Compound YW-125) (SEQ ID NO: 10)

Referring to the synthesis method similar to that of Embodiment 42, Fmoc-Phe was replaced with Fmoc-2Nal (3 equivalent) for condensation, and the condensation reaction was performed under HATU/HOAt/DIPEA condition. The resin was dried after washing. The desired polypeptide was cleaved from the resin by the method of step 2 in Embodiment 1, followed by deprotection. The crude product YW-125 was purified by HPLC, eluted with a linear gradient (10 min) at a flow rate of 25 mL/min. The eluent A/B: 70/30-51/49 was: eluent A: 0.05% solution of TFA in water; eluent B: 0.05% solution of TFA in acetonitrile. The preparative HPLC was performed on Phenomenex Gemini C18, 10 μm, 110 Å column (21.2×250 mm). The fractions containing the product were collected and lyophilized to obtain a white solid in 53.7 mg.

Embodiment 44

Preparation of 3,5-dihydroxybenzoyl-(D-NMe-Tyr)-Phe-(NMe-Leu)-Thz-(D-Ser)-Gln-2Nal-(D-Ala)-Tic-NMeSer-OH (Compound YW-126) (SEQ ID NO: 120)

Referring to the synthesis method similar to that of Embodiment 43, after the sequence was synthesized, the Fmoc protecting group was removed by a conventional method and the obtained resin was swollen with DMF, followed by condensation with 3,5-dihydroxybenzoic acid (3 equivalent). The condensation reaction was performed under HBTU/HOBt/DIPEA condition using DMF as the solvent, and the mixture was reacted at room temperature overnight. The resin was dried after washing. The desired polypeptide was cleaved from the resin by the method of step 2 in Embodiment 1, followed by deprotection. The crude product YW-126 was purified by HPLC, eluted with a linear gradient (10 min) at a flow rate of 25 mL/min. The eluent A/B: 74/26-64/36 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 500 mg.

Embodiment 45

Preparation of 2,3-dihydroxybenzoyl-(D-Tyr)-Phe-Leu-Pro-(D-Ser)-Gln-Phe-(D-Ala)-Tic-Ser-OH (Compound YW-127) (SEQ ID NO: 97)

The resin obtained in step 1 of Embodiment 1 was swollen with DMF, followed by condensation with 2,3-dihydroxybenzoic acid (3 equivalent). The condensation reaction was performed under HATU/HOAt/DIPEA condition using DMF as the solvent, and the mixture was reacted at room temperature overnight. The resin was dried after washing. The desired polypeptide was cleaved from the resin by the method of step 2 in Embodiment 1, followed by deprotection. The crude product YW-127 was purified by HPLC, eluted with a linear gradient (10 min) at a flow rate of 25 mL/min. The eluent A/B: 65/35-55/45 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 4.2 mg.

Embodiment 46

Preparation of 2,6-dihydroxybenzoyl-(D-Tyr)-Phe-Leu-Pro-(D-Ser)-Gln-Phe-(D-Ala)-Tic-Ser-OH (Compound YW-128) (SEQ ID NO: 98)

The resin obtained in step 1 of Embodiment 1 was swollen with DMF, followed by condensation with 2,6-dihydroxybenzoic acid (3 equivalent). The condensation reaction was performed under HATU/HOAt/DIPEA condition using DMF as the solvent, and the mixture was reacted at room temperature overnight. The resin was dried after washing. The desired polypeptide was cleaved from the resin by the method of step 2 in Embodiment 1, followed by deprotection. The crude product YW-128 was purified by HPLC, eluted with a linear gradient (10 min) at a flow rate of 25 mL/min. The eluent A/B: 64/36-54/46 was: eluent A: 0.05% solution of TFA in water; eluent B: 0.05% solution of TFA in acetonitrile. The preparative HPLC was performed on Sunfire C18, 10 μm, 120 Å column (19×250 mm). The fractions containing the product were collected and lyophilized to obtain a white solid in 24.2 mg.

Embodiment 47

Preparation of 2,3,4-Trihydroxybenzoyl-(D-Tyr)-Phe-Leu-Pro-(D-Ser)-Gln-Phe-(D-Ala)-Tic-Ser-OH (Compound YW-129) (SEQ ID NO: 99)

The resin obtained in step 1 of Embodiment 1 was swollen with DMF, followed by condensation with 2,3,4-dihydroxybenzoic acid (3 equivalent). The condensation reaction was performed under HATU/HOAt/DIPEA condition using DMF as the solvent, and the mixture was reacted at room temperature overnight. The resin was dried after washing. The desired polypeptide was cleaved from the resin by the method of step 2 in Embodiment 1, followed by deprotection. The crude product YW-129 was purified by HPLC, eluted with a linear gradient (10 min) at a flow rate of 25 mL/min. The eluent A/B: 65/35-58/42 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 5.9 mg.

Embodiment 48

Preparation of 3,5-dihydroxyphenylacetyl-(D-Tyr)-Phe-Leu-Pro-(D-Ser)-Gln-Phe-(D-Ala)-Tic-Ser-OH (Compound YW-132) (SEQ ID NO: 101)

The resin obtained in step 1 of Embodiment 1 was swollen with DMF, followed by condensation with 3,5-dihydroxyphenyl acetic acid (3 equivalent). The condensation reaction was performed under HATU/HOAt/DIPEA condition using DMF as the solvent, and the mixture was reacted at room temperature overnight. The resin was dried after washing. The desired polypeptide was cleaved from the resin by the method of step 2 in Embodiment 1, followed by deprotection. The crude product YW-132 was purified by HPLC, eluted with a linear gradient (10 min) at a flow rate of 25 mL/min. The eluent A/B: 67/33-57/43 was: eluent A: 0.05% solution of TFA in water; eluent B: 0.05% solution of TFA in acetonitrile. The preparative HPLC was performed on Xtimate C18, 10 µm, 120 Å column (20×250 mm). The fractions containing the product were collected and lyophilized to obtain a white solid in 9.3 mg.

Embodiment 49

Preparation of Palm-PEG8-Gly-Gly-(D-Tyr)-Phe-(NMe-Leu)-Pro-(D-Ser)-Gln-Phe-(D-Ala)-Tic-Ser-OH (Compound YW-133) (SEQ ID NO: 11)

After the sequence was obtained by the synthetic method similar to that of Embodiment 19, the Fmoc protecting group was removed by a conventional method, followed by the introduction of other amino acids (Fmoc-Gly-OH, 2 times), Fmoc-(PEG) 8-OH and a fatty chain (Palmitic acid) into the protected Palm-PEG8-Gly-Gly-(D-Tyr)-Phe-(NMe-Leu)-Pro-(D-Ser)-Gln-Phe-(D-Ala)-Tic-Ser-CTC resin (SEQ ID NO: 11-CTC resin) by a similar method. The desired polypeptide was cleaved from the resin by the method of step 2 in Embodiment 1, followed by deprotection. The crude product YW-133 was purified by HPLC, eluted with a linear gradient (10 min) at a flow rate of 25 mL/min. The eluent A/B: 34/66-27/73 was: eluent A: 0.05% solution of TFA in water; eluent B: 0.05% solution of TFA in acetonitrile. The preparative HPLC was performed on Xtimate C18, 10 µm, 120 Å column (20×250 mm). The fractions containing the product were collected and lyophilized to obtain a white solid in 33.2 mg.

Embodiment 50

Preparation of Palm-PEG8-βAla-βAla-(D-Tyr)-Phe-(NMe-Leu)-Pro-(D-Ser)-Gln-Phe-(D-Ala)-Tic-Ser-OH (Compound YW-134) (SEQ ID NO: 12)

After the sequence was obtained by the synthetic method similar to that of Embodiment 19, the Fmoc protecting group was removed by a conventional method, followed by the introduction of other amino acids (Fmoc-βAla-OH, 2 times), Fmoc-(PEG) 8-OH and a fatty chain (Palmitic acid) into the protected Palm-PEG8-βAla-βAla-(D-Tyr)-Phe-(NMe-Leu)-Pro-(D-Ser)-Gln-Phe-(D-Ala)-Tic-Ser-CTC resin (SEQ ID NO: 12-CTC resin) by a similar method. The desired polypeptide was cleaved from the resin by the method of step 2 in Embodiment 1, followed by deprotection. The crude product YW-134 was purified by HPLC, eluted with a linear gradient (10 min) at a flow rate of 25 mL/min. The eluent A/B: 36/64-26/74 was: eluent A: 0.05% solution of TFA in water; eluent B: 0.05% solution of TFA in acetonitrile. The preparative HPLC was performed on Xtimate C18, 10 µm, 120 Å column (20×250 mm). The fractions containing the product were collected and lyophilized to obtain a white solid in 404.0 mg.

Embodiment 51

Preparation of (D-NMe-Tyr)-Phe-(NMe-Leu)-Thz-(D-Ser)-Gln-1Nal-(D-Ala)-Tic-(NMe-Ser)-OH (Compound YW-142) (SEQ ID NO: 13)

Referring to the synthesis method similar to that of Embodiment 42, Fmoc-Phe was replaced with Fmoc-1Nal (3 equivalent) for condensation, and the condensation reaction was performed under HATU/HOAt/DIPEA condition. The resin was dried after washing. The desired polypeptide was cleaved from the resin by the method of step 2 in Embodiment 1, followed by deprotection. The crude product YW-142 was purified by HPLC, eluted with a linear gradient (10 min) at a flow rate of 45 mL/min. The eluent A/B: 70/30-64/36 was: eluent A: 0.05% solution of TFA in water; eluent B: 0.05% solution of TFA in acetonitrile. The preparative HPLC was performed on Phenomenex Gemini C18, 10 µm, 110 Å column (30×250 mm). The fractions containing the product were collected and lyophilized to obtain a white solid in 22.1 mg.

Embodiment 52

Preparation of (D-NMe-Tyr)-Phe-(NMe-Leu)-Pro-(D-Ser)-Gln-2Nal-(D-Ala)-Tic-(NMe-Ser)-OH (Compound YW-146) (SEQ ID NO: 14)

Referring to the synthesis method similar to that of Embodiment 1, Fmoc-Ser(tBu) was replaced with Fmoc-NMe-Ser(tBu) for condensation and the condensation reaction was performed under HATU/HOAt/DIPEA condition; Fmoc-Phe was replaced with Fmoc-2Nal for condensation and the condensation reaction was performed under HBTU/HOBt/DIPEA condition; Fmoc-Leu was replaced with Fmoc-NMe-Leu for condensation and the condensation reaction was performed under HATU/HOAt/DIPEA condition; Fmoc-D-Tyr (tBu) was replaced with Fmoc-NMe-D-Tyr(tBu) for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-143 was purified by HPLC, eluted with a linear gradient (10 min) at a flow rate of 25 mL/min. The eluent A/B: 72/28-64/36 was: eluent A: 0.05% solution of TFA in water; eluent B: 0.05% solution of TFA in acetonitrile. The preparative HPLC was performed on Sunfire C18, 10 µm, 120 Å column (19×250 mm). The fractions containing the product were collected and lyophilized to obtain a white solid in 28.9 mg.

Embodiment 53

Preparation of (D-Tyr)-Phe-Leu-Pro-(D-Ser)-Gln-(D-Ser)-(D-Ala)-azaTic-Ser-OH (Compound YW-147) (SEQ ID NO: 115)

Step 1: 500 mg of commercially available 2-CTC resin (1.34 mol/g) was swollen in DCM (10 mL) for 30 minutes, followed by addition of Fmoc-D-Ala-azaTic-Ser(tBu)-OH (150 mg, 0.24 mmol) and DIPEA (0.1 mL, 0.72 mmol), and treated at room temperature for 40 minutes. Fmoc-(D-Ala)-azaTic-Ser(tBu)-2-CTC resin was obtained, followed by removal of the solution and addition of DCM/MeOH/DIPEA (20 mL, v/v/v: 85:10:5), and reacted for 30 minutes, and such procedure was repeated twice. The excess CI of 2-CTC was blocked, followed by removal of the solution. The resin was washed with DMF, followed by addition of 20% piperidine/DMF solution (10 mL), and reacted for 15 minutes, and such procedure was repeated twice to remove Fmoc. The resin was washed with DMF, followed by addition of 10 mL of solution of Fmoc-D-Ser(tBu)-OH (383 mg, 0.45 mmol), HBTU (170 mg, 0.45 mmol) and HOBT (60 mg, 0.45 mmol) in DMF, then DIPEA (0.1 ml, 0.45 mmol) was added, and reacted at room temperature for 1 hour to obtain Fmoc-(D-Ser(tBu))-(D-Ala)-azaTic-Ser(tBu)-2-CTC. Other amino acids were introduced in a similar manner to obtain (D-Tyr(tBu))-Phe-Leu-Pro-(D-Ser(tBu))-Gln(Trt)-(D-Ser(tBu))-(D-Ala)-azaTic-Ser(tBu)-2-CTC resin (SEQ ID NO: 125-2-CTC resin). The resin was washed by DCM, methanol and methyl tert-butyl ether, followed by drying.

Step 2: The dried resin was added to 5 mL of TFA/TIS/H$_2$O (95/2.5/2.5) solution, followed by vibration for 2 hours, and the resin was isolated by filtration. The resin was washed with 2 mL of TFA/TIS/H$_2$O (95/2.5/2.5) solution. The filtrate was combined, followed by addition of diethyl ether (70 mL). The obtained precipitate was centrifuged and the supernatant was removed. The obtained precipitate was dissolved in DMF, followed by a linear gradient elution (10 min) at a flow rate of 25 mL/min. The eluent A/B: 75/25-65/35 was: eluent A: 0.05% solution of TFA in water; eluent B: 0.05% solution of TFA in acetonitrile. The preparative HPLC was performed on Phenomenex Gemini, 10 um, 110 Å column (21.2×250 mm). The fractions containing the product were collected and lyophilized to obtain a white solid in 80 mg.

Mass spectrometry [M+H]$^+$: 1159.6. (Calculated value: 1159.2)

Embodiment 54

Preparation of (D-NMe-Tyr)-Phe-(NMe-Leu)-Thz-(D-Ser)-Gln-2Nal-(D-Ala)-Tic-Ser-OH (Compound YW-148) (SEQ ID NO: 15)

Referring to the synthesis method similar to that of Embodiment 41, Fmoc-D-Tyr(tBu) was replaced with Fmoc-NMeD-Tyr(tBu) for condensation, and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-148 was purified by HPLC, eluted with a linear gradient (10 min) at a flow rate of 25 mL/min. The eluent A/B: 70/30-65/35 was: eluent A: 0.05% solution of TFA in water; eluent B: 0.05% solution of TFA in acetonitrile. The preparative HPLC was performed on Sunfire C18, 10 µm, 120 Å column (19×250 mm). The fractions containing the product were collected and lyophilized to obtain a white solid in 14.6 mg.

Embodiment 55

Preparation of (D-Tyr)-Phe-Leu-Pro-(D-Ser)-Gln-Phe-(D-Ala)-D-Tic-Ser-OH (Compound YW-149) (SEQ ID NO: 79)

Referring to the synthesis method similar to that of Embodiment 1, Fmoc-Tic was replaced with Fmoc-D-Tic for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-149 was purified by HPLC, eluted with a linear gradient (10 min) at a flow rate of 25 mL/min. The eluent A/B: 82/18-72/28 was: eluent A: 0.05% solution of TFA in water; eluent B: 0.05% solution of TFA in acetonitrile. The preparative HPLC was performed on Xtimate C18, 10 µm, 120 Å column (20×250 mm). The fractions containing the product were collected and lyophilized to obtain a white solid in 43.0 mg.

Embodiment 56

Preparation of (D-Tyr)-Phe-Leu-Pro-(D-Ser)-Gln-Phe-(D-Ala)-Ti1c-Ser-OH (Compound YW-150) (SEQ ID NO: 80)

Referring to the synthesis method similar to that of Embodiment 1, Fmoc-Tic was replaced with Fmoc-Ti1c for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-150 was purified by HPLC, eluted with a linear gradient (10 min) at a flow rate of 25 mL/min. The eluent A/B: 72/28-62/38 was: eluent A: 0.05% solution of TFA in water; eluent B: 0.05% solution of TFA in acetonitrile. The preparative HPLC was performed on Phenomenex Gmini C18, 10 µm, 110 Å column (21.2×250 mm). The fractions containing the product were collected and lyophilized to obtain a white solid in 31.3 mg.

Embodiment 57

Preparation of (D-Tyr)-Phe-Leu-Pro-(D-Ser)-Gln-Phe-(D-Ala)-D-Ti1c-Ser-OH (Compound YW-151) (SEQ ID NO: 81)

Referring to the synthesis method similar to that of Embodiment 1, Fmoc-Tic was replaced with Fmoc-D-Ti1c for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-151 was purified by HPLC, eluted with a linear gradient (10 min) at a flow rate of 25 mL/min. The eluent A/B: 72/28-64/36 was: eluent A: 0.05% solution of TFA in water; eluent B: 0.05% solution of TFA in acetonitrile. The preparative HPLC was performed on Phenomenex Gmini C18,

Embodiment 58

Preparation of (D-Tyr)-Phe-(NMe-Leu)-Pro-(D-Ser)-Gln-Phe-(D-Ala)-D-Ti1c-Ser-OH (Compound YW-153) (SEQ ID NO: 16)

Referring to the synthesis method similar to that of Embodiment 1, Fmoc-Tic was replaced with Fmoc-D-Ti1c for condensation and the condensation reaction was performed under HATU/HOAt/DIPEA condition; Fmoc-Leu was replaced with Fmoc-NMeLeu for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-153 was purified by HPLC, eluted with a linear gradient (10 min) at a flow rate of 25 mL/min. The eluent A/B: 73/27-67/33 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 35.0 mg.

Embodiment 59

Preparation of (D-NMe-Tyr)-Phe-Leu-Pro-(D-Ser)-Gln-Phe-(D-Ala)-D-Ti1c-Ser-OH (Compound YW-154) (SEQ ID NO: 82)

Referring to the synthesis method similar to that of Embodiment 1, Fmoc-Tic was replaced with Fmoc-D-Ti1c for condensation and the condensation reaction was performed under HATU/HOAt/DIPEA condition; Fmoc-D-Tyr (tBu) was replaced with Fmoc-NMe-D-Tyr(tBu) for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-154 was purified by HPLC, eluted with a linear gradient (10 min) at a flow rate of 25 mL/min. The eluent A/B: 72/28-66/34 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 57.3 mg.

Embodiment 60

Preparation of (D-Tyr)-Phe-Leu-Pro-(D-Ser)-Gln-Phe-(D-Ala)-D-Ti1c-(NMe-Ser)-OH (Compound YW-155) (SEQ ID NO: 116)

Referring to the synthesis method similar to that of Embodiment 1, Fmoc-Ser(tBu) was replaced with Fmoc-NMe-Ser(tBu) for condensation and the condensation reaction was performed under HATU/HOAt/DIPEA condition; Fmoc-Tic was replaced with Fmoc-D-Ti1c for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-155 was purified by HPLC, eluted with a linear gradient (10 min) at a flow rate of 25 mL/min. The eluent A/B: 72/28-66/34 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 5.3 mg.

Embodiment 61

Preparation of (D-Tyr)-Phe-Leu-Pro-(D-Ser)-Gln-2Nal-(D-Ala)-D-Ti1c-Ser-OH (Compound YW-156) (SEQ ID NO: 117)

Referring to the synthesis method similar to that of Embodiment 1, Fmoc-Tic was replaced with Fmoc-D-Ti1c for condensation and the condensation reaction was performed under HATU/HOAt/DIPEA condition; Fmoc-Phe was replaced with Fmoc-2Nal for condensation and the condensation reaction was performed under HBTU/HOBt/DIPEA condition. The Fmoc protecting group was removed by a conventional method and the resin was dried after washing. The desired polypeptide was cleaved from the resin by the method of step 2 in Embodiment 1, followed by deprotection. The crude product YW-156 was purified by HPLC, eluted with a linear gradient (10 min) at a flow rate of 25 mL/min. The eluent A/B: 63/37-57/43 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 22.9 mg.

Embodiment 62

Preparation of (D-Tyr)-Phe-Leu-Pro-(D-Ser)-Gln-1Nal-(D-Ala)-D-Ti1c-Ser-OH (Compound YW-157) (SEQ ID NO: 118)

Referring to the synthesis method similar to that of Embodiment 1, Fmoc-Tic was replaced with Fmoc-D-Ti1c for condensation and the condensation reaction was performed under HATU/HOAt/DIPEA condition; Fmoc-Phe was replaced with Fmoc-1Nal for condensation and the condensation reaction was performed under HBTU/HOBt/DIPEA condition. The Fmoc protecting group was removed by a conventional method and the resin was dried after washing. The desired polypeptide was cleaved from the resin by the method of step 2 in Embodiment 1, followed by deprotection. The crude product YW-157 was purified by HPLC, eluted with a linear gradient (10 min) at a flow rate of 25 mL/min. The eluent A/B: 63/37-57/43 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 41.4 mg.

Embodiment 63

Preparation of (D-Tyr)-Phe-Leu-Pro-(D-Ser)-Gln-Phe-(D-Ala)-TP5C-Ser-OH (Compound YW-158) (SEQ ID NO: 83)

Referring to the synthesis method similar to that of Embodiment 1, Fmoc-Tic was replaced with Fmoc-TP5C for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-158 was purified by HPLC, eluted with a linear gradient (10 min) at a flow rate of 25 mL/min. The eluent A/B: 70/30-64/36 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 18.6 mg.

Embodiment 64

Preparation of (D-Tyr)-Phe-Leu-Pro-(D-Ser)-Gln-Phe-(D-Ala)-TP6C-Ser-OH (Compound YW-159) (SEQ ID NO: 84)

Referring to the synthesis method similar to that of Embodiment 1, Fmoc-Tic was replaced with Fmoc-TP6C for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-159 was purified by HPLC, eluted with a linear gradient (10 min) at a flow rate of 25 mL/min. The eluent A/B: 70/30-64/36 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 25.8 mg.

Embodiment 65

Preparation of (D-Tyr)-Phe-Leu-Pro-(D-Ser)-Gln-Phe-(D-Ala)-Tic-Thr-OH (Compound YW-160) (SEQ ID NO: 119)

Referring to the synthesis method similar to that of Embodiment 1, Fmoc-Ser(tBu) was replaced with Fmoc-Thr(tBu) for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-160 was purified by HPLC, eluted with a linear gradient (10 min) at a flow rate of 25 mL/min. The eluent A/B: 69/31-59/41 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 20.4 mg.

Embodiment 66

Preparation of 3-phenylpropanoyl-(D-Tyr)-Phe-(NMe-Leu)-Pro-(D-Ser)-Gln-Phe-(D-Ala)-Tic-Ser-NH₂ (Compound YW-161) (SEQ ID NO: 17)

Step 1: The polypeptide was synthesized by standard Fmoc chemistry, and the basic procedure is as follows. 200 mg of commercially available Rink Amide MBHA resin (0.5 mol/g) was swollen in DCM, and the resin was treated with 5 mL of 20% piperidine/DMF solution to remove Fmoc, and such procedure was repeated twice. The obtained resin was washed with DMF, followed by addition of 20 mL of solution of Fmoc-Ser(tBu)-OH (116 mg, 0.3 mmol), HBTU (114 mg, 0.3 mmol) and HOBt (41 mg, 0.3 mmol) in DMF, then DIPEA (77 mg, 0.6 mmol) was added, and treated at room temperature for 40 minutes, followed by introduction of Ser(tBu) to obtain Fmoc-Ser(tBu)-MBHA resin. Other amino acids were introduced in a similar manner to obtain Fmoc-(D-Tyr(tBu))-Phe-(NMe-Leu)-Pro-(D-Ser(tBu))-Gln-Phe-(D-Ala)-Tic-Ser(tBu)-MBHA resin. The resin was treated with 20% piperidine/DMF for 20 minutes to remove Fmoc, and such procedure was repeated twice. The obtained resin was washed with DMF, followed by addition of 10 mL of solution of 3-phenylpropanoic acid (45 mg, 0.3 mmol), HBTU (114 mg, 0.3 mmol) and HOBt (41 mg, 0.3 mmol) in DMF, then DIPEA (77 mg, 0.6 mmol) was added, and treated at room temperature for 4 hours to obtain 3-phenylpropanoyl-(D-Tyr(tBu))-Phe-(NMe-Leu)-Pro-(D-Ser(tBu))-Gln-Phe-(D-Ala)-Tic-Ser(tBu)-MBHA resin.

Step 2: The dried resin was added to 5 mL of TFA/TIS/H₂O (95/2.5/2.5) solution, followed by vibration for 2 hours, and the resin was isolated by filtration. The resin was washed with 2 mL of TFA/TIS/H₂O (95/2.5/2.5) solution. The filtrate was combined, followed by addition of diethyl ether (70 mL). The obtained precipitate was centrifuged and the supernatant was removed. The obtained precipitate was dissolved in DMF and purified by HPLC, followed by a linear gradient elution (10 min) at a flow rate of 25 mL/min. The eluent A/B: 59/41-49/51 was: eluent A: 0.05% solution of TFA in water; eluent B: 0.05% solution of TFA in acetonitrile. The preparative HPLC was performed on Xtimate C18, 5 μm, 120 Å column (20×250 mm). The fractions containing the product were collected and lyophilized to obtain a white solid in 32.7 mg.

Embodiment 67

Preparation of (D-NMe-Tyr)-Phe-(NMe-Leu)-Pro-(D-Ser)-Gln-1Nal-(D-Ala)-Tic-NMeSer-OH (Compound YW-162) (SEQ ID NO: 18)

Referring to the synthesis method similar to that of Embodiment 1, Fmoc-Ser(tBu) was replaced with Fmoc-NMe-Ser(tBu) for condensation and the condensation reaction was performed under HATU/HOAt/DIPEA condition; Fmoc-Phe was replaced with Fmoc-1Nal for condensation and the condensation reaction was performed under HBTU/HOBt/DIPEA condition; Fmoc-Leu was replaced with Fmoc-NMe-Leu for condensation and the condensation reaction was performed under HATU/HOAt/DIPEA condition; Fmoc-D-Tyr (tBu) was replaced with Fmoc-NMeD-Tyr(tBu) for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-162 was purified by HPLC, eluted with a linear gradient (10 min) at a flow rate of 25 mL/min. The eluent A/B: 67/33-61/39 was: eluent A: 0.05% solution of TFA in water; eluent B: 0.05% solution of TFA in acetonitrile. The preparative HPLC was performed on Xtimate C18,

Embodiment 68

Preparation of (D-NMe-Tyr)-Phe-(NMe-Leu)-Pro-(D-Ser)-Gln-Phe-(D-Ala)-Tic-Ser-OH (Compound YW-163) (SEQ ID NO: 19)

Referring to the synthesis method similar to that of Embodiment 1, Fmoc-Leu was replaced with Fmoc-NMe-Leu for condensation and the condensation reaction was performed under HATU/HOAt/DIPEA condition; Fmoc-D-Tyr (tBu) was replaced with Fmoc-NMeD-Tyr(tBu) for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-163 was purified by HPLC, eluted with a linear gradient (10 min) at a flow rate of 25 mL/min. The eluent A/B: 73/27-63/37 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 56.8 mg.

Embodiment 69

Preparation of (D-Tyr)-Phe-(NMe-Leu)-Pro-(D-Ser)-Gln-2Nal-(D-Ala)-Tic-Ser-OH (Compound YW-164) (SEQ ID NO: 20)

Referring to the synthesis method similar to that of Embodiment 1, Fmoc-Phe was replaced with Fmoc-2Nal for condensation and the condensation reaction was performed under HBTU/HOBt/DIPEA condition; Fmoc-Leu was replaced with Fmoc-NMe-Leu for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-164 was purified by HPLC, eluted with a linear gradient (10 min) at a flow rate of 25 mL/min. The eluent A/B: 70/30-60/40 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 73.5 mg.

Embodiment 70

Preparation of (D-Tyr)-Phe-(NMe-Leu)-Pro-(D-Ser)-Gln-1Nal-(D-Ala)-Tic-Ser-OH (Compound YW-165) (SEQ ID NO: 21)

Referring to the synthesis method similar to that of Embodiment 1, Fmoc-Phe was replaced with Fmoc-1Nal for condensation and the condensation reaction was performed under HBTU/HOBt/DIPEA condition; Fmoc-Leu was replaced with Fmoc-NMe-Leu for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-165 was purified by HPLC, eluted with a linear gradient (10 min) at a flow rate of 25 mL/min. The eluent A/B: 71/29-61/39 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 55.6 mg.

Embodiment 71

Preparation of (D-Tyr)-Phe-(NMe-Leu)-Pro-(D-Ser)-Gln-Phe-(D-Ala)-Tic-(NMe-Ser)-OH (Compound YW-166) (SEQ ID NO: 22)

Referring to the synthesis method similar to that of Embodiment 1, Fmoc-Ser(tBu) was replaced with Fmoc-NMe-Ser(tBu) for condensation and the condensation reaction was performed under HATU/HOAt/DIPEA condition; Fmoc-Leu was replaced with Fmoc-NMe-Leu for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-166 was purified by HPLC, eluted with a linear gradient (10 min) at a flow rate of 25 mL/min. The eluent A/B: 75/25-65/35 was: eluent A: 0.05% solution of TFA in water; eluent B: 0.05% solution of TFA in acetonitrile. The preparative HPLC was performed on Sunfire C18, 10 μm, 120 Å column (19×250 mm). The fractions containing the product were collected and lyophilized to obtain a white solid in 18.8 mg.

Embodiment 72

Preparation of (D-NMe-Tyr)-Phe-(NMe-Leu)-Pro-(D-Ser)-Gln-2Nal-(D-Ala)-Tic-Ser-OH (Compound YW-167) (SEQ ID NO: 23)

Referring to the synthesis method similar to that of Embodiment 1, Fmoc-Phe was replaced with Fmoc-2Nal for condensation and the condensation reaction was performed under HBTU/HOBt/DIPEA condition; Fmoc-Leu was replaced with Fmoc-NMe-Leu for condensation and the condensation reaction was performed under HATU/HOAt/DIPEA condition; Fmoc-D-Tyr (tBu) was replaced with Fmoc-D-NMe-Tyr(tBu) for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-167 was purified by HPLC, eluted with a linear gradient (10 min) at a flow rate of 25 mL/min. The eluent A/B: 69/31-63/37 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 42.7 mg.

Embodiment 73

Preparation of (D-NMe-Tyr)-Phe-(NMe-Leu)-Pro-(D-Ser)-Gln-1Nal-(D-Ala)-Tic-Ser-OH (Compound YW-168) (SEQ ID NO: 24)

Referring to the synthesis method similar to that of Embodiment 1, Fmoc-Phe was replaced with Fmoc-1Nal for condensation and the condensation reaction was performed under HBTU/HOBt/DIPEA condition; Fmoc-Leu was replaced with Fmoc-NMe-Leu for condensation and the condensation reaction was performed under HATU/HOAt/DIPEA condition; Fmoc-D-Tyr (tBu) was replaced with Fmoc-D-NMe-Tyr(tBu) for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-168 was purified by HPLC, eluted with a linear gradient (10 min) at a flow rate of 25 mL/min. The eluent A/B: 69/31-63/37 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 47.4 mg.

Embodiment 74

Preparation of (D-Tyr)-Phe-(NMe-Leu)-Pro-(D-Ser)-Gln-Phe-(D-Ala)-Tic-HoSer-OH (Compound YW-171) (SEQ ID NO: 25)

Referring to the synthesis method similar to that of Embodiment 1, Fmoc-Ser(tBu) was replaced with Fmoc-HoSer(tBu) for condensation and the condensation reaction was performed under HBTU/HOBt/DIPEA condition; Fmoc-Leu was replaced with Fmoc-NMe-Leu for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-171 was purified and isolated by HPLC.

Embodiment 75

Preparation of (D-Tyr)-Phe-(NMe-Leu)-Pro-(D-Ser)-Gln-Phe-(D-Ala)-Tic-NHoSer-OH (Compound YW-172) (SEQ ID NO: 26)

Step 1: 500 mg of commercially available 2-CTC resin (1.34 mol/g) was swollen in DCM (5 mL) for 30 minutes, followed by addition of Fmoc-NHoSer(tBu)-OH (80 mg, 0.2 mmol) and DIPEA (0.1 ml, 0.75 mmol), and treated at room temperature for 40 minutes. Fmoc-NHoSer(tBu)-2-CTC resin was obtained, followed by removal of the solution and addition of DCM/MeOH/DIPEA (5 mL, v/v/v: 85:10:5), and reacted for 30 minutes, and such procedure was repeated twice. The excess Cl of 2-CTC was blocked, followed by removal of the solution. The resin was washed with DMF, followed by addition of 20% piperidine/DMF solution (5 mL), and reacted for 20 minutes, and such procedure was repeated twice to remove Fmoc.

Step 2: The resin was washed with DMF, followed by addition of 5 mL of solution of Fmoc-Tic-OH (240 mg, 0.60 mmol), HATU (228 mg, 0.60 mmol) and HOAT (82 mg, 0.60 mmol) in DMF, then DIPEA (0.1 ml, 0.75 mmol) was added, and reacted at room temperature for 2 hours to obtain Fmoc-Tic-NHoSer(tBu)-2-CTC. Other amino acids were introduced in a similar manner to obtain (D-Tyr(tBu))-Phe-(NMe-Leu)-Pro-(D-Ser(tBu))-Gln-Phe-(D-Ala)-Tic-NHoSer(tBu)-2-CTC resin (SEQ ID NO: 126-2-CTC resin). The resin was washed by DCM, methanol and methyl tert-butyl ether, followed by drying.

Step 3: The dried resin was added to 5 mL of TFA/TIS/$H_2O$ (90/5/5) solution, followed by vibration for 2 hours, and the resin was isolated by filtration. The resin was washed with 2 mL of TFA/TIS/$H_2O$ (90/5/5) solution. The filtrate was combined, followed by addition of diethyl ether (70 mL). The obtained mixture was centrifuged at 3000 rpm for 1 minute and the supernatant was removed. The obtained precipitate was dissolved in DMF, followed by a linear gradient elution (10 min) at a flow rate of 25 mL/min. The eluent A/B: 69/31-59/41 was: eluent A: 0.05% solution of TFA in water; eluent B: 0.05% solution of TFA in acetonitrile. The preparative HPLC was performed on Phenomenex Gemini 10 μm, 110 Å column (21.2×250 mm). The fractions containing the product were collected and lyophilized to obtain a white solid in 21 mg.

Mass spectrometry $[M+H]^+$: 1246.6. (Calculated value: 1246.6)

Embodiment 77

Preparation of (D-Tyr)-Phe-(NMe-Leu)-Pro(diF)-(D-Ser)-Gln-Phe-(D-Ala)-Tic-Ser-OH (Compound YW-174) (SEQ ID NO: 27)

Referring to the synthesis method similar to that of Embodiment 1, Fmoc-Pro was replaced with Fmoc-Pr(diF) for condensation and the condensation reaction was performed under HBTU/HOBt/DIPEA condition; Fmoc-Leu was replaced with Fmoc-NMe-Leu for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-174 was purified by HPLC, eluted with a linear gradient (10 min) at a flow rate of 25 mL/min. The eluent A/B: 70/30-64/36 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 26.1 mg.

Embodiment 78

Preparation of (D-Tyr)-Phe-(NMe-Leu)-Pro-(D-HoSer)-Gln-Phe-(D-Ala)-Tic-Ser-OH (Compound YW-175) (SEQ ID NO: 28)

Referring to the synthesis method similar to that of Embodiment 1, Fmoc-D-Ser(tBu) was replaced with Fmoc-D-HoSer(tBu) for condensation and the condensation reaction was performed under HATU/HOAt/DIPEA condition; Fmoc-Leu was replaced with Fmoc-NMeLeu for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-175 was purified by HPLC, eluted with a linear gradient (10 min) at a flow rate of 25 mL/min. The eluent A/B: 73/27-67/33 was: eluent A: 0.05% solution of TFA in water; eluent B: 0.05% solution of TFA in acetonitrile. The preparative HPLC was performed on Sunfire C18, 10 μm, 120 Å column (19×250 mm). The fractions containing the product were collected and lyophilized to obtain a white solid in 47.8 mg.

Embodiment 79

Preparation of (D-Tyr)-Phe-(NMe-Leu)-Pro-(D-Ser)-Gln-Phe-(D-Ala)-(D-Oic)-Ser-OH (Compound YW-176) (SEQ ID NO: 29)

Referring to the synthesis method similar to that of Embodiment 1, Fmoc-D-Tic was replaced with Fmoc-D-Oic for condensation and the condensation reaction was performed under HATU/HOAt/DIPEA condition; Fmoc-Leu was replaced with Fmoc-NMe-Leu for condensation and the condensation reaction was performed under HATU/HOAt/DIPEA condition. The Fmoc protecting group was removed by a conventional method and the resin was dried after washing. The desired polypeptide was cleaved from the resin by the method of step 2 in Embodiment 1, followed by deprotection. The crude product YW-176 was purified by HPLC, eluted with a linear gradient (10 min) at a flow rate of 25 mL/min. The eluent A/B: 72/28-66/34 was: eluent A: 0.05% solution of TFA in water; eluent B: 0.05% solution of TFA in acetonitrile. The preparative HPLC was performed on Xtimate C18, 10 μm, 120 Å column (20×250 mm). The fractions containing the product were collected and lyophilized to obtain a white solid in 28.4 mg.

Embodiment 80

Preparation of (D-Tyr)-Phe-(NMe-Leu)-Pro-(D-Ser)-Gln-Phe-(D-Ala)-Tic-(NMe-HoSer)-OH (Compound YW-177) (SEQ ID NO: 30)

The HoSer(tBu)-2-CT resin obtained by the step 1 of Embodiment 5 was washed with DMF, followed by addition of 5 mL of solution of p-nitrobenzenesulfonyl chloride (111 mg, 0.5 mmol) in DMF, and then DIPEA (0.2 ml, 1.5 mmol) was added and reacted at room temperature for 3 hours. The resin was washed with DMF, followed by addition of DMF (5 mL) and addition of triphenylphosphine (131 mg, 0.5 mmol), DIAD (201 mg, 0.5 mmol) and methanol (0.5 mL), and reacted at room temperature under nitrogen atmosphere for 3 hours. The resin was washed with DMF, followed by addition of thiophenol (0.55 g, 5.0 mmol), DMF (5 mL) and DIPEA (0.95 g, 7.5 mmol), and the reaction was carried out at room temperature for 1 hour to remove p-nitrophenylsulfonyl group, and the resin was washed with DMF. NH$_2$-NMe-HoSer(tBu)-2-CTC resin was obtained, followed by addition of 5 mL of solution of Fmoc-Tic-OH (240 mg, 0.60 mmol), HATU (228 mg, 0.60 mmol) and HOAT (82 mg, 0.60 mmol) in DMF, and then DIPEA (0.1 ml, 0.75 mmol) was added and reacted at room temperature for 2 hours. The resin was washed with DMF to obtain Fmoc-Tic-NMe-HoSer(tBu)-2-CTC. Other amino acids were introduced in a similar manner to obtain (D-Tyr(tBu))-Phe-(NMe-Leu)-Pro-(D-Ser(tBu))-Gln-Phe-(D-Ala)-Tic-(NMe-HoSer(tBu))-2-CTC resin (SEQ ID NO: 127-2-CTC resin). The resin was washed with DMF, DCM, methanol, methyl tert-butyl ether, followed by drying.

Step 2: The dried resin was added to 5 mL of TFA/TIS/H$_2$O (90/5/5) solution, followed by vibration for 2 hours, and the resin was isolated by filtration. The resin was washed with 2 mL of TFA/TIS/H$_2$O (90/5/5) solution. The filtrate was combined, followed by addition of diethyl ether (70 mL). The obtained mixture was centrifuged at 3000 rpm for 1 minute and the supernatant was removed. The obtained precipitate was dissolved in DMF, followed by a linear gradient elution (10 min) at a flow rate of 25 mL/min. The eluent A/B: 75/25-67/33 was: eluent A: 0.05% solution of TFA in water; eluent B: 0.05% solution of TFA in acetonitrile. The preparative HPLC was performed on Phenomenex Gemini, 10 μm, 110 Å column (21.2×250 mm). The fractions containing the product were collected and lyophilized to obtain 13 mg of γ-butyrolactone product as a white solid.

Step 3: γ-butyrolactone product (13 mg) obtained above was dissolved in tetrahydrofuran (0.5 mL), followed by addition of 0.1 N NaOH solution (0.5 mL). The reaction was carried out at room temperature under ultrasonic wave for 1 hour. The reaction solution was added to DMF (1 mL), followed by a linear gradient elution (10 min) at a flow rate of 25 mL/min. The eluent A/B: 67/33-61/39 was: eluent A: 0.05% solution of TFA in water; eluent B: 0.05% solution of TFA in acetonitrile. The preparative HPLC was performed on Xtimate, 10 μm, 110 Å column (20×250 mm). The fractions containing the product were collected and lyophilized to obtain a white solid in 6.8 mg.

Mass spectrometry [M+H]$^+$: 1260.6 (Calculated value: 1260.6)

Embodiment 80

Preparation of Palm-PEG8-(beta-Ala)-(beta-Ala)-(D-NMeTyr)-Phe-(NMe-Leu)-Pro-(D-Ser)-Gln-2Nal-(D-Ala)-Tic-(NMe-Ser) (Compound YW-179) (SEQ ID NO: 32)

1.0 g of commercially available CTC resin was swollen in DMF, followed by addition of solution of Fmoc-[NMe-Ser(tBu)]—OH (119 mg, 0.3 mmol) in 10 mL of DMF and addition of DIPEA (155 mg, 1.2 mmol), and treated at room temperature for 16 hours. The resin was washed with DMF, and blocked with the solution of methanol (320 mg, 10 mmol) and DIPEA (310 mg, 2.4 mmol) in 10 mL of DMF. The resin was washed with DMF to obtain Fmoc-[NMe-Ser(tBu)]-CTC resin. The resin was treated with 10 mL of 20% piperidine/DMF solution for 20 minutes to remove Fmoc, and such procedure was repeated twice. The resin was washed with DMF, followed by addition of 10 mL of solution of Fmoc-Tic-OH (359 mg, 0.9 mmol), HATU (342 mg, 0.9 mmol) and HOAt (122 mg, 0.9 mmol) in 10 mL of DMF and addition of DIPEA (232 mg, 1.8 mmol), and treated at room temperature for 40 minutes. The resin was washed with DMF to obtain Fmoc-Tic-[NMe-Ser(tBu)]-CTC resin. Other amino acids, such as D-Ala, 2Nal, Gln (Trt), D-Ser(tBu), Pro, NMe-Leu, Phe, D-NMeTyr(tBu), βAla, βAla, PEG8 and Palm, were successively introduced in a similar manner to obtain 1.6 g of CTC resin of the desired polypeptide. The resin was washed with DMF, methanol, methyl tert-butyl ether, and then dried.

The dried resin was added to 10 mL of TFA/TIS/H$_2$O (92/4/4) solution, and stirred for 2 hours, and the resin was isolated by filtration. The resin was washed with 1 mL of TFA/TIS/H$_2$O (92/4/4) solution. The filtrate was combined, followed by addition of methyl tert-butyl ether (110 mL).

The obtained mixture was centrifuged at 3000 rpm for 1 minute and the solid was washed with cold diethyl ether twice, followed by drying. The obtained precipitate was dissolved in DMF, followed by a linear gradient elution (10 min) at a flow rate of 25 mL/min. The eluent A/B: 25/75-15/85 was: eluent A: 0.05% solution of TFA in water; eluent B: 0.05% solution of TFA in acetonitrile. The preparative HPLC was performed on Xtimate, 10 µm, 120 Å column (20×250 mm). The fractions containing the product were collected and lyophilized to obtain a white solid in 47.9 mg.

Mass spectrometry [M/2+H]$^+$: 1058.1

Embodiment 81

Preparation of (D-Tyr)-Phe-(NEt-Leu)-Pro-(D-Ser)-Gln-Phe-(D-Ala)-Tic-Ser (Compound YW-183) (SEQ ID NO: 36)

1.0 g of commercially available CTC resin was swollen in DMF, followed by addition of solution of Fmoc-Ser(tBu)-OH (115 mg, 0.3 mmol) in 10 mL of DMF and addition of DIPEA (155 mg, 1.2 mmol), and treated at room temperature for 16 hours. The resin was washed with DMF, and blocked with the solution of methanol (320 mg, 10 mmol) and DIPEA (310 mg, 2.4 mmol) in 10 mL of DMF. The resin was washed with DMF to obtain Fmoc-Ser(tBu)-CTC resin. The resin was treated with 10 mL of 20% piperidine/DMF solution for 20 minutes to remove Fmoc, and such procedure was repeated twice. The resin was washed with DMF, followed by addition of 10 mL of solution of Fmoc-Tic-OH (359 mg, 0.9 mmol), HATU (342 mg, 0.9 mmol) and HOAt (122 mg, 0.9 mmol) in 10 mL of DMF and addition of DIPEA (232 mg, 1.8 mmol), and treated at room temperature for 40 minutes. The resin was washed with DMF to obtain Fmoc-Tic-Ser(tBu)-CTC resin. Other amino acids, such as D-Ala, Phe, Gln(Trt), D-Ser(tBu), Pro, NEt-Leu, Phe and D-Tyr(tBu), were successively introduced in a similar manner to obtain 1.5 g of D-Tyr(tBu)-Phe-(NEt-Leu)-Pro-[D-Ser(tBu)]-Gln(Trt)-Phe-(D-Ala)-Tic-Ser(tBu)-CTC resin (SEQ ID NO: 128-CTC resin). The resin was washed with DMF, methanol, methyl tert-butyl ether, and then dried.

The dried resin was added to 10 mL of TFA/TIS/H$_2$O (92/4/4) solution, and stirred for 2 hours, and the resin was isolated by filtration. The resin was washed with 1 mL of TFA/TIS/H$_2$O (92/4/4) solution. The filtrate was combined, followed by addition of methyl tert-butyl ether (110 mL). The obtained mixture was centrifuged at 3000 rpm for 1 minute and the solid was washed with cold diethyl ether twice, followed by drying. The obtained precipitate was dissolved in DMF, followed by a linear gradient elution (10 min) at a flow rate of 25 mL/min. The eluent A/B: 72/28-66/34 was: eluent A: 0.05% solution of TFA in water; eluent B: 0.05% solution of TFA in acetonitrile. The preparative HPLC was performed on Sunfire, 10 µm, 110 Å column (19×250 mm). The fractions containing the product were collected and lyophilized to obtain a white solid in 18.8 mg.

Mass spectrometry [M+H]$^+$: 1246.6

Embodiment 82

Preparation of (D-Tyr)-Phe-Leu-Pro-(D-Ser)-Gln-Phe-(D-Ala)-Tic-Ser-NH$_2$ (Compound YW-189) (SEQ ID NO: 85)

Referring to the synthesis method similar to that of Embodiment 66, the resin was synthesized on a MBHA resin by a conventional solid-phase synthesis method. The Fmoc protecting group was removed by a conventional method and the resin was dried after washing. The desired polypeptide was cleaved from the resin by the method of step 2 in Embodiment 66, followed by deprotection. The crude product YW-189 was purified by HPLC, eluted with a linear gradient (10 min) at a flow rate of 25 mL/min. The eluent A/B: 72/28-66/34 was: eluent A: 0.05% solution of TFA in water; eluent B: 0.05% solution of TFA in acetonitrile. The preparative HPLC was performed on Sunfire C18, 10 µm, 120 Å column (19×250 mm). The fractions containing the product were collected and lyophilized to obtain a white solid in 31.5 mg.

Embodiment 83

Preparation of (D-Tyr)-Phe-(NMe-Leu)-Pro-(D-Ser)-Gln-Phe-(D-Ala)-Tic-Ser-NH$_2$ (Compound YW-190) (SEQ ID NO: 40)

Referring to the synthesis method similar to that of Embodiment 66, the resin was synthesized on a MBHA resin by a conventional solid-phase synthesis method. The Fmoc protecting group was removed by a conventional method and the resin was dried after washing. The desired polypeptide was cleaved from the resin by the method of step 2 in Embodiment 66, followed by deprotection. The crude product YW-190 was purified by HPLC, eluted with a linear gradient (10 min) at a flow rate of 25 mL/min. The eluent A/B: 74/26-68/32 was: eluent A: 0.05% solution of TFA in water; eluent B: 0.05% solution of TFA in acetonitrile. The preparative HPLC was performed on Sunfire C18, 10 µm, 120 Å column (19×250 mm). The fractions containing the product were collected and lyophilized to obtain a white solid in 62.8 mg.

Embodiment 84

Preparation of 4-(trifluoromethyl)benzoyl-(D-Tyr)-Phe-(NMe-Leu)-Pro-(D-Ser)-Gln-Phe-(D-Ala)-Tic-Ser (Compound YW-195) (SEQ ID NO: 44)

1.0 g of commercially available CTC resin was swollen in DCM, followed by addition of solution of Fmoc-Ser(tBu)-OH (115 mg, 0.3 mmol) in 10 mL of DMF and addition of DIPEA (155 mg, 1.2 mmol), and treated at room temperature for 16 hours. The resin was washed with DMF, and blocked with the solution of methanol (320 mg, 10 mmol) and DIPEA (310 mg, 2.4 mmol) in 10 mL of DMF. The resin was washed with DMF to obtain Fmoc-Ser(tBu)-CTC resin. The resin was treated with 10 mL of 20% piperidine/DMF solution for 20 minutes to remove Fmoc, and such procedure was repeated twice. The resin was washed with DMF, followed by addition of 10 mL of solution of Fmoc-Tic-OH (359 mg, 0.9 mmol), HATU (342 mg, 0.9 mmol) and HOAt (122 mg, 0.9 mmol) in 10 mL of DMF and addition of DIPEA (232 mg, 1.8 mmol), and treated at room temperature for 40 minutes. The resin was washed with DMF to obtain Fmoc-Tic-Ser(tBu)-CTC resin. Other amino acids, such as D-Ala, Phe, Gln(Trt), D-Ser(tBu), Pro, NMe-Leu, Phe, D-Tyr(tBu) and 4-(trifluoromethyl)benzoic acid, were successively introduced in a similar manner to obtain 1.5 g of CTC resin of the desired polypeptide. The resin was washed with DMF, methanol, methyl tert-butyl ether, and then dried.

The dried resin was added to 10 mL of TFA/TIS/H$_2$O (92/4/4) solution, and stirred for 2 hours, and the resin was isolated by filtration. The resin was washed with 1 mL of TFA/TIS/H$_2$O (92/4/4) solution. The filtrate was combined, followed by addition of methyl tert-butyl ether (110 mL). The obtained mixture was centrifuged at 3000 rpm for 1 minute and the solid was washed with cold diethyl ether twice, followed by drying. The obtained precipitate was dissolved in DMF, followed by a linear gradient elution (10 min) at a flow rate of 25 mL/min. The eluent A/B: 72/28-66/34 was: eluent A: 0.05% solution of TFA in water; eluent B: 0.05% solution of TFA in acetonitrile. The preparative HPLC was performed on Xtimate, 10 μm, 120 Å column (20×250 mm). The fractions containing the product were collected and lyophilized to obtain a white solid in 27.6 mg.

Mass spectrometry [M+H]$^+$: 1404.6

Embodiment 85

Preparation of (3-phenyl propyl)-(D-Tyr)-Phe-(NMe-Leu)-Pro-(D-Ser)-Gln-Phe-(D-Ala)-Tic-Ser (Compound YW-207) (SEQ ID NO: 54)

1.2 g of commercially available CTC resin was swollen in DMF, followed by addition of solution of Fmoc-Ser(tBu)-OH (153 mg, 0.4 mmol) in 10 mL of DMF and addition of DIPEA (207 mg, 1.6 mmol), and treated at room temperature for 16 hours. The resin was washed with DMF, and blocked with the solution of methanol (384 mg, 12 mmol) and DIPEA (413 mg, 3.2 mmol) in 10 mL of DMF. The resin was washed with DMF to obtain Fmoc-Ser(tBu)-CTC resin. The resin was treated with 10 mL of 20% piperidine/DMF solution for 20 minutes to remove Fmoc, and such procedure was repeated twice. The resin was washed with DMF, followed by addition of 10 mL of solution of Fmoc-Tic-OH (479 mg, 1.2 mmol), HATU (456 mg, 1.2 mmol) and HOAt (163 mg, 1.2 mmol) in 10 mL of DMF and addition of DIPEA (310 mg, 2.4 mmol), and treated at room temperature for 40 minutes. The resin was washed with DMF to obtain Fmoc-Tic-Ser(tBu)-CTC resin. Other amino acids, such as D-Ala, Phe, Gln(Trt), D-Ser(tBu), Pro, NMe-Leu, Phe and D-Tyr(tBu), were successively introduced in a similar manner to obtain D-Tyr(tBu)-Phe-(NMe-Leu)-Pro-[D-Ser(tBu)]-Gln(Trt)-Phe-(D-Ala)-Tic-Ser(tBu)-CTC resin (SEQ ID NO: 129-CTC resin). The obtained resin was swollen in 10 mL of DMF, followed by addition of 3-phenylpropanal (536 mg, 4.0 mmol) and 2 drops of glacial acetic acid, and treated at room temperature for 2 hours. The resin was washed with DMF, followed by addition of a mixture of sodium borohydride (151 mg. 4 mmol) in 3 mL of methanol and 7 mL of DMF, and treated at room temperature for 30 minutes to obtain (3-phenyl propyl)-[D-Tyr(tBu)]-Phe-(NMe-Leu)-Pro-[D-Ser(tBu)]-Gln(Trt)-Phe-(D-Ala)-Tic-Ser(tBu)-CTC resin (SEQ ID NO: 130-CTC resin). The resin was washed with DMF, methanol, methyl tert-butyl ether, and then dried.

The dried resin was added to 15 mL of TFA/TIS/H$_2$O (92/4/4) solution, and stirred for 2 hours, and the resin was isolated by filtration. The resin was washed with 1.5 mL of TFA/TIS/H$_2$O (92/4/4) solution. The filtrate was combined, followed by addition of methyl tert-butyl ether (150 mL). The obtained mixture was centrifuged at 3000 rpm for 1 minute and the solid was washed with cold diethyl ether twice, followed by drying. The obtained precipitate was dissolved in DMF, followed by a linear gradient elution (10 min) at a flow rate of 25 mL/min. The eluent A/B: 71/29-61/39 was: eluent A: 0.05% solution of TFA in water; eluent B: 0.05% solution of TFA in acetonitrile. The preparative HPLC was performed on Sunfire, 10 μm, 110 Å column (19×250 mm). The fractions containing the product were collected and lyophilized to obtain a white solid in 49.7 mg.

Mass spectrometry [M/2+H]$^+$: 676.2

Embodiment 86

Preparation of (D-Tyr)-Phe-(NMe-Leu)-[Pro(tran-4F)]-(D-Ser)-Gln-(Nal-2)-(D-Ala)-Tic-Ser (Compound YW-210) (SEQ ID NO: 55)

1.2 g of commercially available CTC resin was swollen in DMF, followed by addition of solution of Fmoc-Ser(tBu)-OH (153 mg, 0.4 mmol) in 10 mL of DMF and addition of DIPEA (207 mg, 1.6 mmol), and treated at room temperature for 16 hours. The resin was washed with DMF, and blocked with the solution of methanol (384 mg, 12 mmol) and DIPEA (413 mg, 3.2 mmol) in 10 mL of DMF. The resin was washed with DMF to obtain Fmoc-Ser(tBu)-CTC resin. The resin was treated with 10 mL of 20% piperidine/DMF solution for 20 minutes to remove Fmoc, and such procedure was repeated twice. The resin was washed with DMF, followed by addition of solution of Fmoc-Tic-OH (479 mg, 1.2 mmol), HATU (456 mg, 1.2 mmol) and HOAt (163 mg, 1.2 mmol) in 10 mL of DMF and addition of DIPEA (310 mg, 2.4 mmol), and treated at room temperature for 40 minutes. The resin was washed with DMF to obtain Fmoc-Tic-Ser(tBu)-CTC resin. Other amino acids, such as D-Ala, Nal-2, Gln(Trt), D-Ser(tBu), Pro(tran-4F), NMe-Leu, Phe and D-Tyr(tBu), were successively introduced in a similar manner to obtain D-Tyr(tBu)-Phe-(NMe-Leu)-Pro-[D-Ser(tBu)]-Gln(Trt)-(Nal-2)-(D-Ala)-Tic-Ser(tBu)-CTC resin (SEQ ID NO: 131-CTC resin). The resin was washed with DMF, methanol, methyl tert-butyl ether, and then dried.

The dried resin was added to 15 mL of TFA/TIS/H$_2$O (92/4/4) solution, and stirred for 2 hours, and the resin was isolated by filtration. The resin was washed with 1.5 mL of TFA/TIS/H$_2$O (92/4/4) solution. The filtrate was combined, followed by addition of methyl tert-butyl ether (150 mL). The obtained mixture was centrifuged at 3000 rpm for 1 minute and the solid was washed with cold diethyl ether twice, followed by drying. The obtained precipitate was dissolved in DMF, followed by a linear gradient elution (10 min) at a flow rate of 25 mL/min. The eluent A/B: 69/31-59/41 was: eluent A: 0.05% solution of TFA in water; eluent B: 0.05% solution of TFA in acetonitrile. The preparative HPLC was performed on Sunfire, 10 μm, 110 Å column (19×250 mm). The fractions containing the product were collected and lyophilized to obtain a white solid in 80.0 mg.

Mass spectrometry [M+H]$^+$: 1301.7

Embodiment 87

Preparation of (NMe-D-Tyr)-Phe-(NMe-Leu)-Pro (tran-4F)-(D-Ser)-Gln-(Nal-2)-(D-Ala)-Tic-(NMe-Ser) (Compound YW-220) (SEQ ID NO: 60)

1.0 g of commercially available CTC resin was swollen in DMF, followed by addition of solution of Fmoc-[NMe-Ser(tBu)]—OH (119 mg, 0.3 mmol) in 10 mL of DMF and addition of DIPEA (155 mg, 1.2 mmol), and treated at room temperature for 16 hours. The resin was washed with DMF, and blocked with the solution of methanol (320 mg, 10 mmol) and DIPEA (310 mg, 2.4 mmol) in 10 mL of DMF. The resin was washed with DMF to obtain Fmoc-[NMe-Ser(tBu)]-CTC resin. The resin was treated with 10 mL of 20% piperidine/DMF solution for 20 minutes to remove Fmoc, and such procedure was repeated twice. The resin was washed with DMF, followed by addition of solution of Fmoc-Tic-OH (359 mg, 0.9 mmol), HATU (342 mg, 0.9 mmol) and HOAt (122 mg, 0.9 mmol) in 10 mL of DMF and addition of DIPEA (232 mg, 1.8 mmol), and treated at room temperature for 40 minutes. The resin was washed with DMF to obtain Fmoc-Tic-[NMe-Ser(tBu)]-CTC resin. Other amino acids, such as D-Ala, (Nal-2), Gln(Trt), D-Ser(tBu), Pro(tran-4F), NMe-Leu, Phe and NMe-D-Tyr(tBu), were successively introduced in a similar manner to obtain 1.5 g CTC resin of the desired polypeptide. The resin was washed with DMF, methanol, methyl tert-butyl ether, and then dried.

The dried resin was added to 10 mL of TFA/TIS/H$_2$O (92/4/4) solution, and stirred for 2 hours, and the resin was isolated by filtration. The resin was washed with 1 mL of TFA/TIS/H$_2$O (92/4/4) solution. The filtrate was combined, followed by addition of methyl tert-butyl ether (110 mL). The obtained mixture was centrifuged at 3000 rpm for 1 minute and the solid was washed with cold diethyl ether twice, followed by drying. The obtained precipitate was dissolved in DMF, followed by a linear gradient elution (10 min) at a flow rate of 25 mL/min. The eluent A/B: 95/5-35/65 was: eluent A: 0.05% solution of TFA in water; eluent B: 0.05% solution of TFA in acetonitrile. The preparative HPLC was performed on Sunfire, 10 μm, 110 Å column (19×250 mm). The fractions containing the product were collected and lyophilized to obtain a white solid in 24.0 mg.

Mass spectrometry [M+H]$^+$: 1328.6

Embodiment 88

Preparation of (D-Tyr(3F))-Phe-(NMe-Leu)-Pro(tran-4F)-(D-Ser)-Gln-(Nal-2)-(D-Ala)-Tic-(NMe-Ser) (Compound YW-221) (SEQ ID NO: 61)

1.0 g of commercially available CTC resin was swollen in DMF, followed by addition of solution of Fmoc-[NMe-Ser(tBu)]—OH (119 mg, 0.3 mmol) in 10 mL of DMF and addition of DIPEA (155 mg, 1.2 mmol), and treated at room temperature for 16 hours. The resin was washed with DMF, and blocked with the solution of methanol (320 mg, 10 mmol) and DIPEA (310 mg, 2.4 mmol) in 10 mL of DMF. The resin was washed with DMF to obtain Fmoc-[NMe-Ser(tBu)]-CTC resin. The resin was treated with 10 mL of 20% piperidine/DMF solution for 20 minutes to remove Fmoc, and such procedure was repeated twice. The resin was washed with DMF, followed by addition of solution of Fmoc-Tic-OH (359 mg, 0.9 mmol), HATU (342 mg, 0.9 mmol) and HOAt (122 mg, 0.9 mmol) in 10 mL of DMF and addition of DIPEA (232 mg, 1.8 mmol), and treated at room temperature for 40 minutes. The resin was washed with DMF to obtain Fmoc-Tic-[NMe-Ser(tBu)]-CTC resin. Other amino acids, such as D-Ala, (Nal-2), Gln(Trt), D-Ser(tBu), Pro(tran-4F), NMe-Leu, Phe and D-Tyr(3F), were successively introduced in a similar manner to obtain 1.5 g CTC resin of the desired polypeptide. The resin was washed with DMF, methanol, methyl tert-butyl ether, and then dried.

The dried resin was added to 10 mL of TFA/TIS/H$_2$O (92/4/4) solution, and stirred for 2 hours, and the resin was isolated by filtration. The resin was washed with 1 mL of TFA/TIS/H$_2$O (92/4/4) solution. The filtrate was combined, followed by addition of methyl tert-butyl ether (110 mL). The obtained mixture was centrifuged at 3000 rpm for 1 minute and the solid was washed with cold diethyl ether twice, followed by drying. The obtained precipitate was dissolved in DMF, followed by a linear gradient elution (10 min) at a flow rate of 25 mL/min. The eluent A/B: 70/30-60/40 was: eluent A: 0.05% solution of TFA in water; eluent B: 0.05% solution of TFA in acetonitrile. The preparative HPLC was performed on Phenomenex C$_{18}$ column (21.2×250 mm). The fractions containing the product were collected and lyophilized to obtain a white solid in 19.8 mg.

Mass spectrometry [M/2+H]$^+$: 667.0

Embodiment 89

Preparation of [D-Tyr(3F)]-Phe-(NMe-Leu)-Pro(tran-4F)-(D-Ser)-Gln-(Nal-2)-(D-Ala)-Tic-Ser (Compound YW-222) (SEQ ID NO: 22)

1.0 g of commercially available CTC resin was swollen in DMF, followed by addition of solution of Fmoc-Ser(tBu)-OH (115 mg, 0.3 mmol) in 10 mL of DMF and addition of DIPEA (155 mg, 1.2 mmol), and treated at room temperature for 16 hours. The resin was washed with DMF, and blocked with the solution of methanol (320 mg, 10 mmol) and DIPEA (310 mg, 2.4 mmol) in 10 mL of DMF. The resin was washed with DMF to obtain Fmoc-Ser(tBu)-CTC resin. The resin was treated with 10 mL of 20% piperidine/DMF solution for 20 minutes to remove Fmoc, and such procedure was repeated twice. The resin was washed with DMF, followed by addition of solution of Fmoc-Tic-OH (359 mg, 0.9 mmol), HATU (342 mg, 0.9 mmol) and HOAt (122 mg, 0.9 mmol) in 10 mL of DMF and addition of DIPEA (232 mg, 1.8 mmol), and treated at room temperature for 40 minutes. The resin was washed with DMF to obtain Fmoc-Tic-Ser(tBu)-CTC resin. Other amino acids, such as D-Ala, Nal-2, Gln(Trt), D-Ser(tBu), Pro(tran-4F), NMe-Leu, Phe and D-Tyr(3F), were successively introduced in a similar manner to obtain 1.5 g of D-Tyr(3F)-Phe-(NMe-Leu)-Pro(tran-4F)-[D-Ser(tBu)]-Gln(Trt)-(Nal-2)-(D-Ala)-Tic-Ser(tBu)-CTC resin (SEQ ID NO: 132-CTC resin). The resin was washed with DMF, methanol, methyl tert-butyl ether, and then dried.

The dried resin was added to 10 mL of TFA/TIS/H$_2$O (92/4/4) solution, and stirred for 2 hours, and the resin was isolated by filtration. The resin was washed with 1 mL of TFA/TIS/H$_2$O (92/4/4) solution. The filtrate was combined, followed by addition of methyl tert-butyl ether (110 mL). The obtained mixture was centrifuged at 3000 rpm for 1 minute and the solid was washed with cold diethyl ether twice, followed by drying. The obtained precipitate was dissolved in DMF, followed by a linear gradient elution (10 min) at a flow rate of 25 mL/min. The eluent A/B: 72/28-66/34 was: eluent A: 0.05% solution of TFA in water; eluent B: 0.05% solution of TFA in acetonitrile. The preparative HPLC was performed on Sunfire, 10 μm, 110 Å column (19×250 mm). The fractions containing the product were collected and lyophilized to obtain a white solid in 44.2 mg.

Mass spectrometry [M/2+H]$^+$: 660.3

Embodiment 90

Preparation of Palm-PEG8-Gly-Gly-(D-Tyr)-Phe-(NMe-Leu)-Pro(tran-4F)-(D-Ser)-Gln-(Nal-2)-(D-Ala)-Tic-Ser (Compound YW-223) (SEQ ID NO: 63)

1.0 g of commercially available CTC resin was swollen in DMF, followed by addition of solution of Fmoc-Ser(tBu)-OH (115 mg, 0.3 mmol) in 10 mL of DMF and addition of DIPEA (155 mg, 1.2 mmol), and treated at room temperature for 16 hours. The resin was washed with DMF, and blocked with the solution of methanol (320 mg, 10 mmol) and DIPEA (310 mg, 2.4 mmol) in 10 mL of DMF. The resin was washed with DMF to obtain Fmoc-Ser(tBu)-CTC resin. The resin was treated with 10 mL of 20% piperidine/DMF solution for 20 minutes to remove Fmoc, and such procedure was repeated twice. The resin was washed with DMF, followed by addition of 10 mL of solution of Fmoc-Tic-OH (359 mg, 0.9 mmol), HATU (342 mg, 0.9 mmol) and HOAt (122 mg, 0.9 mmol) in 10 mL of DMF and addition of DIPEA (232 mg, 1.8 mmol), and treated at room temperature for 40 minutes. The resin was washed with DMF to obtain Fmoc-Tic-Ser(tBu)-CTC resin. Other amino acids, such as D-Ala, Nal-2, Gln(Trt), D-Ser(tBu), Pro(tran-4F), NMe-Leu, Phe, D-Tyr, Gly, Gly, PEG8 and Palm, were successively introduced in a similar manner to obtain 1.6 g of desired polypeptide CTC resin. The resin was washed with DMF, methanol, methyl tert-butyl ether, and then dried.

The dried resin was added to 10 mL of TFA/TIS/$H_2O$ (92/4/4) solution, and stirred for 2 hours, and the resin was isolated by filtration. The resin was washed with 1 mL of TFA/TIS/$H_2O$ (92/4/4) solution. The filtrate was combined, followed by addition of methyl tert-butyl ether (110 mL). The obtained mixture was centrifuged at 3000 rpm for 1 minute and the solid was washed with cold diethyl ether twice, followed by drying. The obtained precipitate was dissolved in DMF, followed by a linear gradient elution (10 min) at a flow rate of 25 mL/min. The eluent A/B: 33/67-23/77 was: eluent A: 0.05% solution of TFA in water; eluent B: 0.05% solution of TFA in acetonitrile. The preparative HPLC was performed on Phenomenex $C_{18}$ column (21.2× 250 mm). The fractions containing the product were collected and lyophilized to obtain a white solid in 63.4 mg.

Mass spectrometry $[M/3+H]^+$: 693.0

Embodiment 91

Preparation of (NMe-D-Tyr)-Phe-(NMe-Leu)-DiFluorPro-(D-Ser)-Gln-(Nal-2)-(D-Ala)-Tic-(NMe-Ser) (Compound YW-225) (SEQ ID NO: 65)

1.0 g of commercially available CTC resin was swollen in DMF, followed by addition of solution of Fmoc-[NMe-Ser (tBu)]—OH (119 mg, 0.3 mmol) in 10 mL of DMF and addition of DIPEA (155 mg, 1.2 mmol), and treated at room temperature for 16 hours. The resin was washed with DMF, and blocked with the solution of methanol (320 mg, 10 mmol) and DIPEA (310 mg, 2.4 mmol) in 10 mL of DMF. The resin was washed with DMF to obtain Fmoc-[NMe-Ser (tBu)]-CTC resin. The resin was treated with 10 mL of 20% piperidine/DMF solution for 20 minutes to remove Fmoc, and such procedure was repeated twice. The resin was washed with DMF, followed by addition of solution of Fmoc-Tic-OH (359 mg, 0.9 mmol), HATU (342 mg, 0.9 mmol) and HOAt (122 mg, 0.9 mmol) in 10 mL of DMF and addition of DIPEA (232 mg, 1.8 mmol), and treated at room temperature for 40 minutes. The resin was washed with DMF to obtain Fmoc-Tic-[NMe-Ser(tBu)]-CTC resin. Other amino acids, such as D-Ala, (Nal-2), Gln(Trt), D-Ser(tBu), DiFluorPro, NMe-Leu, Phe and NMe-D-Tyr(tBu), were successively introduced in a similar manner to obtain 1.5 g of desired polypeptide CTC resin. The resin was washed with DMF, methanol, methyl tert-butyl ether, and then dried.

The dried resin was added to 10 mL of TFA/TIS/$H_2O$ (92/4/4) solution, and stirred for 2 hours, and the resin was isolated by filtration. The resin was washed with 1 mL of TFA/TIS/$H_2O$ (92/4/4) solution. The filtrate was combined, followed by addition of methyl tert-butyl ether (110 mL). The obtained mixture was centrifuged at 3000 rpm for 1 minute and the solid was washed with cold diethyl ether twice, followed by drying. The obtained precipitate was dissolved in DMF, followed by a linear gradient elution (10 min) at a flow rate of 25 mL/min. The eluent A/B: 68/32-60/40 was: eluent A: 0.05% solution of TFA in water; eluent B: 0.05% solution of TFA in acetonitrile. The preparative HPLC was performed on XBridge Peptide BEH C18, 10 μm, 120 Å column (19×250 mm). The fractions containing the product were collected and lyophilized to obtain a white solid in 43.6 mg.

Mass spectrometry $[M/2+H]^+$: 674.0

Embodiment 91

Preparation of (D-Tyr(3F))-Phe-(NMe-Leu)-(DiFluorPro)-(D-Ser)-Gln-(Nal-2)-(D-Ala)-Tic-(NMe-Ser) (Compound YW-226) (SEQ ID NO: 66)

1.0 g of commercially available CTC resin was swollen in DMF, followed by addition of solution of Fmoc-[NMe-Ser (tBu)]—OH (119 mg, 0.3 mmol) in 10 mL of DMF and addition of DIPEA (155 mg, 1.2 mmol), and treated at room temperature for 16 hours. The resin was washed with DMF, and blocked with the solution of methanol (320 mg, 10 mmol) and DIPEA (310 mg, 2.4 mmol) in 10 mL of DMF. The resin was washed with DMF to obtain Fmoc-[NMe-Ser (tBu)]-CTC resin. The resin was treated with 10 mL of 20% piperidine/DMF solution for 20 minutes to remove Fmoc, and such procedure was repeated twice. The resin was washed with DMF, followed by addition of solution of Fmoc-Tic-OH (359 mg, 0.9 mmol), HATU (342 mg, 0.9 mmol) and HOAt (122 mg, 0.9 mmol) in 10 mL of DMF and addition of DIPEA (232 mg, 1.8 mmol), and treated at room temperature for 40 minutes. The resin was washed with DMF to obtain Fmoc-Tic-[NMe-Ser(tBu)]-CTC resin. Other amino acids, such as D-Ala, (Nal-2), Gln(Trt), D-Ser(tBu), DiFluorPro, NMe-Leu, Phe and D-Tyr(3F), were successively introduced in a similar manner to obtain 1.5 g of desired polypeptide CTC resin. The resin was washed with DMF, methanol, methyl tert-butyl ether, and then dried.

The dried resin was added to 10 mL of TFA/TIS/$H_2O$ (92/4/4) solution, and stirred for 2 hours, and the resin was isolated by filtration. The resin was washed with 1 mL of TFA/TIS/$H_2O$ (92/4/4) solution. The filtrate was combined, followed by addition of methyl tert-butyl ether (110 mL). The obtained mixture was centrifuged at 3000 rpm for 1 minute and the solid was washed with cold diethyl ether twice, followed by drying. The obtained precipitate was dissolved in DMF, followed by a linear gradient elution (10 min) at a flow rate of 25 mL/min. The eluent A/B: 68/32-60/40 was: eluent A: 0.05% solution of TFA in water; eluent B: 0.05% solution of TFA in acetonitrile. The preparative HPLC was performed on XBridge Peptide BEH C18, 10 μm, 120 Å column (19×250 mm). The fractions containing the product were collected and lyophilized to obtain a white solid in 34.1 mg.

Mass spectrometry $[M/2+H]^+$: 676.0

The polypeptide prepared in the above embodiments and the polypeptide prepared by referring to the above embodiments were shown in Table 2 below. The purity analysis conditions, retention time, characterization data and effect data of each polypeptide (determination by the method of Effect Embodiment 1) were also described in Table 2.

TABLE 2

List of embodiments

| Polypeptide No. | | Sequence | Mw (obs.) [M + 2H]⁺/2 | Mw (cal.) | Rt (min.) HPLC | HPLC purity analysis conditions | EC$_{50}$ (µM) | SEQ ID NO: |
|---|---|---|---|---|---|---|---|---|
| YW-98 | MC9(D-Y147, NMeL149, D-S151, D-A154, Tic155) | (D-Tyr)-Phe-(NMe-Leu)-Pro-(D-Ser)-Gln-Phe-(D-Ala)-Tic-Ser | 1255.4 [M + Na]⁺ | 1232.38 | 14.61 | C | 0.0030 | 1 |
| YW-100 | MC9(D-Y147, NMeF149, D-S151, D-A154, Tic155) | (D-Tyr)-Phe-(NMe-Phe)-Pro-(D-Ser)-Gln-Phe-(D-Ala)-Tic-Ser | 634.0 | 1266.40 | 15.24 | C | 0.0420 | 2 |
| YW-101 | MC9(D-Y147, NMeHL149, D-S151, D-A154, Tic155) | (D-Tyr)-Phe-(NMe-HoLeu)-Pro-(D-Ser)-Gln-Phe-(D-Ala)-Tic-Ser | 1247.7 [M + H]⁺ | 1246.41 | 15.30 | C | 0.0029 | 3 |
| YW-105 | MC9(D-Y147, NMeF148, NMeL149, D-S151, D-A154, Tic155) | (D-Tyr)-(NMe-Phe)-(NMe-Leu)-Pro-(D-Ser)-Gln-Phe-(D-Ala)-Tic-Ser | 624.0 | 1246.41 | 14.40 | C | 0.0106 | 4 |
| YW-111 | MC9(3PPA, D-Y147, NMeL149, D-S151, D-A154 Tic155) | 3-Phenylpropanoyl-(D-Tyr)-Phe-(NMe-Leu)-Pro-(D-Ser)-Gln-Phe-(D-Ala)-Tic-Ser | 683.4 | 1364.54 | 15.20 | I | 0.0020 | 5 |
| YW-121 | MC9(D-Y147, NMeL149, Thz150, D-S151, D-A154, Tic155) | (D-Tyr)-Phe-(NMe-Leu)-Thz-(D-Ser)-Gln-Phe-(D-Ala)-Tic-Ser | 813.3 [Thz-(D-ser)-Gln-Phe-(D-Ala)-Tic-Ser]+ 438.3 [(D-Tyr)-Phe-(NMe-Leu)]+ | 1250.42 | 16.72 | J | 0.0007 | 6 |
| YW-122 | MC9(D-Y147, NMeL149, Thz150, D-S151, 2Nal153, D-A154, Tic155) | (D-Tyr)-Phe-(NMe-Leu)-Thz-(D-Ser)-Gln-2Nal-(D-Ala)-Tic-Ser | 863.4 [Thz-(D-ser)-Gln-(Nal-2)-(D-Ala)-Tic-Ser]+ 438.3 [(D-Tyr)-Phe-(NMe-Leu)]+ | 1300.48 | 17.97 | J | 0.0006 | 7 |
| YW-123 | MC9(D-NMeY147, NMeL149, Thz150, D-S151, D-A154, Tic155) | (NMe-D-Tyr)-Phe-(NMe-Leu)-Thz-(D-Ser)-Gln-Phe-(D-Ala)-Tic-Ser | 633.0 | 1264.46 | 14.53 | A | 0.001 | 8 |

TABLE 2-continued

List of embodiments

| Poly-peptide No. | | Sequence | Mw (obs.) [M + 2H]⁺/2 | Mw (cal.) | Rt (min.) HPLC | HPLC purity analysis conditions | EC₅₀ (μM) | SEQ ID NO: |
|---|---|---|---|---|---|---|---|---|
| YW-124 | MC9(D-NMeY147, NMeL149, Thz150, D-S151, D-A154, Tic155, NMeS156) | (NMe-D-Tyr)-Phe-(NMe-Leu)-Thz-(D-Ser)-Gln-Phe-(D-Ala)-Tic-(NMe-Ser) | 639.9 | 1277.58 | 14.64 | C | 0.0013 | 9 |
| YW-125 | MC9(D-NMeY147, NMeL149, Thz150, D-S151, 2Nal153 D-A154, Tic155, NMeS156) | (NMe-D-Tyr)-Phe-(NMe-Leu)-Thz-(D-Ser)-Gln-2Nal-(D-Ala)-Tic-(NMe-Ser) | 665.0 | 1327.59 | 15.80 | C | 0.0006 | 10 |
| YW-133 | MC9(Palm-PEG8, G145, G146, D-Y147 NMeL149, D-S151, D-A154 Tic155) | Palm-PEG8-Gly-Gly-(D-Tyr)-Phe-(NMe-Leu)-Pro-(D-Ser)-Gln-Phe-(D-Ala)-Tic-Ser | 1004.5 | 2008.39 | 12.29 | K | 0.0007 | 11 |
| YW-134 | MC9(Palm-PEG8, βA145, βA146, D-Y147, NMeL149, D-S151, D-A154, Tic155) | Palm-PEG8-βAla-βAla-(D-Tyr)-Phe-(NMe-Leu)-Pro-(D-Ser)-Gln-Phe-(D-Ala)-Tic-Ser | 1019.2 | 2036.44 | 11.97 | K | 0.0007 | 12 |
| YW-142 | MC9(D-NMeY147, NMeL149, Thz150, D-S151, 1Nal153 D-A154, Tic155, NMeS156) | (NMe-D-Tyr)-Phe-(NMe-Leu)-Thz-(D-Ser)-Gln-1Nal-(D-Ala)-Tic-(NMe-Ser) | 665.3 | 1328.53 | 11.81 | L | 0.0009 | 13 |
| YW-146 | MC9(D-NMeY147, NMeL149, D-S151, 2Nal153, D-A154, Tic155, NMeS156) | (NMe-D-Tyr)-Phe-(NMe-Leu)-Pro-(D-Ser)-Gln-2Nal-(D-Ala)-Tic-(NMe-Ser) | 656.5 | 1310.49 | 11.59 | L | 0.0014 | 14 |
| YW-148 | MC9(D-NMeY147, NMeL149, Thz150, D-S151, 2Nal153, D-A154, Tic155) | (D-NMe-Tyr)-Phe-(NMe-Leu)-Thz-(D-Ser)-Gln-2Nal-(D-Ala)-Tic-Ser | 658.0 | 1314.51 | 17.56 | J | 0.0005 | 15 |
| YW-153 | MC9(D-Y147, NMeL149, D-S151, D-A154 D-Ti1c155) | (D-Tyr)-Phe-(NMe-Leu)-Pro-(D-Ser)-Gln-Phe-(D-Ala)-(D-Ti1c)-Ser | 617.0 | 1232.38 | 9.99 | L | 0.0085 | 16 |
| YW-161 | MC9(3-phenylpropanoyl, D-Y147, NMeL149, D-S151, D-A154, Tic155, NH2) | 3-Phenylpropanoyl-(D-Tyr)-Phe-(NMe-Leu)-Pro-(D-Ser)-Gln-Phe-(D-Ala)-Tic-Ser-NH2 | 682.8 | 1363.58 | 13.90 | L | 0.0030 | 17 |

TABLE 2-continued

List of embodiments

| Poly-peptide No. | | Sequence | Mw (obs.) [M + 2H]+/2 | Mw (cal.) | Rt (min.) HPLC | HPLC purity analysis conditions | EC50 (μM) | SEQ ID NO: |
|---|---|---|---|---|---|---|---|---|
| YW-162 | MC9(D-NMeY147, NMeL149, D-S151, 1Nal153, D-A154, Tic155, NMeS156) | (D-NMe-Tyr)-Phe-(NMe-Leu)-Pro-(D-Ser)-Gln-1Nal-(D-Ala)-Tic-(NMe-Ser) | 656.5 | 1310.49 | 19.21 | J | 0.0026 | 18 |
| YW-163 | MC9(D-NMeY147, NMeL149, D-S151, D-A154, Tic155) | (D-NMe-Tyr)-Phe-(NMe-Leu)-Pro-(D-Ser)-Gln-Phe-(D-Ala)-Tic-Ser | 623.9 | 1246.41 | 16.24 | J | 0.0022 | 19 |
| YW-164 | MC9(D-Y147, NMeL149, D-S151, 2Nal153, D-A154, Tic155) | (D-Tyr)-Phe-(NMe-Leu)-Pro-(D-Ser)-Gln-2Nal-(D-Ala)-Tic-Ser | 641.8 | 1282.44 | 15.72 | C | 0.0011 | 20 |
| YW-165 | MC9(D-Y147, NMeL149, D-S151, 1Nal153, D-A154, Tic155) | (D-Tyr)-Phe-(NMe-Leu)-Pro-(D-Ser)-Gln-1Nal-(D-Ala)-Tic-Ser | 642.2 | 1282.44 | 17.60 | N | 0.0015 | 21 |
| YW-166 | MC9(D-Y147, NMeL149, D-S151, D-A154, Tic155, NMeS156) | (D-Tyr)-Phe-(NMe-Leu)-Pro-(D-Ser)-Gln-Phe-(D-Ala)-Tic-(NMe-Ser) | 1246.7 [M + H]+ | 1246.41 | 16.56 | J | 0.0050 | 22 |
| YW-167 | MC9(D-NMeY147, NMeL149, D-S151, 2Nal153, D-A154, Tic155) | (D-NMe-Tyr)-Phe-(NMe-Leu)-Pro-(D-Ser)-Gln-2Nal-(D-Ala)-Tic-Ser | 648.8 | 1296.47 | 17.55 | J | 0.0008 | 23 |
| YW-168 | MC9(D-NMeY147, NMeL149, D-S151, 1Nal153, D-A154, Tic155) | (D-NMe-Tyr)-Phe-(NMe-Leu)-Pro-(D-Ser)-Gln-1Nal-(D-Ala)-Tic-Ser | 649.0 | 1296.47 | 17.53 | J | 0.0012 | 24 |
| YW-171 | MC9(D-Y147, NMeL149, D-S151, D-A154, Tic155, HoSer156) | (D-Tyr)-Phe-(NMe-Leu)-Pro-(D-Ser)-Gln-Phe-(D-Ala)-Tic-(HoSer) | 1246.6 [M + H]+ | 1246.41 | 14.41 | C | 0.029 | 25 |
| YW-172 | MC9(D-Y147, NMeL149, D-S151, D-A154, Tic155, NHoSer156) | (D-Tyr)-Phe-(NMe-Leu)-Pro-(D-Ser)-Gln-Phe-(D-Ala)-Tic-(NHoSer) | 624.0 | 1246.43 | 13.54 | J | 0.0058 | 26 |
| YW-174 | MC9(D-Y147, NMeL149, Pro(diF)150, D-S151, D-A154, Tic155) | (D-Tyr)-Phe-(NMe-Leu)-Pro(diF)-(D-Ser)-Gln-Phe-(D-Ala)-Tic-Ser | 634.9 | 1268.36 | 16.97 | J | 0.0012 | 27 |
| YW-175 | MC9(D-Y147, (NMe-Leu)-Pro-NMeL149, D-HoSer151, D-A154, Tic155) | (D-Tyr)-Phe-(D-HoSer)-Gln-Phe-(D-Ala)-Tic-Ser | 1247.7 [M + H]+ | 1246.41 | 13.50 | J | 0.091 | 28 |

TABLE 2-continued

List of embodiments

| Poly-peptide No. | | Sequence | Mw (obs.) [M + 2H]⁺/2 | Mw (cal.) | Rt (min.) HPLC | HPLC purity analysis conditions | EC₅₀ (µM) | SEQ ID NO: |
|---|---|---|---|---|---|---|---|---|
| YW-176 | MC9(D-Y147, NMeL149, D-S151, D-A154 D-Oic155) | (D-Tyr)-Phe-(NMe-Leu)-Pro-(D-Ser)-Gln-Phe-(D-Ala)-(D-Oic)-Ser | 612.7 | 1224.40 | 16.20 | J | 0.0038 | 29 |
| YW-177 | MC9(D-Y147, NMeL149, D-S151, D-A154, Tic155, NMeHoS156) | (D-Tyr)-Phe-(NMe-Leu)-Pro-(D-Ser)-Gln-Phe-(D-Ala)-Tic-(NMe-HoSer) | 631.0 | 1260.46 | 13.66 | J | 0.0250 | 30 |
| YW-178 | MC9(Palm-PEG8, G145, G146, D-NMeY147, NMeL149, D-S151, 2Nal153, D-A154, Tic155, NMeS156) | Palm-PEG8-Gly-Gly-(D-NMe-Tyr)-Phe-(NMe-Leu)-Pro-(D-Ser)-Gln-2Nal-(D-Ala)-Tic-(NMe-Ser) | 1043.9 | 2086.5 | 12.59 | H | 0.0021 | 31 |
| YW-179 | MC9(Palm-PEG8, betaA145, betaA146, D-NMeY147, NMeL149, D-S151, 2Nal153 D-A154, Tic155, NMeS156) | Palm-PEG8-βAla-βAla4 D-NMe-Tyr)-Phe-(NMe-Leu)-Pro-(D-Ser)-Gln-2Nal-(D-Ala)-Tic-(NMe-Ser) | 1058.1 | 2114.56 | 12.35 | H | 0.0021 | 32 |
| YW-180 | MC9(tetradecanoyl-PEG8, βA145, βA146, D-NMeY147, NMeL149, D-S151, 2Nal153, D-A154, Tic155, NMeS156) | Tetradecanoyl-PEG8-βAla-βAla-(D-NMe-Tyr)-Phe-(NMe-Leu)-Pro-(D-Ser)-Gln-2Nal-(D-Ala)-Tic-(NMe-Ser) | 1043.8 | 2085.5 | 14.38 | N | 0.0014 | 33 |
| YW-181 | MC9(dodecanoyl-PEG8, βA145, βA146, D-NMeY147, NMeL149, D-S151, 2Nal153, D-A154, Tic155, NMeS156) | Dodecanoyl-PEG8-βAla-βAla-(NMe-D-Tyr)-Phe-(NMe-Leu)-Pro-(D-Ser)-Gln-2Nal-(D-Ala)-Tic-(NMe-Ser) | 1029.8 | 2058.45 | 18.04 | G | 0.0022 | 34 |
| YW-182 | MC9(D-Y147, NMeL149, D-S151, D-A154 D-Tic155, NMeS156) | (D-Tyr)-Phe-(NMe-Leu)-Pro-(D-Ser)-Gln-Phe-(D-Ala)-(D-Tic)-(NMe-Ser) | 624.0 | 1246.41 | 16.02 | J | 0.041 | 35 |
| YW-183 | MC9(D-Y147, NEtL149, D-S151, D-A154, Tic155) | (D-Tyr)-Phe-(NEt-Leu)-Pro-(D-Ser)-Gln-Phe-(D-Ala)-Tic-Ser | 1246.6 [M + H]⁺ | 1246.41 | 13.96 | J | 0.0092 | 36 |
| YW-184 | MC9(D-Y147, NprL149, D-S151, D-A154, Tic155) | (D-Tyr)-Phe-(NPr-Leu)-Pro-(D-Ser)-Gln-Phe-(D-Ala)-Tic-Ser | 1261.7 [M + H]⁺ | 1260.44 | 14.56 | J | 0.016 | 37 |

TABLE 2-continued

List of embodiments

| Poly-peptide No. | | Sequence | Mw (obs.) [M + 2H]⁺/2 | Mw (cal.) | Rt (min.) HPLC | HPLC purity analysis conditions | EC$_{50}$ (µM) | SEQ ID NO: |
|---|---|---|---|---|---|---|---|---|
| YW-185 | MC9(3-phenylpropanoyl, D-Y147, NEtL149, D-S151, D-A154, Tic155) | 3-Phenylpropanoyl-(D-Tyr)-Phe-(NEt-Leu)-Pro-(D-Ser)-Gln-Phe-(D-Ala)-Tic-Ser | 1379.2 [M + H]⁺ | 1378.57 | 13.70 | J | 0.0059 | 38 |
| YW-186 | MC9(3-phenylpropanoyl, D-Y147, NprL149, D-S151, D-A154, Tic155) | 3-Phenylpropanoyl-(D-Tyr)-Phe-(NPr-Leu)-Pro-(D-Ser)-Gln-Phe-(D-Ala)-Tic-Ser | 1393.7 [M + H]⁺ | 1392.59 | 14.14 | J | 0.011 | 39 |
| YW-190 | MC9(D-Y147, NMeL149, D-S151, D-A154 Tic155, NH2) | (D-Tyr)-Phe-(NMe-Leu)-Pro-(D-Ser)-Gln-Phe-(D-Ala)-(D-Tic)-Ser-NH2 | 1232.6 [M + H]⁺ | 1231.40 | 13.26 | J | 0.0027 | 40 |
| YW-192 | MC9(DiMe-D-Y147, NMeL149, D-S151, D-A154, Tic155) | DiMe-(D-Tyr)-Phe-(NMe-Leu)-Pro-(D-Ser)-Gln-Phe-(D-Ala)-Tic-Ser | 631.2 | 1260.46 | 16.41 | J | 0.0026 | 41 |
| YW-193 | MC9(hexanoyl, D-Y147, NMeL149, D-S151, D-A154, Tic155) | Hexanoyl-(D-Tyr)-Phe-(NMe-Leu)-Pro-(D-Ser)-Gln-Phe-(D-Ala)-Tic-Ser | 1331.7 [M + H]⁺ | 1330.52 | 17.40 | J | 0.0014 | 42 |
| YW-194 | MC9(2-cyclohexyl acetyl, D-Y147, NMeL149, D-S151, D-A154, Tic155) | (2-Cyclohexylacetyl)-(D-Tyr)-Phe-(NMe-Leu)-Pro-(D-Ser)-Gln-Phe-(D-Ala)-Tic-Ser | 1357.6 [M + H]⁺ | 1356.56 | 17.93 | J | 0.0012 | 43 |
| YW-195 | MC9(4-(trifluoromethyl) benzoyl, D-Y147, NMeL149, D-S151, D-A154, Tic155) | 4-(Trifluoromethyl) benzoyl-(D-Tyr)-Phe-(NMe-Leu)-Pro-(D-Ser)-Gln-Phe-(D-Ala)-Tic-Ser | 1426.6 [M + Na]⁺ | 1404.49 | 18.40 | J | 0.0008 | 44 |
| YW-198 | MC9(D-Y147, NMeL149, Hyp150, D-S151, D-A154 Tic155) | (D-Tyr)-Phe-(NMe-Leu)-Hyp-(D-Ser)-Gln-Phe-(D-Ala)-Tic-Ser | 1248.6 [M + H]⁺ | 1248.38 | 13.23 | J | 0.0053 | 45 |
| YW-199 | MC9(D-Y147, 1Nal148, NMeL149, D-S151, D-A154, Tic155) | (D-Tyr)-1Nal-(NMe-Leu)-Pro-(D-Ser)-Gln-Phe-(D-Ala)-Tic-Ser | 1282.5 [M + H]⁺ | 1282.44 | 14.66 | J | 0.0029 | 46 |
| YW-200 | MC9(D-Y147, 2Nal148, NMeL149, D-S151, D-A154, Tic155) | (D-Tyr)-2Nal-(NMe-Leu)-Pro-(D-Ser)-Gln-Phe-(D-Ala)-Tic-Ser | 1282.5 [M + H]⁺ | 1282.44 | 14.76 | J | 0.019 | 47 |
| YW-201 | MC9(D-Y147, Bpa148, NMeL149, D-S151, D-A154, Tic155) | (D-Tyr)-Bpa-(NMe-Leu)-Pro-(D-Ser)-Gln-Phe-(D-Ala)-Tic-Ser | 1337.6 [M + H]⁺ | 1336.49 | 14.91 | J | 0.076 | 48 |

TABLE 2-continued

List of embodiments

| Poly-peptide No. | | Sequence | Mw (obs.) [M + 2H]⁺/2 | Mw (cal.) | Rt (min.) HPLC | HPLC purity analysis conditions | EC₅₀ (μM) | SEQ ID NO: |
|---|---|---|---|---|---|---|---|---|
| YW-202 | MC9(D-Y147, F(4-Me)148, NMeL149, D-S151, D-A154, Tic155) | (D-Tyr)-Phe(4-Me)-(NMe-Leu)-Pro-(D-Ser)-Gln-Phe-(D-Ala)-Tic-Ser | 1246.7 [M + H]⁺ | 1246.41 | 14.22 | J | 0.0064 | 49 |
| YW-203 | MC9(D-Y147, F(4-Cl)148, NMeL149, D-S151, D-A154, Tic155) | (D-Tyr)-Phe(4-Cl)-(NMe-Leu)-Pro-(D-Ser)-Gln-Phe-(D-Ala)-Tic-Ser | 1267.4 [M + H]⁺ | 1266.83 | 14.40 | J | 0.0082 | 50 |
| YW-204 | MC9(D-Y147, NMeL149, D-T151, D-A154, Tic155) | (D-Tyr)-Phe-(NMe-Leu)-Pro-(D-Thr)-Gln-Phe-(D-Ala)-Tic-Ser | 1246.5 [M + H]⁺ | 1246.43 | 17.15 | J | 0.062 | 51 |
| YW-205 | MC9(D-Y147, NMeL149, D-S151, D-A154, F(4-Me)155) | (D-Tyr)-Phe-(NMe-Leu)-Pro-(D-Ser)-Gln-Phe-(D-Ala)-Phe(4-Me)-Ser | 1234.6 [M + H]⁺ | 1234.42 | 14.02 | J | 0.0062 | 52 |
| YW-206 | MC9(D-Y147, NMeL149, D-S151, D-A154, F(4-Cl)155) | (D-Tyr)-Phe-(NMe-Leu)-Pro-(D-Ser)-Gln-Phe-(D-Ala)-Phe(4-Cl)-Ser | 1254.7 [M + H]⁺ | 1254.83 | 14.25 | J | 0.009 | 53 |
| YW-207 | MC9(D-Y147, NMeL149, D-S151, D-A154, Tic155) | 3-phenylpropyl-(D-Tyr)-Phe-(NMe-Leu)-Pro-(D-Ser)-Gln-Phe-(D-Ala)-Tic-Ser | 676.2 | 1350.58 | 15.21 | J | 0.00092 | 54 |
| YW-210 | MC9(D-Y147, NMeL149, Pro(4Ph)150, D-S151, 2Nal153, D-A154, Tic155) | (D-Tyr)-Phe-(NMe-Leu)-Pro(4Ph)-(D-Ser)-Gln-2Nal-(D-Ala)-Tic-Ser | 1301.7 [M + H]⁺ | 1300.45 | 17.73 | J | 0.00031 | 55 |
| YW-215 | MC9(D-Y147, NMeL149, Pro(4Ph)150, D-S151, D-A154, Tic155) | (D-Tyr)-Phe-NMeLeu-Pro(4Ph)-(D-Ser)-Gln-Phe-(D-Ala)-Tic-Ser | 1308.8 [M + H]⁺ | 1308.5 | 15.29 | J | 0.0048 | 56 |
| YW-216 | MC9(D-NMeY147, NMeL149, Pro(4Ph)150, D-S151, D-A154, Tic155) | (D-NMe-Tyr)-Phe-NMeLeu-Pro(4Ph)-(D-Ser)-Gln-2Nal-(D-Ala)-Tic-Ser | 694.0 | 1386.59 | 16.29 | J | 0.0013 | 57 |
| YW-217 | MC9(D-NMeY147, NMeL149, Pro(4Ph)150, D-S151, D-A154, Tic155) | Palm-PEG8-βAla-βAla-(D-NMe-Tyr)-Phe-(NMe-Leu)-Pro(4Ph)-(D-Ser)-Gln-2Nal-(D-Ala)-Tic-Ser | 1096.8 | 2190.69 | 17.06 | N | 0.0033 | 58 |
| YW-219 | MC9(D-Y147, NMeL149, Pro(4Ph)150, D-S151, 2Nal153, D-A154, Tic155) | (D-Tyr)-Phe-(NMe-Leu)-Pro(4Ph)-(D-Ser)-Gln-2Nal-(D-Ala)-Tic-Ser | 1314.6 [M + H]⁺ | 1314.48 | 15.67 | J | 0.0013 | 59 |
| YW-220 | MC9(D-NMeY147, NMeL149, | (D-NMeTyr)-Phe-NMeLeu-Pro(4Ph)-(D-Ser)- | 1328.6 [M + H]⁺ | 1328.51 | 15.67 | | 0.00067 | 60 |

TABLE 2-continued

List of embodiments

| Poly-peptide No. | | Sequence | Mw (obs.) [M + 2H]⁺/2 | Mw (cal.) | Rt (min.) HPLC | HPLC purity analysis conditions | EC$_{50}$ (μM) | SEQ ID NO: |
|---|---|---|---|---|---|---|---|---|
| | Pro(4Ph)150, D-S151, 2Nal153, D-A154, Tic155, NMeS156) | Gln-2Nal-(D-Ala)-Tic-(NMe-Ser) | | | | | | |
| YW-221 | MC9(DY(3F)147, NMeL149, Pro(4Ph)150, D-S151, 2Nal153, D-A154, Tic155, NMeS156) | [D-Tyr(3F)]-Phe-(NMe-Leu)-Pro-(4Ph)-(D-Ser)-Gln-2Nal-(D-Ala)-Tic-(NMe-Ser) | 667.0 | 1332.47 | 15.88 | J | 0.00068 | 61 |
| YW-222 | MC9(DY(3F)147, NMeL149 Pro(4Ph)150, D-S151, 2Nal153, D-A154, Tic155) | [D-Tyr(3F)]-Phe-(NMe-Leu)-Pro-(4Ph)-(D-Ser)-Gln-2Nal-(D-Ala)-TicSer | 660.3 | 1318.44 | 15.82 | J | 0.00034 | 62 |
| YW-223 | MC9(Palm-PEG, Gly145, Gly146, DY147, NMeL149, Pro(4Ph)150, D-S151, 2Nal153, D-A154, Tic155) | Palm-PEG-Gly-Gly-(D-Tyr)-Phe-NMeLeu-Pro-(4Ph)-(D-Ser)-Gln-2Nal-(D-Ala)-Tic-Ser | 693.0 | 2076.48 | 16.18 | M | 0.00033 | 63 |
| YW-224 | MC9(DY147, NMeL149, Pro(diF)150, D-S151, 2Nal153, D-A154, Tic155, NMeS156) | (D-Tyr)-Phe-(NMe-Leu)-Pro(diF)-(D-Ser)-Gln-2Nal-(D-Ala)-Tic-NMeSer | 667.0 | 1332.47 | 16.25 | J | 0.0013 | 64 |
| YW-225 | MC9(DNMeY147, NMeL149, Pro(diF)150, D-S151, 2Nal153, D-A154, Tic155, NMeS156) | (D-NMeTyr)-Phe-NMeLeu-Pro(diF)-(D-Ser)-Gln-2Nal-(D-Ala)-Tic-(NMe-Ser) | 674.0 | 1346.5 | 16.11 | J | 0.00064 | 65 |
| YW-226 | MC9(DY(3F)147, NMeL149, Pro(diF)150, D-S151, 2Nal15346, D-A154, Tic155, Ser) NMeS156) | [D-Tyr(3F)]-Phe-NMeLeu-Pro(diF)-(D-Ser)-Gln-2Nal-(D-Ala)-Tic-(NMe- | 676.0 | 1350.46 | 16.46 | J | 0.0033 | 66 |
| YW-96 | MC9(D-Tyr147, S-Pip150, D-S151, D-A154, Tic155) | (D-Tyr)-Phe-Leu-(S-Pip)-(D-Ser)-Gln-Phe-(D-Ala)-Tic-Ser | 1233.6 [M + H]⁺ | 1232.38 | 15.70 | C | 0.0390 | 67 |
| YW-97 | MC9(D-F147, D-S151, D-A154, Tic155) | (D-Phe)-Phe-Leu-Pro-(D-Ser)-Gln-Phe-(D-Ala)-Tic-Ser | 1202.36 | 602.2 | 15.34 | C | 0.0500 | 68 |
| YW-103 | MC9(D-NMeY147, D-S151, D-A154, Tic155) | (D-NMe-Tyr)-Phe-Leu-Pro-(D-Ser)-Gln-Phe-(D-Ala)-Tic-Ser | 617.0 | 1232.38 | 14.87 | C | 0.0094 | 69 |
| YW-104 | MC9(D-Y147, NMeF148, D- | (D-Tyr)-(NMe-Phe)-Leu-Pro-(D- | 617.0 | 1232.38 | 15.21 | C | 0.0800 | 70 |

TABLE 2-continued

List of embodiments

| Poly-peptide No. | | Sequence | Mw (obs.) [M + 2H]+/2 | Mw (cal.) | Rt (min.) HPLC | HPLC purity analysis conditions | EC$_{50}$ (µM) | SEQ ID NO: |
|---|---|---|---|---|---|---|---|---|
| | S151, D-A154, Tic155) | Ser)-Gln-Phe-(D-Ala)-Tic-Ser | | | | | | |
| YW-110 | MC9(D-Y147, D-S151, D-A154, Tic155, NMeS156) | (D-Tyr)-Phe-Leu-Pro-(D-Ser)-Gln-Phe-(D-Ala)-Tic-(NMe-Ser) | 617.0 | 1232.38 | 15.35 | C | 0.013 | 71 |
| YW-112 | MC9(D-Y147, Pro(5Ph)150, D-S151, D-A154, Tic155) | (D-Tyr)-Phe-Leu-Pro(5-phenyl)-(D-Ser)-Gln-Phe-(D-Ala)-Tic-Ser | 648.2 | 1294.45 | 17.12 | C | 0.1700 | 72 |
| YW-113 | MC9(D-Y147, Pro(4Ph)150, D-S151, D-A154, Tic155) | (D-Tyr)-Phe-Leu-Pro(4-phenyl)-(D-Ser)-Gln-Phe-(D-Ala)-Tic-Ser | 648.0 | 1294.45 | 17.25 | C | 0.0086 | 73 |
| YW-114 | MC9(D-Y147, Thz150, D-S151, D-A154, Tic155) | (D-Tyr)-Phe-Leu-Thz-(D-Ser)-Gln-Phe-(D-Ala)-Tic-Ser | 619.2 | 1236.39 | 15.44 | C | 0.0050 | 74 |
| YW-115 | MC9(D-Y147, Aze150, D-S151, D-A154, Tic155) | (D-Tyr)-Phe-Leu-Aze-(D-Ser)-Gln-Phe-(D-Ala)-Tic-Ser | 603.0 | 1204.33 | 15.08 | C | 0.1900 | 75 |
| YW-117 | MC9(D-Y147, D-S151, 1Nal153, D-A154, Tic155) | (D-Tyr)-Phe-Leu-Pro-(D-Ser)-Gln-1Nal-(D-Ala)-Tic-Ser | 635.0 | 1267.59 | 16.33 | C | 0.0039 | 76 |
| YW-118 | MC9(D-Y147, D-S151, 2Nal153, D-A154, Tic155) | (D-Tyr)-Phe-Leu-Pro-(D-Ser)-Gln-2Nal-(D-Ala)-Tic-Ser | 635.0 | 1268.41 | 16.36 | C | 0.0069 | 77 |
| YW-119 | MC9(D-Y147, D-S151, Bpa153, D-A154, Tic155) | (D-Tyr)-Phe-Leu-Pro-(D-Ser)-Gln-Bpa-(D-Ala)-Tic-Ser | 662.0 | 1322.46 | 16.31 | C | 0.0099 | 78 |
| YW-149 | MC9(D-Y147, D-S151, D-A154, D-Tic155) | (D-Tyr)-Phe-Leu-Pro-(D-Ser)-Gln-Phe-(D-Ala)-(D-Tic)-Ser | 610.2 | 1218.36 | 16.53 | J | 0.0210 | 79 |
| YW-150 | MC9(D-Y147, D-S151, D-A154, Ti1c155) | (D-Tyr)-Phe-Leu-Pro-(D-Ser)-Gln-Phe-(D-Ala)-Ti1c-Ser | 610.0 | 1218.36 | 17.19 | J | 0.0620 | 80 |
| YW-151 | MC9(D-Y147, D-S151, D-A154, D-Ti1c155) | (D-Tyr)-Phe-Leu-Pro-(D-Ser)-Gln-Phe-(D-Ala)-(D-Ti1c)-Ser | 610.2 | 1218.36 | 16.46 | J | 0.0270 | 81 |
| YW-154 | MC9(D-NMeY147, D-S151, D-A154, D-Ti1c155) | (D-NMe-Tyr)-Phe-Leu-Pro-(D-Ser)-Gln-Phe-(D-Ala)-(D-Ti1c)-Ser | 617.0 | 1232.38 | 10.10 | L | 0.0340 | 82 |
| YW-158 | MC9(D-Y147, D-S151, D-A154, TP5C155) | (D-Tyr)-Phe-Leu-Pro-(D-Ser)-Gln-Phe-(D-Ala)-TP5C-Ser | 612.9 | 1224.38 | 17.09 | J | 0.0650 | 83 |
| YW-159 | MC9(D-Y147, D-S151, D-A154, TP6C155) | (D-Tyr)-Phe-Leu-Pro-(D-Ser)-Gln-Phe-(D-Ala)-TP6C-Ser | 613.0 | 1224.38 | 17.16 | J | 0.0180 | 84 |

TABLE 2-continued

List of embodiments

| Poly-peptide No. | | Sequence | Mw (obs.) [M + 2H]⁺/2 | Mw (cal.) | Rt (min.) HPLC | HPLC purity analysis conditions | EC₅₀ (μM) | SEQ ID NO: |
|---|---|---|---|---|---|---|---|---|
| YW-189 | MC9(D-Y147, D-S151, D-A154, Tic155, NH2) | (D-Tyr)-Phe-Leu-Pro-(D-Ser)-Gln-Phe-(D-Ala)-Tic-Ser-NH2 | 609.6 | 1217.37 | 13.92 | J | 0.0068 | 85 |
| YW-196 | MC9(D-Y147, Nva149, D-S151, D-A154, Tic155) | (D-Tyr)-Phe-Nva-Pro-(D-Ser)-Gln-Phe-(D-Ala)-Tic-Ser | 1204.6 [M + H]⁺ | 1204.33 | 14.41 | J | 0.039 | 86 |
| YW-197 | MC9(D-Y147, Nle149, D-S151, D-A154, Tic155) | (D-Tyr)-Phe-Nle-Pro-(D-Ser)-Gln-Phe-(D-Ala)-Tic-Ser | 1219.6 [M + H]⁺ | 1218.36 | 14.52 | J | 0.01 | 87 |
| YW-71 | MC9(3PPA, D-Y147, D-S151, D-A154, Tic155) | (3-Phenylpropanoyl)-(D-Tyr)-Phe-Leu-Pro-(D-Ser)-Gln-Phe-(D-Ala)-Tic-Ser | 676.1 | 1350.51 | 15.45 | I | 0.0310 | 88 |
| YW-72 | MC9[phenethyl carbamoyl-D-Y147, D-S151, D-A154, Tic155] | (Phenethylcarbamoyl)-(D-Tyr)-Phe-Leu-Pro-(D-Ser)-Gln-Phe-(D-Ala)-Tic-Ser | 683.5 | 1363.56 | 15.32 | I | 0.0450 | 89 |
| YW-73 | MC9[phenethyl-carbamothioyl-D-Y147, D-S151, D-A154, Tic155] | (Phenethyl-carbamothioyl)-D-Tyr)-Phe-Leu-Pro-(D-Ser)-Gln-Phe-(D-Ala)-Tic-Ser | 691.5 | 1381.59 | 16.45 | I | 0.0280 | 90 |
| YW-74 | MC9(3-phenyl-propyl-D-Y147, D-S151, D-A154, Tic155) | 3-Phenylpropyl-(D-Tyr)-Phe-Leu-Pro-(D-Ser)-Gln-Phe-(D-Ala)-Tic-Ser | 669.2 | 1336.53 | 10.55 | I | 0.0062 | 91 |
| YW-75 | MC9(4PhBA, D-Y147, D-S151, D-A154, Tic155) | (4-Phenylbutanoyl)-(D-Tyr)-Phe-Leu-Pro-(D-Ser)-Gln-Phe-(D-Ala)-Tic-Ser | 683.0 | 1364.54 | 15.97 | I | 0.0500 | 92 |
| YW-76 | MC9(5PhVA, D-Y147, D-S151, D-A154, Tic155) | (5-Phenylpentanoyl)-(D-Tyr)-Phe-Leu-Pro-(D-Ser)-Gln-Phe-(D-Ala)-Tic-Ser | 690.1 | 1378.57 | 16.60 | I | 0.0430 | 93 |
| YW-77 | MC9(4BPhAA, D-Y147, D-S151, D-A154, Tic155) | (4-Biphenylacetyl)-(D-Tyr)-Phe-Leu-Pro-(D-Ser)-Gln-Phe-(D-Ala)-Tic-Ser | 706.9 | 1412.58 | 17.10 | I | 0.0530 | 94 |
| YW-78 | MC9(DPhAA, D-Y147, D-S151, D-A154, Tic155) | (Diphenylacetyl)-(D-Tyr)-Phe-Leu-Pro-(D-Ser)-Gln-Phe-(D-Ala)-Tic-Ser | 707.0 | 1412.58 | 16.80 | I | 0.0260 | 95 |
| YW-79 | MC9(35HBA, D-Y147, D-S151, D-A154, | (3,5-Dihydroxybenzoyl)-(D-Tyr)-Phe- | 678.0 | 1354.46 | 12.98 | I | 0.0047 | 96 |

TABLE 2-continued

List of embodiments

| Poly-peptide No. | | Sequence | Mw (obs.) [M + 2H]⁺/2 | Mw (cal.) | Rt (min.) HPLC | HPLC purity analysis conditions | EC$_{50}$ (μM) | SEQ ID NO: |
|---|---|---|---|---|---|---|---|---|
| | Tic155) | Leu-Pro-(D-Ser)-Gln-Phe-(D-Ala)-Tic-Ser | | | | | | |
| YW-127 | MC9(23HBA, D-Y147, D-S151, D-A154, Tic155) | 2,3-Dihydroxybenzoyl-(D-Tyr)-Phe-Leu-Pro-(D-Ser)-Gln-Phe-(D-Ala)-Tic-Ser | 678.0 | 1354.46 | 14.90 | E | 0.0100 | 97 |
| YW-128 | MC9(26BA, D-Y147, D-S151, D-A154, Tic155) | 2,6-Dihydroxybenzoyl-(D-Tyr)-Phe-Leu-Pro-(D-Ser)-Gln-Phe-(D-Ala)-Tic-Ser | 678.2 | 1354.46 | 13.67 | L | 0.0200 | 98 |
| YW-129 | MC9(234HBA, D-Y147, D-S151, D-A154, Tic155) | 2,3,4-Trihydroxybenzoyl-(D-Tyr)-Phe-Leu-Pro-(D-Ser)-Gln-Phe-(D-Ala)-Tic-Ser | 686.0 | 1370.46 | 13.81 | E | 0.0091 | 99 |
| YW-131 | MC9(35HPA, D-Y147, D-S151, D-A154, Tic155) | 3,5-Dihydroxy-phenylacetyl-(D-Tyr)-Phe-Leu-Pro-(D-Ser)-Gln-Phe-(D-Ala)-Tic-Ser | 684.7 | 1368.51 | 15.88 | A | 0.0029 | 100 |
| YW-132 | MC9(34HPA, D-Y147, D-S151, D-A154, Tic155) | 3,4-Dihydroxy-phenylacetyl-(D-Tyr)-Phe-Leu-Pro-(D-ser)-Gln-Phe-(D-Ala)-Tic-Ser | 685.0 | 1368.49 | 12.06 | L | 0.0055 | 101 |
| YW-90 | MC9(D-Y147, D-S151, D-A154, S-Pip155) | (D-Tyr)-Phe-Leu-Pro-(D-Ser)-Gln-Phe-(D-Ala)-(S-Pip)-Ser | 586.0 | 1170.31 | 8.57 | I | >50 | 103 |
| YW-91 | MC9[D-Y147, D-S151, D-A154, Pro(5Ph)155] | (D-Tyr)-Phe-Leu-Pro-(D-Ser)-Gln-Phe-(D-Ala)-Pro(5-phenyl)-Ser | 617.0 | 1232.38 | 15.31 | C | 0.4600 | 104 |
| YW-92 | MC9(D-Y147, D-S151, D-A154, Pro(4Ph)155) | (D-Tyr)-Phe-Leu-Pro-(D-Ser)-Gln-Phe-(D-Ala)-Pro(4-phenyl)-Ser | 616.9 | 1232.32 | 15.80 | C | 1.0000 | 105 |
| YW-93 | MC9(D-Y147, D-S151, D-A154, Ical55) | (D-Tyr)-Phe-Leu-Pro-(D-Ser)-Gln-(D-Ala)-[(S)-isoindoline-1-carboxylic acid]-Ser | 603.0 | 1204.33 | P1: 14.45 P2: 16.50 | P1: C P2: J | 0.5700 | 106 |
| YW-94 | MC9[D-Y147, D-S151, D-A154, Ala(dip)155] | (D-Tyr)-Phe-Leu-Pro-(D-Ser)-Gln-Phe-(D-Ala)-Ala(dip)-Ser | 642.2 | 1282.44 | 16.18 | C | 8.7000 | 107 |
| YW-95 | MC9(D-Y147, D-S151, D-A154, Bip155) | (D-Tyr)-Phe-Leu-Pro-(D-Ser)-Gln-Phe-(D-Ala)-Bip-Ser | 642.0 | 1282.44 | 17.02 | C | 30.000 | 108 |

TABLE 2-continued

List of embodiments

| Polypeptide No. | | Sequence | Mw (obs.) [M + 2H]⁺/2 | Mw (cal.) | Rt (min.) HPLC | HPLC purity analysis conditions | EC$_{50}$ (μM) | SEQ ID NO: |
|---|---|---|---|---|---|---|---|---|
| YW-99 | MC9(D-Y147, NMeV149, D-S151, D-A154, Tic155) | (D-Tyr)-Phe-(NMe-Val)-Pro-(D-Ser)-Gln-Phe-(D-Ala)-Tic-Ser | 1219.7 [M + H]⁺ | 1218.36 | 14.11 | C | 12.000 | 109 |
| YW-102 | MC9(D-Y147, Nleu149, D-S151, D-A154, Tic155) | (D-Tyr)-Phe-NLeu-Pro-(D-Ser)-Gln-Phe-(D-Ala)-Tic-Ser | 609.9 | 1218.36 | 15.81 | C | 0.3100 | 110 |
| YW-106 | MC9(D-Y147, D-NMeS151, D-A154, Tic155) | (D-Tyr)-Phe-Leu-Pro-(NMe-D-Ser)-Gln-Phe-(D-Ala)-Tic-Ser | 617.0 | 1232.38 | 15.60 | C | 24.000 | 111 |
| YW-107 | MC9(D-Y147, D-S151, NMeQ152, D-A154, Tic155) | (D-Tyr)-Phe-Leu-Pro-(D-Ser)-(NMe-Gln)-Phe-(D-Ala)-Tic-Ser | 617.0 | 1232.38 | 15.93 | C | >50 | 112 |
| YW-108 | MC9(D-Y147, D-S151, NGln152, D-A154, Tic155) | (D-Tyr)-Phe-Leu-Pro-(D-Ser)-NGln-Phe-(D-Ala)-Tic-Ser | 610.0 | 1218.36 | 15.56 | C | >50 | 113 |
| YW-109 | MC9(D-Y147, D-S151, D-NMeA154, Tic155) | (D-Tyr)-Phe-Leu-Pro-(D-Ser)-Gln-Phe-(NMe-D-Ala)-Tic-Ser | 617.0 | 1232.38 | 14.25 | C | 11.000 | 114 |
| YW-147 | MC9(D-Y147, D-S151, D-S153, D-A154, azaTic155) | (D-Tyr)-Phe-Leu-Pro-(D-Ser)-Gln-(D-Ser)-(D-Ala)-azaTic-Ser | 580.6 | 1159.25 | 15.02 | J | >50 | 115 |
| YW-155 | MC9(D-Y147, D-S151, D-A154, D-Tilc155, NMeS156) | (D-Tyr)-Phe-Leu-Pro-(D-Ser)-Gln-Phe-(NMe-D-Ala)-(D-Tilc)-(NMe-Ser) | 617.0 | 1232.38 | 10.22 | L | 15.500 | 116 |
| YW-156 | MC9(D-Y147, 2Nal151, D-A154, D-Tilc155) | (D-Tyr)-Phe-Leu-Pro-2Nal-Gln-Phe-(D-Ala)-(D-Tilc)-Ser | 665.0 | 1328.51 | 13.82 | L | no fit | 117 |
| YW-157 | MC9(D-Y147, 1Nal151, D-A154, D-Tilc155) | (D-Tyr)-Phe-Leu-Pro-1Nal-Gln-Phe-(D-Ala)-(D-Tilc)-Ser | 665.0 | 1328.51 | 13.79 | L | no fit | 118 |

TABLE 2-continued

List of embodiments

| Poly-peptide No. | | Sequence | Mw (obs.) $[M + 2H]^+/2$ | Mw (cal.) | Rt (min.) HPLC | HPLC purity analysis conditions | $EC_{50}$ (µM) | SEQ ID NO: |
|---|---|---|---|---|---|---|---|---|
| YW-160 | MC9(D-Y147, D-S151, D-A154, Tic155, T156) | (D-Tyr)-Phe-Leu-Pro-(D-Ser)-Gln-Phe-(D-Ala)-Tic-Thr | 617.0 | 1232.38 | 15.56 | J | 0.2850 | 119 |

The purity analysis conditions in Table 2 are as follows:

Condition A: Eluent A/B=95/5-35/65
Mobile phase: A: water (0.01% TFA), B: ACN (0.01% TFA)
Mobile phase ratio: 5% B within 0-3 min, linear gradient elution 5-65% B within 20 min
Flow rate: 1.2 mL/min
Column: Eclipse XDB-C18, 4.6*150 mm, 5 µm
Box temperature: 40° C.

Condition B: Eluent A/B=95/5-35/65
Mobile phase: A: water (0.01% TFA), B: ACN (0.01% TFA)
Mobile phase ratio: 5% B within 0-3 min, linear gradient elution 5-65% B within 20 min
Flow rate: 1.0 mL/min
Column: AGLIENT ZORBAX Eclipse XDB, C18, 4.6*150 mm, 5 µm
Temperature: 40° C.

Condition C: Eluent A/B=95/5-35/65
Mobile phase: A: water (0.01% TFA), B: ACN (0.01% TFA)
Mobile phase ratio: 5% B within 0-3 min, linear gradient elution 5-65% B with 20 min
Flow rate: 1.0 mL/min
Column: SunFire C18, 4.6*150 mm, 3.5 µm
Temperature: 40° C.

Condition D: Eluent A/B=95/5-35/65
Mobile phase: A: water (0.05% TFA), B: ACN (0.05% TFA)
Mobile phase ratio: 5% B within 0-3 min, linear gradient elution 5-65% B within 20 min
Flow rate: 1.2 mL/min
Column: Eclipse XDB-C18, 4.6*150 mm, 5 µm Condition E: Eluent A/B=85/15-25/75
Mobile phase: A: water (0.01% TFA), B: ACN (0.01% TFA)
Mobile phase ratio: 15% B within 0-3 min, linear gradient elution 15-75% B with 20 min
Flow rate: 1.0 mL/min
Column: SunFire C18, 4.6*150 mm, 3.5 µm
Temperature: 40° C.

Condition F: Eluent A/B=95/5-35/65
Mobile phase: A: water (0.05% TFA), B: ACN (0.05% TFA)
Mobile phase ratio: 5% B within 0-3 min, linear gradient elution 5-65% B within 20 min
Flow rate: 1.2 mL/min
Column: SunFire C18, 4.6*150 mm, 3.5 µm Condition G: Eluent A/B=80/20-20/80
Mobile phase: A: water (0.01% TFA), B: ACN (0.01% TFA)
Mobile phase ratio: 20% B within 0-3 min, linear gradient elution 20-80% B with 20 min
Flow rate: 1.0 mL/min
Column: SunFire C18, 4.6*150 mm, 3.5 µm
Temperature: 40° C.

Condition H: Eluent A/B=50/50-0/100
Mobile phase: A: water (0.05% TFA), B: ACN (0.05% TFA)
Mobile phase ratio: 50% B within 0-3 min, linear gradient elution 50-100% B within 20 min
Flow rate: 1.0 mL/min
Column: XBridge Peptide BEH C18, 4.6*150 mm, 3.5 µm
Column temperature: 40° C.

Condition I: Eluent A/B=80/20-5/95
Mobile phase: A: water (0.01% TFA), B: ACN (0.01% TFA)
Mobile phase ratio: 20% B within 0-2 min, linear gradient elution 20-95% B within 25 min
Flow rate: 1.0 mL/min
Column: SunFire C18, 4.6*150 mm, 3.5 µm
Column temperature: 40° C.

Condition J: Eluent A/B=95/5-35-65
Mobile phase: water (0.05% TFA), B: ACN (0.05% TFA)
Mobile phase ratio: 5% B within 0-3 min, linear gradient elution 5-65% B within 20 min
Flow rate: 1.0 mL/min
Column: XBridge Peptide BEH C18, 4.6*150 mm, 3.5 µm
Column temperature: 40° C.

Condition K: Eluent A/B=50/50-0/100
Mobile phase: A: A: water (0.01% TFA), B: ACN (0.01% TFA)
Mobile phase ratio: 50% B within 0-3 min, linear gradient elution 50-100% B within 20 min
Flow rate: 1.0 mL/min
Column: SunFire C18, 4.6*150 mm, 3.5 µm
Column temperature: 40° C.

Condition L: Eluent A/B=80/20-5/95
Mobile phase: A: water (0.05% TFA), B: ACN (0.05% TFA)
Mobile phase ratio: 20% B within 0-2 min, linear gradient elution 20-95% B within 25 min
Flow rate: 1.0 mL/min
Column: XBridge Peptide BEH, 4.6*150 mm, 3.5 µm
Column temperature: 40° C.

Condition M: Eluent A/B=80/20-20/80
Mobile phase: A: water (0.05% TFA), B: ACN (0.05% TFA)
Mobile phase ratio: 20% B within 0-1 min, linear gradient elution 20-80% B within 20 min
Flow rate: 1.0 mL/min
Column: XBridge Peptide BEH C18, 4.6*150 mm, 3.5 µm
Column temperature: 40° C.

Condition N: Eluent A/B=70/30-0/100
Mobile phase: A: water (0.05% TFA), B: ACN (0.05% TFA)
Mobile phase ratio: 30% B within 0-3 min, linear gradient elution 30-100% B within 20 min
Flow rate: 1.0 mL/min
Column temperature: 40° C.
Column: XBridge Peptide BEH C18, 4.6*150 mm, 3.5 µm Effect Embodiment 1: Pharmacological Experimental Data The polypeptide sequences described above are the polypeptide sequences disclosed in the patent JP2010-229093A of BANYU PHARMA CO LTD: (D-Tyr)-Phe-Leu-Pro-(D-Ser)-Gln-Phe-(D-Ala)-Tic-Ser was used as a positive control (SEQ ID NO: 102).

Day 2: Dosing and Testing

1. Preparation of 200× Compound Plate 1.1 The test compound was formulated into a 10 mM working solution in DMSO.

1.2 45 µL of 10 mM test compound was added to the $2^{nd}$ column of rows A to P in the Echo-384 well plate. The compound was subjected to a 3-fold dilution with Precision (30 µL of DMSO was added to the $3^{rd}$ to $11^{th}$ columns; 15 µL of the drug solution was pipetted from the $2^{nd}$ column to the $3^{rd}$ column, blown and evenly mixed; then 15 µL of the drug solution was pipetted from the $3^{rd}$ column to the $4^{th}$ column, blown and evenly mixed; the drugs was subjected to a 3-fold dilution to obtain 10 concentrations in total). The $1^{st}$ and $12^{th}$ columns of the Echo-384 well plate were supplemented with 30 µL of DMSO. The concentrations of the drugs in each well in the $2^{nd}$ to $11^{th}$ columns of 200× compound plate were shown in following Table 3.

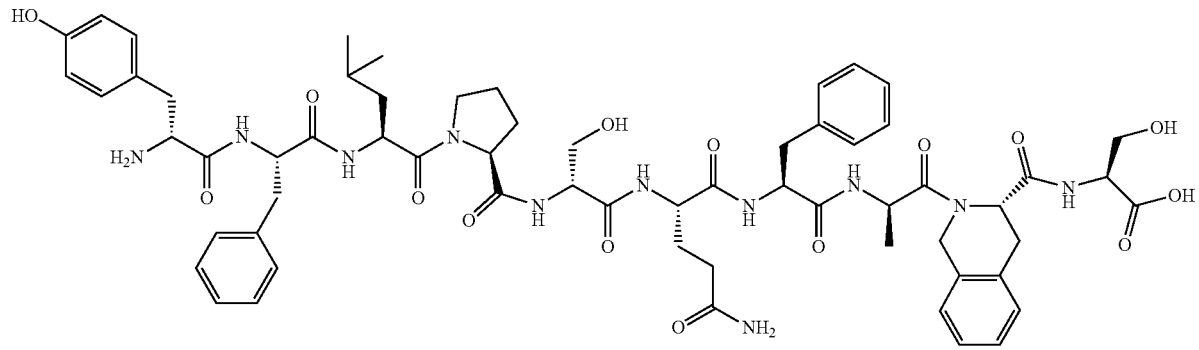 [SMILES: CC(C)C[C@H](NC(=O)[C@H](Cc1ccccc1)NC(=O)[C@H](N)Cc1ccc(O)cc1)C(=O)N1CCC[C@H]1C(=O)N[C@H](CO)C(=O)N[C@@H](CCC(N)=O)C(=O)N[C@@H](Cc1ccccc1)C(=O)N[C@H](C)C(=O)N1Cc2ccccc2C[C@H]1C(=O)N[C@@H](CO)C(=O)O]

The activation of the compound on Tango™ CMKLR1-bla U2OS cells (Invitrogen Cat. nos. K1551) was tested.

The activation of each compound in the above experiments on Tango™ CMKLR1-bla U2OS cells was determined as follows:

Day 1: Cell Seeding on Plate

1. The cells were observed under the microscope (CKX41, OLYMPUS, 4× objective lens, 10× eyepiece) and the state of the cells was determined to be good.

2. The medium was removed, and the cells were washed with DPBS twice, followed by addition of 3 mL of 0.05% trypsin, and placed in a 37° C., 5% $CO_2$ incubator (Thermo Fisher, Waltham, Massachusetts, USA) for 3-5 minutes. After the cells were rounded, 3-5 mL of medium (medium formula: DMEM 90%, Dialyzed FBS 10%, NEAA 0.1 mM, HEPES (pH 7.3) 25 mM, Penicillin 100 U/mL, Streptomycin 100 µg/mL) was added to terminate digestion.

2. The digested cells were transferred to a 15 mL centrifuge tube (430790, Corning), centrifuged at 1000 rpm for 5 minutes (5810R, Eppendorf, Hamburg, Germany), and the supernatant was discarded.

3. 7 mL of medium (DMEM+10% FBS) was added, blowed into a single cell suspension, counted by a cell counter, and adjusted the cell suspension to a desired cell density of 250,000/mL with the medium.

4. The cell suspension was seeded into a 384-well cell plate (Corning 3712) in 40 µL/well to make the number of cells 10000 cells/well, and 32 µL of medium was added to the blank control.

5. The incubation was performed overnight at 37° C. under 5% $CO_2$.

TABLE 3

Concentrations of the drugs in each well of the $2^{nd}$ to $11^{th}$ columns of 200 × compound plate

| | Column No. | | | | | | | | | |
|---|---|---|---|---|---|---|---|---|---|---|
| | 2 | 3 | 4 | 5 | 6 | 7 | 8 | 9 | 10 | 11 |
| Concentration (µm) | 10000 | 3333 | 1111 | 370 | 123 | 41 | 13 | 4.6 | 1.5 | 0.5 |

2. Preparation of Intermediate Plate 500 nL, i.e., 0.5 µL of the diluted compound (or DMSO) in the 200× compound plate was transferred into the corresponding position of V-bottom 384-well plate with Echo. 20 µL of medium was added to each well, centrifuged, shaken and evenly mixed. The concentration of the drugs in each well of the $2^{nd}$ to $11^{th}$ column of intermediate plate (i.e., 5× compound plate) were shown in following Table 4.

TABLE 4

Concentration of the drugs in each well of the $2^{nd}$ to $11^{th}$ column of 5 × compound plate

| | Column No. | | | | | | | | | |
|---|---|---|---|---|---|---|---|---|---|---|
| | 2 | 3 | 4 | 5 | 6 | 7 | 8 | 9 | 10 | 11 |
| Concentration (µm) | 250 | 83.3 | 27.8 | 9.3 | 3.1 | 1.0 | 0.34 | 0.11 | 0.04 | 0.01 |

3. Dosing 3.1 The cell plate was taken out from the incubator and observed under a microscope. The diluted compound or DMSO in the intermediate plate was added to the cell plate in 10 μL/well in the corresponding cell plate, and 40 μL of medium was pre-filled in each well.

3.2 The cells were incubated at 37° C. under 5% $CO_2$ for 4 hours.

TABLE 5

Concentration of the drugs in each well of the $2^{nd}$ to $11^{th}$ column of 1 × compound plate

| | | | | | Column No. | | | | | |
|---|---|---|---|---|---|---|---|---|---|---|
| | 2 | 3 | 4 | 5 | 6 | 7 | 8 | 9 | 10 | 11 |
| Concentration (μm) | 50 | 16.7 | 5.6 | 1.9 | 0.62 | 0.21 | 0.07 | 0.02 | 0.008 | 0.003 |

4. Activation Detection 4.1 1 mM CCF4-AM, solution B, Solution C, and Solution D were used to prepare an appropriate amount of 6× detection solution. The LiveBLAzer™-FRET B/G Loading kit (K1095, Thermo Fisher, Waltham, Massachusetts, USA) kit containing CCF-4AM and solutionB, solutionC, and solutionD was also purchased from invitrogen (K1157, Thermo Fisher, Waltham, Massachusetts, USA).

4.2 The cells were observed under a microscope and the cell plate was equilibrated to room temperature.

4.3 6 μL of CCF-4AM dissolved solution A, 60 μL of solution B, 904 μL of solution C and 30 μL of solution D were pipetted in an EP tube, blown, and evenly mixed to obtain a 6× detection solution. The prepared 6× detection solution was pipetted to a 384-well plate in 10 μL/well.

4.4 The cell plate was centrifuged at 1000 rpm, shaken on a shaker at 450 rpm for 1 minutes, and then allowed to stand at room temperature for 1.5 hours.

4.5 The fluorescence signal of each well was detected by the Enspire microplate detector, ($\lambda$ex=409 nm, $\lambda$em=460/530 nm) to read the signal value.

5. XLfit (5.4.0.8, ID Business Solutions Limited) was used to Process the Data.

Data processing: activation rate=(Signal−Min)/(Max−Min)*100%

Max: The background value at which human Chemokine like receptor 1 is activated after the addition of a high concentration of a positive drug.

Min: The background value when the cells are not affected by the compound.

Signal: The signal value of the compound at the corresponding concentration.

A four-parameter curve fit was performed with the compound concentration and the corresponding activation rate to obtain the $EC_{50}$ of the corresponding compound.

The data was fitted using equations in the XLfit software.

TABLE 6

Biological activity results of compound in the pharmacological experiments

| Polypeptide No. | $EC_{50}$ (μM) |
|---|---|
| YW-71 | 0.031 |
| YW-72 | 0.045 |

TABLE 6-continued

Biological activity results of compound in the pharmacological experiments

| Polypeptide No. | $EC_{50}$ (μM) |
|---|---|
| YW-73 | 0.028 |
| YW-74 | 0.0062 |
| YW-75 | 0.05 |
| YW-76 | 0.043 |
| YW-77 | 0.053 |
| YW-78 | 0.026 |
| YW-79 | 0.0047 |
| YW-96 | 0.039 |
| YW-97 | 0.05 |
| YW-98 | 0.003 |
| YW-100 | 0.042 |
| YW-101 | 0.0029 |
| YW-103 | 0.0094 |
| YW-104 | 0.08 |
| YW-105 | 0.0106 |
| YW-110 | 0.013 |
| YW-111 | 0.002 |
| YW-112 | 0.17 |
| YW-113 | 0.0086 |
| YW-114 | 0.005 |
| YW-115 | 0.19 |
| YW-117 | 0.0039 |
| YW-118 | 0.0069 |
| YW-119 | 0.0099 |
| YW-121 | 0.0007 |
| YW-122 | 0.0006 |
| YW-124 | 0.0013 |
| YW-125 | 0.0006 |
| YW-127 | 0.01 |
| YW-128 | 0.02 |
| YW-129 | 0.0091 |
| YW-132 | 0.0055 |
| YW-133 | 0.0007 |
| YW-134 | 0.0007 |
| YW-142 | 0.0009 |
| YW-146 | 0.0014 |
| YW-147 | no fit |
| YW-148 | 0.0005 |
| YW-149 | 0.021 |
| YW-150 | 0.062 |
| YW-151 | 0.027 |
| YW-153 | 0.0085 |
| YW-154 | 0.034 |
| YW-158 | 0.065 |
| YW-159 | 0.018 |
| YW-161 | 0.003 |
| YW-162 | 0.0026 |
| YW-163 | 0.0022 |
| YW-164 | 0.0011 |
| YW-165 | 0.0015 |
| YW-166 | 0.005 |
| YW-167 | 0.0008 |
| YW-168 | 0.0012 |
| YW-171 | 0.029 |
| YW-172 | 0.0058 |
| YW-174 | 0.0012 |
| YW-175 | 0.091 |
| YW-176 | 0.0038 |
| YW-177 | 0.025 |
| YW-182 | 0.041 |
| YW-183 | 0.0092 |
| YW-184 | 0.016 |
| YW-185 | 0.0059 |
| YW-186 | 0.011 |
| YW-189 | 0.0068 |
| YW-190 | 0.0027 |
| YW-3 | 0.019 |

The $EC_{50}$ of some of the compounds listed in Table 6 is superior to YW-3, exhibiting strong activity, indicating that the compound of the present disclosure can effectively bind to the Chemerin receptor at the level of in vitro biochemical experiments. Therefore, the compound of the present disclosure can be an effective therapeutic drug for inflammation.

Effect Example 2: Plasma Stability Data of Some Compounds

1. Preparation of 50 mM Phosphate Buffer (50 mM Sodium Phosphate and 70 mM NaCl):

5.750 g of $Na_2HPO_4$, 1.141 g of $NaH_2PO_4$ and 4.095 g of NaCl (Shanghai Titan) were weighed and dissolved in 1000 mL of ultrapure water and the pH was adjusted to 7.4. The prepared phosphate buffer was stored in the refrigerator at 4° C., valid for one week.

2. Preparation of Compound Stock Solution:
   1) 5 mg/mL test compound: 5 mg of compound was weighed and dissolved in 1 mL of DMSO.
   2) 20 mM control: 2.728 mg of nococaine was dissolved in 0.5 mL of DMSO. 3.878 mg of fenfluramide was dissolved in 0.5 mL of DMSO (Amresco).

3. Preparation of Experimental Plasma:

The frozen plasma (human: Shanghai ChemPartner, Rat, Mouse: Shanghai Xipuer-Beikai, Dog, Monkey: Suzhou Xishan Zhongke) was taken out from the −80° C. refrigerator, immediately placed in a 37° C. water bath, and thawn with gentle shaking. The thawed plasma was poured into a centrifuge tube, and centrifuged at 3000 rpm for 8 minutes. The supernatant was collected for the experiment. The pH of the plasma was measured with a pH meter (METTLER TOLEDO), and only the plasma with a pH between 7.4 and 8 was used for the experiment. The plasma was placed on an ice bath for later use.

4. Preparation of the Dosing Solution:
   1) 125 µg/mL test compound solution: 5 µL of 5 mg/mL test compound (see step 2) was added to 195 µL DMSO; 500 µM control solution: 20 mM control stock solution (see step 2) was added to 195 µL DMSO.
   2) 0.5% BSA phosphate buffer solution: 0.05 g of BSA was added to 10 mL of phosphate buffer (see step 1).
   3) 5 µg/mL test compound dosing solution: 40 µL of 125 µg/mL test compound solution was added to 960 µL of 0.5% BSA phosphate buffer solution, shaken and mixed evenly, and the dosing solution was placed in a 37° C. water bath and preheated for 5 minutes.

20 µM control dosing solution: 40 µL of 500 µM control solution was added to 960 µL of 0.5% BSA phosphate buffer solution, shaken and mixed evenly, and the dosing solution was placed in a 37° C. water bath and preheated for 5 minutes.

5. 10 µL of 5 µg/mL test compound and 20 µM control solution were added to the wells of the 96-well plate set at different time points (0 minute, 1 hour, 2 hours and 4 hours). The number of duplicate samples was 3.

6. 500 µL of ACN (IS) containing 5% FA was added to the wells set at 0 minute. 90 µL of plasma was then added thereto, mixed evenly, sealed with the film and stored at 4° C. (the number of duplicates was 3).

7. 90 µL of plasma was added to the wells set at 1 hour, 2 hours and 4 hours (the number of replicates was 3), followed by timing (the final concentration of the test compound was 500 ng/mL, and that of the control was 2 µM).

8. Afterwards, when the timer showed 1 hour, 2 hours and 4 hours, 500 µL of ACN (IS) solution containing 5% FA was respectively added to the wells at the corresponding time point to terminate the reaction, mixed evenly, sealed with the film and stored at 4° C.

9. All samples (0 minutes, 1 hour, 2 hours, and 4 hours) at different time points on the 96-well plate were placed on a shaker (IKA, MTS 2/4) and shaken at 600 rpm for 60 minutes. The samples were then centrifuged for 15 minutes on a centrifuge machine (Thermo Multifuge×3R) at 5594×g.

10. 150 µL of the supernatant was taken out from the centrifuged sample and sent to LC-MS/MS for analysis (conventional peptide LC-MS/MS analysis).

TABLE 7

Experimental data of the plasma stability of the compounds

| Polypeptide No. | Human plasma ($T_{1/2}$ (h)) | Rat plasma ($T_{1/2}$ (h)) | Mouse plasma ($T_{1/2}$ (h)) |
| --- | --- | --- | --- |
| YW-3 | 12.81 | 11.66 | 35.35 |
| YW-111 | 71.05 | >71.05 | Very long |
| YW-122 | 79.64 | — | Very long |
| YW-125 | — | — | Very long |
| YW-133 | 13.72 | — | 67.08 |
| YW-134 | 14.03 | — | 11.36 |

Note
1: The term "Very long" in Table 7 means that no significant degradation of the plasma concentration of the polypeptide was found in the plasma stability test (4 hours).

What is claimed is:

1. A peptide compound I or a pharmaceutically acceptable salt thereof, wherein the compound I is (SEQ ID NO: 10)
(NMe-D-Tyr)-Phe-(NMe-Leu)-Thz-(D-Ser)-Gln-2Nal-
(D-Ala)-Tic-(NMe-Ser).

2. A pharmaceutical composition comprising the compound I or the pharmaceutically acceptable salt thereof of claim 1, and a pharmaceutically acceptable excipient.

* * * * *

SEQUENCE LISTING

```
<160> NUMBER OF SEQ ID NOS: 134

<210> SEQ ID NO 1
<211> LENGTH: 10
<212> TYPE: PRT
<213> ORGANISM: Artificial Sequence
<220> FEATURE:
<223> OTHER INFORMATION: Synthesized Peptide Compound YW-98
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
```

```
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 1

Tyr Phe Leu Pro Ser Gln Phe Ala Xaa Ser
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthesized Peptide Compound YW-100
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 2

Tyr Phe Phe Pro Ser Gln Phe Ala Xaa Ser
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthesized Peptide Compound YW-101
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe-Homoserine
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 3

Tyr Phe Leu Pro Ser Gln Phe Ala Xaa Ser
1               5                   10
```

```
<210> SEQ ID NO 4
<211> LENGTH: 10
<212> TYPE: PRT
<213> ORGANISM: Artificial Sequence
<220> FEATURE:
<223> OTHER INFORMATION: Synthesized Peptide Compound YW-105
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (2)..(2)
<223> OTHER INFORMATION: NMe
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 4

Tyr Phe Leu Pro Ser Gln Phe Ala Xaa Ser
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthesized Peptide Compound YW-111
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: BINDING
<222> LOCATION: (1)..(1)
<223> OTHER INFORMATION: 3-Phenylpropanoyl
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 5

Tyr Phe Leu Pro Ser Gln Phe Ala Xaa Ser
1               5                   10

<210> SEQ ID NO 6
<211> LENGTH: 10
<212> TYPE: PRT
```

```
<213> ORGANISM: Artificial Sequence
<220> FEATURE:
<223> OTHER INFORMATION: Synthesized Peptide Compound YW-121
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (4)..(4)
<223> OTHER INFORMATION: Thz
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 6

Tyr Phe Leu Xaa Ser Gln Phe Ala Xaa Ser
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthesized Peptide Compound YW-122
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (4)..(4)
<223> OTHER INFORMATION: Thz
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 2Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 7

Tyr Phe Leu Xaa Ser Gln Xaa Ala Xaa Ser
1               5                   10

<210> SEQ ID NO 8
<211> LENGTH: 10
<212> TYPE: PRT
<213> ORGANISM: Artificial Sequence
```

```
<220> FEATURE:
<223> OTHER INFORMATION: Synthesized Peptide Compound YW-123
<220> FEATURE:
<221> NAME/KEY: MISC_FEATURE
<222> LOCATION: (1)..(1)
<223> OTHER INFORMATION: NMe-D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (4)..(4)
<223> OTHER INFORMATION: Thz
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 8

Tyr Phe Leu Xaa Ser Gln Phe Ala Xaa Ser
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthesized Peptide Compound YW-124
<220> FEATURE:
<221> NAME/KEY: MISC_FEATURE
<222> LOCATION: (1)..(1)
<223> OTHER INFORMATION: NMe-D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (4)..(4)
<223> OTHER INFORMATION: Thz
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: NMe

<400> SEQUENCE: 9

Tyr Phe Leu Xaa Ser Gln Phe Ala Xaa Ser
1               5                   10

<210> SEQ ID NO 10
<211> LENGTH: 10
<212> TYPE: PRT
<213> ORGANISM: Artificial Sequence
<220> FEATURE:
```

```
<223> OTHER INFORMATION: Synthesized Peptide Compound YW-125
<220> FEATURE:
<221> NAME/KEY: MISC_FEATURE
<222> LOCATION: (1)..(1)
<223> OTHER INFORMATION: NMe-D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (4)..(4)
<223> OTHER INFORMATION: Thz
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 2Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: NMe

<400> SEQUENCE: 10

Tyr Phe Leu Xaa Ser Gln Xaa Ala Xaa Ser
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthesized Peptide Compound YW-133
<220> FEATURE:
<221> NAME/KEY: BINDING
<222> LOCATION: (1)..(1)
<223> OTHER INFORMATION: Palm-PEG8
<220> FEATURE:
<221> NAME/KEY: MISC_FEATURE
<222> LOCATION: (3)..(3)
<223> OTHER INFORMATION: D-amino acid
<220> FEATURE:
<221> NAME/KEY: MISC_FEATURE
<222> LOCATION: (5)..(5)
<223> OTHER INFORMATION: NMe
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (10)..(10)
<223> OTHER INFORMATION: D-amino acid
<220> FEATURE:
<221> NAME/KEY: MISC_FEATURE
<222> LOCATION: (11)..(11)
<223> OTHER INFORMATION: Tic

<400> SEQUENCE: 11

Gly Gly Tyr Phe Leu Pro Ser Gln Phe Ala Xaa Ser
1               5                   10

<210> SEQ ID NO 12
<211> LENGTH: 12
```

```
<212> TYPE: PRT
<213> ORGANISM: Artificial Sequence
<220> FEATURE:
<223> OTHER INFORMATION: Synthesized Peptide Compound YW-134
<220> FEATURE:
<221> NAME/KEY: BINDING
<222> LOCATION: (1)..(1)
<223> OTHER INFORMATION: Palm-PEG8
<220> FEATURE:
<221> NAME/KEY: MISC_FEATURE
<222> LOCATION: (1)..(1)
<223> OTHER INFORMATION: Beta-amino acid
<220> FEATURE:
<221> NAME/KEY: MISC_FEATURE
<222> LOCATION: (2)..(2)
<223> OTHER INFORMATION: Beta-amino acid
<220> FEATURE:
<221> NAME/KEY: MISC_FEATURE
<222> LOCATION: (3)..(3)
<223> OTHER INFORMATION: D-amino acid
<220> FEATURE:
<221> NAME/KEY: MISC_FEATURE
<222> LOCATION: (5)..(5)
<223> OTHER INFORMATION: NMe
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (10)..(10)
<223> OTHER INFORMATION: D-amino acid
<220> FEATURE:
<221> NAME/KEY: MISC_FEATURE
<222> LOCATION: (11)..(11)
<223> OTHER INFORMATION: Tic

<400> SEQUENCE: 12

Ala Ala Tyr Phe Leu Pro Ser Gln Phe Ala Xaa Ser
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthesized Peptide Compound YW-142
<220> FEATURE:
<221> NAME/KEY: MISC_FEATURE
<222> LOCATION: (1)..(1)
<223> OTHER INFORMATION: NMe-D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (4)..(4)
<223> OTHER INFORMATION: Thz
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 1Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
```

```
<222> LOCATION: (10)..(10)
<223> OTHER INFORMATION: NMe

<400> SEQUENCE: 13

Tyr Phe Leu Xaa Ser Gln Xaa Ala Xaa Ser
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthesized Peptide Compound YW-146
<220> FEATURE:
<221> NAME/KEY: MISC_FEATURE
<222> LOCATION: (1)..(1)
<223> OTHER INFORMATION: NMe-D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 2Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: NMe

<400> SEQUENCE: 14

Tyr Phe Leu Pro Ser Gln Xaa Ala Xaa Ser
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthesized Peptide Compound YW-148
<220> FEATURE:
<221> NAME/KEY: MISC_FEATURE
<222> LOCATION: (1)..(1)
<223> OTHER INFORMATION: D-amino acid-NMe
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (4)..(4)
<223> OTHER INFORMATION: Thz
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 2Nal
<220> FEATURE:
<221> NAME/KEY: MISC_FEATURE
<222> LOCATION: (8)..(8)
```

```
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 15

Tyr Phe Leu Xaa Ser Gln Xaa Ala Xaa Ser
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthesized Peptide Compound YW-153
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: D-Tilc

<400> SEQUENCE: 16

Tyr Phe Leu Pro Ser Gln Phe Ala Xaa Ser
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthesized Peptide Compound YW-161
<220> FEATURE:
<221> NAME/KEY: BINDING
<222> LOCATION: (1)..(1)
<223> OTHER INFORMATION: 3-Phenylpropanoyl
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: BINDING
<222> LOCATION: (10)..(10)
<223> OTHER INFORMATION: NH2
```

<400> SEQUENCE: 17

Tyr Phe Leu Pro Ser Gln Phe Ala Xaa Ser
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthesized Peptide Compound YW-162
<220> FEATURE:
<221> NAME/KEY: MISC_FEATURE
<222> LOCATION: (1)..(1)
<223> OTHER INFORMATION: D-amino acid-NMe
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 1Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: NMe

<400> SEQUENCE: 18

Tyr Phe Leu Pro Ser Gln Xaa Ala Xaa Ser
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthesized Peptide Compound YW-163
<220> FEATURE:
<221> NAME/KEY: MISC_FEATURE
<222> LOCATION: (1)..(1)
<223> OTHER INFORMATION: D-amino acid-NMe
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 19

Tyr Phe Leu Pro Ser Gln Phe Ala Xaa Ser
1               5                   10

```
<210> SEQ ID NO 20
<211> LENGTH: 10
<212> TYPE: PRT
<213> ORGANISM: Artificial Sequence
<220> FEATURE:
<223> OTHER INFORMATION: Synthesized Peptide Compound YW-164
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 2Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 20

Tyr Phe Leu Pro Ser Gln Xaa Ala Xaa Ser
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthesized Peptide Compound YW-165
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 1Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 21

Tyr Phe Leu Pro Ser Gln Xaa Ala Xaa Ser
1               5                   10

<210> SEQ ID NO 22
<211> LENGTH: 10
<212> TYPE: PRT
```

```
<213> ORGANISM: Artificial Sequence
<220> FEATURE:
<223> OTHER INFORMATION: Synthesized Peptide Compound YW-166
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: NMe

<400> SEQUENCE: 22

Tyr Phe Leu Pro Ser Gln Phe Ala Xaa Ser
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthesized Peptide Compound YW-167
<220> FEATURE:
<221> NAME/KEY: MISC_FEATURE
<222> LOCATION: (1)..(1)
<223> OTHER INFORMATION: D-amino acid-NMe
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 2Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 23

Tyr Phe Leu Pro Ser Gln Xaa Ala Xaa Ser
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthesized Peptide Compound YW-168
<220> FEATURE:
<221> NAME/KEY: MISC_FEATURE
```

```
<222> LOCATION: (1)..(1)
<223> OTHER INFORMATION: D-amino acid-NMe
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 1Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 24

Tyr Phe Leu Pro Ser Gln Xaa Ala Xaa Ser
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthesized Peptide Compound YW-171
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: Homoserine

<400> SEQUENCE: 25

Tyr Phe Leu Pro Ser Gln Phe Ala Xaa Ser
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthesized Peptide Compound YW-172
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
```

```
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: NHo

<400> SEQUENCE: 26

Tyr Phe Leu Pro Ser Gln Phe Ala Xaa Ser
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthesized Peptide Compound YW-174
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (4)..(4)
<223> OTHER INFORMATION: diF
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 27

Tyr Phe Leu Xaa Ser Gln Phe Ala Xaa Ser
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthesized Peptide Compound YW-175
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid-Homoserine
```

```
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 28

Tyr Phe Leu Pro Ser Gln Phe Ala Xaa Ser
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthesized Peptide Compound YW-176
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: D-amino acid-Oic

<400> SEQUENCE: 29

Tyr Phe Leu Pro Ser Gln Phe Ala Xaa Ser
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthesized Peptide Compound YW-177
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: NMe-Homoserine
```

```
<400> SEQUENCE: 30

Tyr Phe Leu Pro Ser Gln Phe Ala Xaa Xaa
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthesized Peptide Compound YW-178
<220> FEATURE:
<221> NAME/KEY: BINDING
<222> LOCATION: (1)..(1)
<223> OTHER INFORMATION: Palm-PEG8
<220> FEATURE:
<221> NAME/KEY: MISC_FEATURE
<222> LOCATION: (3)..(3)
<223> OTHER INFORMATION: D-amino acid-NMe
<220> FEATURE:
<221> NAME/KEY: MISC_FEATURE
<222> LOCATION: (5)..(5)
<223> OTHER INFORMATION: NMe
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (9)..(9)
<223> OTHER INFORMATION: 2Nal
<220> FEATURE:
<221> NAME/KEY: MISC_FEATURE
<222> LOCATION: (10)..(10)
<223> OTHER INFORMATION: D-amino acid
<220> FEATURE:
<221> NAME/KEY: MISC_FEATURE
<222> LOCATION: (11)..(11)
<223> OTHER INFORMATION: Tic
<220> FEATURE:
<221> NAME/KEY: MISC_FEATURE
<222> LOCATION: (12)..(12)
<223> OTHER INFORMATION: NMe

<400> SEQUENCE: 31

Gly Gly Tyr Phe Leu Pro Ser Gln Xaa Ala Xaa Ser
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthesized Peptide Compound YW-179
<220> FEATURE:
<221> NAME/KEY: MISC_FEATURE
<222> LOCATION: (1)..(1)
<223> OTHER INFORMATION: Beta-amino acid
<220> FEATURE:
<221> NAME/KEY: BINDING
<222> LOCATION: (1)..(1)
<223> OTHER INFORMATION: Palm-PEG8
<220> FEATURE:
<221> NAME/KEY: MISC_FEATURE
<222> LOCATION: (2)..(2)
<223> OTHER INFORMATION: Beta-amino acid
<220> FEATURE:
<221> NAME/KEY: MISC_FEATURE
<222> LOCATION: (3)..(3)
<223> OTHER INFORMATION: D-amino acid-NMe
<220> FEATURE:
<221> NAME/KEY: MISC_FEATURE
<222> LOCATION: (5)..(5)
<223> OTHER INFORMATION: NMe
<220> FEATURE:
<221> NAME/KEY: MISC_FEATURE
```

```
<222> LOCATION: (7)..(7)
<223> OTHER INFORMATION: D-amino acid
<220> FEATURE:
<221> NAME/KEY: MISC_FEATURE
<222> LOCATION: (9)..(9)
<223> OTHER INFORMATION: 2Nal
<220> FEATURE:
<221> NAME/KEY: MISC_FEATURE
<222> LOCATION: (10)..(10)
<223> OTHER INFORMATION: D-amino acid
<220> FEATURE:
<221> NAME/KEY: MISC_FEATURE
<222> LOCATION: (11)..(11)
<223> OTHER INFORMATION: Tic
<220> FEATURE:
<221> NAME/KEY: MISC_FEATURE
<222> LOCATION: (12)..(12)
<223> OTHER INFORMATION: NMe

<400> SEQUENCE: 32

Ala Ala Tyr Phe Leu Pro Ser Gln Xaa Ala Xaa Ser
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthesized Peptide Compound YW-180
<220> FEATURE:
<221> NAME/KEY: BINDING
<222> LOCATION: (1)..(1)
<223> OTHER INFORMATION: Tetradecanoyl-PEG8
<220> FEATURE:
<221> NAME/KEY: MISC_FEATURE
<222> LOCATION: (1)..(1)
<223> OTHER INFORMATION: Beta-amino acid
<220> FEATURE:
<221> NAME/KEY: MISC_FEATURE
<222> LOCATION: (2)..(2)
<223> OTHER INFORMATION: Beta-amino acid
<220> FEATURE:
<221> NAME/KEY: MISC_FEATURE
<222> LOCATION: (3)..(3)
<223> OTHER INFORMATION: D-amino acid-NMe
<220> FEATURE:
<221> NAME/KEY: MISC_FEATURE
<222> LOCATION: (5)..(5)
<223> OTHER INFORMATION: NMe
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (9)..(9)
<223> OTHER INFORMATION: 2Nal
<220> FEATURE:
<221> NAME/KEY: MISC_FEATURE
<222> LOCATION: (10)..(10)
<223> OTHER INFORMATION: D-amino acid
<220> FEATURE:
<221> NAME/KEY: MISC_FEATURE
<222> LOCATION: (11)..(11)
<223> OTHER INFORMATION: Tic
<220> FEATURE:
<221> NAME/KEY: MISC_FEATURE
<222> LOCATION: (12)..(12)
<223> OTHER INFORMATION: NMe

<400> SEQUENCE: 33

Ala Ala Tyr Phe Leu Pro Ser Gln Xaa Ala Xaa Ser
1               5                   10

<210> SEQ ID NO 34
```

```
<211> LENGTH: 12
<212> TYPE: PRT
<213> ORGANISM: Artificial Sequence
<220> FEATURE:
<223> OTHER INFORMATION: Synthesized Peptide Compound YW-181
<220> FEATURE:
<221> NAME/KEY: BINDING
<222> LOCATION: (1)..(1)
<223> OTHER INFORMATION: Dodecanoyl-PEG8
<220> FEATURE:
<221> NAME/KEY: MISC_FEATURE
<222> LOCATION: (1)..(1)
<223> OTHER INFORMATION: Beta-amino acid
<220> FEATURE:
<221> NAME/KEY: MISC_FEATURE
<222> LOCATION: (2)..(2)
<223> OTHER INFORMATION: Beta-amino acid
<220> FEATURE:
<221> NAME/KEY: MISC_FEATURE
<222> LOCATION: (3)..(3)
<223> OTHER INFORMATION: NMe-D-amino acid
<220> FEATURE:
<221> NAME/KEY: MISC_FEATURE
<222> LOCATION: (5)..(5)
<223> OTHER INFORMATION: NMe
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (9)..(9)
<223> OTHER INFORMATION: 2Nal
<220> FEATURE:
<221> NAME/KEY: MISC_FEATURE
<222> LOCATION: (10)..(10)
<223> OTHER INFORMATION: D-amino acid
<220> FEATURE:
<221> NAME/KEY: MISC_FEATURE
<222> LOCATION: (11)..(11)
<223> OTHER INFORMATION: Tic
<220> FEATURE:
<221> NAME/KEY: MISC_FEATURE
<222> LOCATION: (12)..(12)
<223> OTHER INFORMATION: NMe

<400> SEQUENCE: 34

Ala Ala Tyr Phe Leu Pro Ser Gln Xaa Ala Xaa Ser
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthesized Peptide Compound YW-182
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: D-Tic
<220> FEATURE:
```

```
<221> NAME/KEY: MISC_FEATURE
<222> LOCATION: (10)..(10)
<223> OTHER INFORMATION: NMe

<400> SEQUENCE: 35

Tyr Phe Leu Pro Ser Gln Phe Ala Xaa Ser
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthesized Peptide Compound YW-183
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NEt
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 36

Tyr Phe Leu Pro Ser Gln Phe Ala Xaa Ser
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Synthesized Peptide Compound YW-184
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NPr
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 37

Tyr Phe Leu Pro Ser Gln Phe Ala Xaa Ser
1               5                   10

<210> SEQ ID NO 38
<211> LENGTH: 10
<212> TYPE: PRT
```

```
<213> ORGANISM: Artificial Sequence
<220> FEATURE:
<223> OTHER INFORMATION: Synthesized Peptide Compound YW-185
<220> FEATURE:
<221> NAME/KEY: BINDING
<222> LOCATION: (1)..(1)
<223> OTHER INFORMATION: 3-Phenylpropanoyl
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NEt
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 38

Tyr Phe Leu Pro Ser Gln Phe Ala Xaa Ser
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthesized Peptide Compound YW-186
<220> FEATURE:
<221> NAME/KEY: BINDING
<222> LOCATION: (1)..(1)
<223> OTHER INFORMATION: 3-Phenylpropanoyl
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NPr
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 39

Tyr Phe Leu Pro Ser Gln Phe Ala Xaa Ser
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthesized Peptide Compound YW-190
<220> FEATURE:
<221> NAME/KEY: MISC_FEATURE
```

```
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: D-Tic
<220> FEATURE:
<221> NAME/KEY: BINDING
<222> LOCATION: (10)..(10)
<223> OTHER INFORMATION: NH2

<400> SEQUENCE: 40

Tyr Phe Leu Pro Ser Gln Phe Ala Xaa Ser
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthesized Peptide Compound YW-192
<220> FEATURE:
<221> NAME/KEY: BINDING
<222> LOCATION: (1)..(1)
<223> OTHER INFORMATION: DiMe
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 41

Tyr Phe Leu Pro Ser Gln Phe Ala Xaa Ser
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthesized Peptide Compound YW-193
<220> FEATURE:
<221> NAME/KEY: BINDING
<222> LOCATION: (1)..(1)
<223> OTHER INFORMATION: Hexanoyl
<220> FEATURE:
<221> NAME/KEY: MISC_FEATURE
<222> LOCATION: (1)..(1)
```

```
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 42

Tyr Phe Leu Pro Ser Gln Phe Ala Xaa Ser
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthesized Peptide Compound YW-194
<220> FEATURE:
<221> NAME/KEY: BINDING
<222> LOCATION: (1)..(1)
<223> OTHER INFORMATION: 2-Cyclohexylacetyl
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 43

Tyr Phe Leu Pro Ser Gln Phe Ala Xaa Ser
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthesized Peptide Compound YW-195
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: BINDING
<222> LOCATION: (1)..(1)
<223> OTHER INFORMATION: 4-(Trifluoromethyl)benzoyl
<220> FEATURE:
<221> NAME/KEY: MISC_FEATURE
<222> LOCATION: (3)..(3)
<223> OTHER INFORMATION: NMe
```

```
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 44

Tyr Phe Leu Pro Ser Gln Phe Ala Xaa Ser
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthesized Peptide Compound YW-198
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (4)..(4)
<223> OTHER INFORMATION: Hyp
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 45

Tyr Phe Leu Xaa Ser Gln Phe Ala Xaa Ser
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthesized Peptide Compound YW-199
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (2)..(2)
<223> OTHER INFORMATION: 1Nal
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
```

```
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 46

Tyr Xaa Leu Pro Ser Gln Phe Ala Xaa Ser
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthesized Peptide Compound YW-200
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (2)..(2)
<223> OTHER INFORMATION: 2Nal
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 47

Tyr Xaa Leu Pro Ser Gln Phe Ala Xaa Ser
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthesized Peptide Compound YW-201
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (2)..(2)
<223> OTHER INFORMATION: Bpa
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
```

```
<222> LOCATION: (9)..(9)
<223> OTHER INFORMATION: Tic

<400> SEQUENCE: 48

Tyr Xaa Leu Pro Ser Gln Phe Ala Xaa Ser
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthesized Peptide Compound YW-202
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (2)..(2)
<223> OTHER INFORMATION: 4-Me
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 49

Tyr Phe Leu Pro Ser Gln Phe Ala Xaa Ser
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthesized Peptide Compound YW-203
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (2)..(2)
<223> OTHER INFORMATION: 4-Cl
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 50
```

-continued

```
Tyr Phe Leu Pro Ser Gln Phe Ala Xaa Ser
1               5                   10
```

<210> SEQ ID NO 51
<211> LENGTH: 10
<212> TYPE: PRT
<213> ORGANISM: Artificial Sequence
<220> FEATURE:
<223> OTHER INFORMATION: Synthesized Peptide Compound YW-204
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-Thr
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 51

```
Tyr Phe Leu Pro Thr Gln Phe Ala Xaa Ser
1               5                   10
```

<210> SEQ ID NO 52
<211> LENGTH: 10
<212> TYPE: PRT
<213> ORGANISM: Artificial Sequence
<220> FEATURE:
<223> OTHER INFORMATION: Synthesized Peptide Compound YW-205
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: BINDING
<222> LOCATION: (9)..(9)
<223> OTHER INFORMATION: 4-Me

<400> SEQUENCE: 52

```
Tyr Phe Leu Pro Ser Gln Phe Ala Phe Ser
1               5                   10
```

<210> SEQ ID NO 53
<211> LENGTH: 10
<212> TYPE: PRT
<213> ORGANISM: Artificial Sequence
<220> FEATURE:
<223> OTHER INFORMATION: Synthesized Peptide Compound YW-206
<220> FEATURE:
<221> NAME/KEY: MISC_FEATURE
<222> LOCATION: (1)..(1)

```
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: BINDING
<222> LOCATION: (9)..(9)
<223> OTHER INFORMATION: 4-Cl

<400> SEQUENCE: 53

Tyr Phe Leu Pro Ser Gln Phe Ala Phe Ser
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthesized Peptide Compound YW-207
<220> FEATURE:
<221> NAME/KEY: BINDING
<222> LOCATION: (1)..(1)
<223> OTHER INFORMATION: 3-Phenylpropanoyl
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 54

Tyr Phe Leu Pro Ser Gln Phe Ala Xaa Ser
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthesized Peptide Compound YW-210
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: BINDING
<222> LOCATION: (4)..(4)
<223> OTHER INFORMATION: 4Ph
```

```
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 2Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 55

Tyr Phe Leu Pro Ser Gln Xaa Ala Xaa Ser
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Synthesized Peptide Compound YW-215
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: BINDING
<222> LOCATION: (4)..(4)
<223> OTHER INFORMATION: 4Ph
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 56

Tyr Phe Leu Pro Ser Gln Phe Ala Xaa Ser
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Synthesized Peptide Compound YW-216
<220> FEATURE:
<221> NAME/KEY: MISC_FEATURE
<222> LOCATION: (1)..(1)
<223> OTHER INFORMATION: D-amino acid-NMe
<220> FEATURE:
<221> NAME/KEY: MISC_FEATURE
<222> LOCATION: (3)..(3)
<223> OTHER INFORMATION: NMe
<220> FEATURE:
<221> NAME/KEY: BINDING
<222> LOCATION: (4)..(4)
<223> OTHER INFORMATION: 4Ph
<220> FEATURE:
```

```
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 2Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 57

Tyr Phe Leu Pro Ser Gln Xaa Ala Xaa Ser
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthesized Peptide Compound YW-217
<220> FEATURE:
<221> NAME/KEY: BINDING
<222> LOCATION: (1)..(1)
<223> OTHER INFORMATION: Palm-PEG8
<220> FEATURE:
<221> NAME/KEY: MISC_FEATURE
<222> LOCATION: (1)..(1)
<223> OTHER INFORMATION: Beta-amino acid
<220> FEATURE:
<221> NAME/KEY: MISC_FEATURE
<222> LOCATION: (2)..(2)
<223> OTHER INFORMATION: Beta-amino acid
<220> FEATURE:
<221> NAME/KEY: MISC_FEATURE
<222> LOCATION: (3)..(3)
<223> OTHER INFORMATION: D-amino acid-NMe
<220> FEATURE:
<221> NAME/KEY: MISC_FEATURE
<222> LOCATION: (5)..(5)
<223> OTHER INFORMATION: NMe
<220> FEATURE:
<221> NAME/KEY: BINDING
<222> LOCATION: (6)..(6)
<223> OTHER INFORMATION: 4Ph
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (9)..(9)
<223> OTHER INFORMATION: 2Nal
<220> FEATURE:
<221> NAME/KEY: MISC_FEATURE
<222> LOCATION: (10)..(10)
<223> OTHER INFORMATION: D-amino acid
<220> FEATURE:
<221> NAME/KEY: MISC_FEATURE
<222> LOCATION: (11)..(11)
<223> OTHER INFORMATION: Tic

<400> SEQUENCE: 58

Ala Ala Tyr Phe Leu Pro Ser Gln Xaa Ala Xaa Ser
1               5                   10

<210> SEQ ID NO 59
<211> LENGTH: 10
<212> TYPE: PRT
<213> ORGANISM: Artificial Sequence
```

```
<220> FEATURE:
<223> OTHER INFORMATION: Synthesized Peptide Compound YW-219
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: BINDING
<222> LOCATION: (4)..(4)
<223> OTHER INFORMATION: 4Ph
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 2Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 59

Tyr Phe Leu Pro Ser Gln Xaa Ala Xaa Ser
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthesized Peptide Compound YW-220
<220> FEATURE:
<221> NAME/KEY: MISC_FEATURE
<222> LOCATION: (1)..(1)
<223> OTHER INFORMATION: D-amino acid-NMe
<220> FEATURE:
<221> NAME/KEY: MISC_FEATURE
<222> LOCATION: (3)..(3)
<223> OTHER INFORMATION: NMe
<220> FEATURE:
<221> NAME/KEY: BINDING
<222> LOCATION: (4)..(4)
<223> OTHER INFORMATION: 4Ph
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 2Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: NMe

<400> SEQUENCE: 60

Tyr Phe Leu Pro Ser Gln Xaa Ala Xaa Ser
```

```
<210> SEQ ID NO 61
<211> LENGTH: 10
<212> TYPE: PRT
<213> ORGANISM: Artificial Sequence
<220> FEATURE:
<223> OTHER INFORMATION: Synthesized Peptide Compound YW-221
<220> FEATURE:
<221> NAME/KEY: BINDING
<222> LOCATION: (1)..(1)
<223> OTHER INFORMATION: 3F
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: BINDING
<222> LOCATION: (4)..(4)
<223> OTHER INFORMATION: 4Ph
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 2Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: NMe

<400> SEQUENCE: 61

Tyr Phe Leu Pro Ser Gln Xaa Ala Xaa Ser
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Synthesized Peptide Compound YW-221
<220> FEATURE:
<221> NAME/KEY: BINDING
<222> LOCATION: (1)..(1)
<223> OTHER INFORMATION: 3F
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: BINDING
<222> LOCATION: (4)..(4)
<223> OTHER INFORMATION: 4Ph
<220> FEATURE:
<221> NAME/KEY: MISC_FEATURE
<222> LOCATION: (5)..(5)
<223> OTHER INFORMATION: D-amino acid
<220> FEATURE:
```

```
<221> NAME/KEY: MISC_FEATURE
<222> LOCATION: (7)..(7)
<223> OTHER INFORMATION: 2Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 62

Tyr Phe Leu Pro Ser Gln Xaa Ala Xaa Ser
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Synthesized Peptide Compound YW-223
<220> FEATURE:
<221> NAME/KEY: BINDING
<222> LOCATION: (1)..(1)
<223> OTHER INFORMATION: Palm-PEG
<220> FEATURE:
<221> NAME/KEY: MISC_FEATURE
<222> LOCATION: (3)..(3)
<223> OTHER INFORMATION: D-amino acid
<220> FEATURE:
<221> NAME/KEY: MISC_FEATURE
<222> LOCATION: (5)..(5)
<223> OTHER INFORMATION: NMe
<220> FEATURE:
<221> NAME/KEY: BINDING
<222> LOCATION: (6)..(6)
<223> OTHER INFORMATION: 4Ph
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (9)..(9)
<223> OTHER INFORMATION: 2Nal
<220> FEATURE:
<221> NAME/KEY: MISC_FEATURE
<222> LOCATION: (10)..(10)
<223> OTHER INFORMATION: D-amino acid
<220> FEATURE:
<221> NAME/KEY: MISC_FEATURE
<222> LOCATION: (11)..(11)
<223> OTHER INFORMATION: Tic

<400> SEQUENCE: 63

Gly Gly Tyr Phe Leu Pro Ser Gln Xaa Ala Xaa Ser
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthesized Peptide Compound YW-224
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: BINDING
```

```
<222> LOCATION: (4)..(4)
<223> OTHER INFORMATION: diF
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 2Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: NMe

<400> SEQUENCE: 64

Tyr Phe Leu Pro Ser Gln Xaa Ala Xaa Ser
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthesized Peptide Compound YW-225
<220> FEATURE:
<221> NAME/KEY: MISC_FEATURE
<222> LOCATION: (1)..(1)
<223> OTHER INFORMATION: D-amino acid-NMe
<220> FEATURE:
<221> NAME/KEY: MISC_FEATURE
<222> LOCATION: (3)..(3)
<223> OTHER INFORMATION: NMe
<220> FEATURE:
<221> NAME/KEY: BINDING
<222> LOCATION: (4)..(4)
<223> OTHER INFORMATION: diF
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 2Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: NMe

<400> SEQUENCE: 65

Tyr Phe Leu Pro Ser Gln Xaa Ala Xaa Ser
1               5                   10

<210> SEQ ID NO 66
<211> LENGTH: 10
<212> TYPE: PRT
<213> ORGANISM: Artificial Sequence
<220> FEATURE:
```

```
<223> OTHER INFORMATION: Synthesized Peptide Compound YW-226
<220> FEATURE:
<221> NAME/KEY: BINDING
<222> LOCATION: (1)..(1)
<223> OTHER INFORMATION: 3F
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: BINDING
<222> LOCATION: (4)..(4)
<223> OTHER INFORMATION: diF
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 2Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: NMe

<400> SEQUENCE: 66

Tyr Phe Leu Pro Ser Gln Xaa Ala Xaa Ser
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Synthesized Peptide Compound YW-96
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (4)..(5)
<223> OTHER INFORMATION: S-Pip
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 67

Tyr Phe Leu Xaa Ser Gln Phe Ala Xaa Ser
1               5                   10

<210> SEQ ID NO 68
<211> LENGTH: 10
```

```
<212> TYPE: PRT
<213> ORGANISM: Artificial Sequence
<220> FEATURE:
<223> OTHER INFORMATION: Synthesized Peptide Compound YW-97
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 68

Phe Phe Leu Pro Ser Gln Phe Ala Xaa Ser
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthesized Peptide Compound YW-103
<220> FEATURE:
<221> NAME/KEY: MISC_FEATURE
<222> LOCATION: (1)..(1)
<223> OTHER INFORMATION: D-amino acid-NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 69

Tyr Phe Leu Pro Ser Gln Phe Ala Xaa Ser
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Synthesized Peptide Compound YW-104
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (2)..(2)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
```

```
<221> NAME/KEY: MISC_FEATURE
<222> LOCATION: (9)..(9)
<223> OTHER INFORMATION: Tic

<400> SEQUENCE: 70

Tyr Phe Leu Pro Ser Gln Phe Ala Xaa Ser
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Synthesized Peptide Compound YW-110
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: NMe

<400> SEQUENCE: 71

Tyr Phe Leu Pro Ser Gln Phe Ala Xaa Ser
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Synthesized Peptide Compound YW-112
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: BINDING
<222> LOCATION: (4)..(4)
<223> OTHER INFORMATION: 5-phenyl
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 72

Tyr Phe Leu Pro Ser Gln Phe Ala Xaa Ser
1               5                   10

<210> SEQ ID NO 73
<211> LENGTH: 10
<212> TYPE: PRT
```

```
<213> ORGANISM: Artificial Sequence
<220> FEATURE:
<223> OTHER INFORMATION: Synthesized Peptide Compound YW-113
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: BINDING
<222> LOCATION: (4)..(4)
<223> OTHER INFORMATION: 4-phenyl
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 73

Tyr Phe Leu Pro Ser Gln Phe Ala Xaa Ser
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Synthesized Peptide Compound YW-114
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (4)..(4)
<223> OTHER INFORMATION: Thz
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: misc_feature
<222> LOCATION: (9)..(9)
<223> OTHER INFORMATION: Tic

<400> SEQUENCE: 74

Tyr Phe Leu Xaa Ser Gln Phe Ala Xaa Ser
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthesized Peptide Compound YW-115
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (4)..(4)
<223> OTHER INFORMATION: Aze
<220> FEATURE:
<221> NAME/KEY: MISC_FEATURE
```

```
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 75

Tyr Phe Leu Xaa Ser Gln Phe Ala Xaa Ser
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Synthesized Peptide Compound YW-117
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 1Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 76

Tyr Phe Leu Pro Ser Gln Xaa Ala Xaa Ser
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Synthesized Peptide Compound YW-118
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 2Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 77
```

Tyr Phe Leu Pro Ser Gln Xaa Ala Xaa Ser
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Synthesized Peptide Compound YW-119
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: Bpa
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 78

Tyr Phe Leu Pro Ser Gln Xaa Ala Xaa Ser
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Synthesized Peptide Compound YW-149
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: D-Tic

<400> SEQUENCE: 79

Tyr Phe Leu Pro Ser Gln Phe Ala Xaa Ser
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Synthesized Peptide Compound YW-150
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)

```
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Ti1c

<400> SEQUENCE: 80

Tyr Phe Leu Pro Ser Gln Phe Ala Xaa Ser
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Synthesized Peptide Compound YW-151
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: D-Ti1c

<400> SEQUENCE: 81

Tyr Phe Leu Pro Ser Gln Phe Ala Xaa Ser
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthesized Peptide Compound YW-154
<220> FEATURE:
<221> NAME/KEY: MISC_FEATURE
<222> LOCATION: (1)..(1)
<223> OTHER INFORMATION: D-amino acid-NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: D-Ti1c

<400> SEQUENCE: 82

Tyr Phe Leu Pro Ser Gln Phe Ala Xaa Ser
1               5                   10

<210> SEQ ID NO 83
<211> LENGTH: 10
<212> TYPE: PRT
<213> ORGANISM: Artificial Sequence
<220> FEATURE:
```

```
<223> OTHER INFORMATION: Synthesized Peptide Compound YW-158
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: TP5C

<400> SEQUENCE: 83

Tyr Phe Leu Pro Ser Gln Phe Ala Xaa Ser
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Synthesized Peptide Compound YW-159
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: TP6C

<400> SEQUENCE: 84

Tyr Phe Leu Pro Ser Gln Phe Ala Xaa Ser
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Synthesized Peptide Compound YW-189
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: BINDING
<222> LOCATION: (10)..(10)
<223> OTHER INFORMATION: NH2
```

-continued

<400> SEQUENCE: 85

Tyr Phe Leu Pro Ser Gln Phe Ala Xaa Ser
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthesized Peptide Compound YW-196
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: Nva
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 86

Tyr Phe Xaa Pro Ser Gln Phe Ala Xaa Ser
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Synthesized Peptide Compound YW-197
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: Nle
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 87

Tyr Phe Xaa Pro Ser Gln Phe Ala Xaa Ser
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Synthesized Peptide Compound YW-71

```
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: BINDING
<222> LOCATION: (1)..(1)
<223> OTHER INFORMATION: 3-Phenylpropanoyl
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 88

Tyr Phe Leu Pro Ser Gln Phe Ala Xaa Ser
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Synthesized Peptide Compound YW-72
<220> FEATURE:
<221> NAME/KEY: BINDING
<222> LOCATION: (1)..(1)
<223> OTHER INFORMATION: Phenethylcarbamoyl
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 89

Tyr Phe Leu Pro Ser Gln Phe Ala Xaa Ser
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Synthesized Peptide Compound YW-73
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: BINDING
<222> LOCATION: (1)..(1)
<223> OTHER INFORMATION: Phenethylcarbamothioyl
<220> FEATURE:
<221> NAME/KEY: MISC_FEATURE
<222> LOCATION: (5)..(5)
<223> OTHER INFORMATION: D-amino acid
<220> FEATURE:
```

```
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 90

Tyr Phe Leu Pro Ser Gln Phe Ala Xaa Ser
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Synthesized Peptide Compound YW-74
<220> FEATURE:
<221> NAME/KEY: BINDING
<222> LOCATION: (1)..(1)
<223> OTHER INFORMATION: 3-Phenylpropyl
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 91

Tyr Phe Leu Pro Ser Gln Phe Ala Xaa Ser
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthesized Peptide Compound YW-75
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: BINDING
<222> LOCATION: (1)..(1)
<223> OTHER INFORMATION: 4-Phenylbutanoyl
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 92

Tyr Phe Leu Pro Ser Gln Phe Ala Xaa Ser
1               5                   10
```

```
<210> SEQ ID NO 93
<211> LENGTH: 10
<212> TYPE: PRT
<213> ORGANISM: Artificial Sequence
<220> FEATURE:
<223> OTHER INFORMATION: Synthesized Peptide Compound YW-76
<220> FEATURE:
<221> NAME/KEY: BINDING
<222> LOCATION: (1)..(1)
<223> OTHER INFORMATION: 5-Phenylpentanoyl
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 93

Tyr Phe Leu Pro Ser Gln Phe Ala Xaa Ser
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Synthesized Peptide Compound YW-77
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: BINDING
<222> LOCATION: (1)..(1)
<223> OTHER INFORMATION: 4-Biphenylacetyl
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 94

Tyr Phe Leu Pro Ser Gln Phe Ala Xaa Ser
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Synthesized Peptide Compound YW-78
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: BINDING
```

-continued

```
<222> LOCATION: (1)..(1)
<223> OTHER INFORMATION: Diphenylacetyl
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 95

Tyr Phe Leu Pro Ser Gln Phe Ala Xaa Ser
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Synthesized Peptide Compound YW-79
<220> FEATURE:
<221> NAME/KEY: BINDING
<222> LOCATION: (1)..(1)
<223> OTHER INFORMATION: 3,5-Dihydroxybenzoyl
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 96

Tyr Phe Leu Pro Ser Gln Phe Ala Xaa Ser
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Synthesized Peptide Compound YW-127
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: BINDING
<222> LOCATION: (1)..(1)
<223> OTHER INFORMATION: 2,3-Dihydroxybenzoyl
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
```

```
<223> OTHER INFORMATION: Tic

<400> SEQUENCE: 97

Tyr Phe Leu Pro Ser Gln Phe Ala Xaa Ser
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Synthesized Peptide Compound YW-128
<220> FEATURE:
<221> NAME/KEY: BINDING
<222> LOCATION: (1)..(1)
<223> OTHER INFORMATION: 2,6-Dihydroxybenzoyl
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 98

Tyr Phe Leu Pro Ser Gln Phe Ala Xaa Ser
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Synthesized Peptide Compound YW-129
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: BINDING
<222> LOCATION: (1)..(1)
<223> OTHER INFORMATION: 2,3,4-Trihydroxybenzoy
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 99

Tyr Phe Leu Pro Ser Gln Phe Ala Xaa Ser
1               5                   10

<210> SEQ ID NO 100
<211> LENGTH: 10
<212> TYPE: PRT
<213> ORGANISM: Artificial Sequence
<220> FEATURE:
```

```
<223> OTHER INFORMATION: Synthesized Peptide Compound YW-131
<220> FEATURE:
<221> NAME/KEY: BINDING
<222> LOCATION: (1)..(1)
<223> OTHER INFORMATION: 3,5-Dihydroxyphenylacetyl
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 100

Tyr Phe Leu Pro Ser Gln Phe Ala Xaa Ser
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Synthesized Peptide Compound YW-132
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: BINDING
<222> LOCATION: (1)..(1)
<223> OTHER INFORMATION: 3,4-Dihydroxyphenylacetyl
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 101

Tyr Phe Leu Pro Ser Gln Phe Ala Xaa Ser
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Synthesized Peptide Compound YW-3
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
```

```
<220> FEATURE:
<221> NAME/KEY: MISC_FEATURE
<222> LOCATION: (9)..(9)
<223> OTHER INFORMATION: Tic

<400> SEQUENCE: 102

Tyr Phe Leu Pro Ser Gln Phe Ala Xaa Ser
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Synthesized Peptide Compound YW-90
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: S-Pip

<400> SEQUENCE: 103

Tyr Phe Leu Pro Ser Gln Phe Ala Xaa Ser
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Synthesized Peptide Compound YW-91
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: 5-phenyl

<400> SEQUENCE: 104

Tyr Phe Leu Pro Ser Gln Phe Ala Pro Ser
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Synthesized Peptide Compound YW-92
<220> FEATURE:
<221> NAME/KEY: MISC_FEATURE
<222> LOCATION: (1)..(1)
<223> OTHER INFORMATION: D-amino acid
```

```
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: 4-phenyl

<400> SEQUENCE: 105

Tyr Phe Leu Pro Ser Gln Phe Ala Pro Ser
1               5                   10

<210> SEQ ID NO 106
<211> LENGTH: 9
<212> TYPE: PRT
<213> ORGANISM: Artificial Sequence
<220> FEATURE:
<223> OTHER INFORMATION: Synthesized Peptide Compound YW-93
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (8)..(8)
<223> OTHER INFORMATION: (S)-isoindoline-1-carboxylic acid

<400> SEQUENCE: 106

Tyr Phe Leu Pro Ser Gln Ala Xaa Ser
1               5

<210> SEQ ID NO 107
<211> LENGTH: 10
<212> TYPE: PRT
<213> ORGANISM: Artificial Sequence
<220> FEATURE:
<223> OTHER INFORMATION: Synthesized Peptide Compound YW-94
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: dip

<400> SEQUENCE: 107

Tyr Phe Leu Pro Ser Gln Phe Ala Ala Ser
1               5                   10

<210> SEQ ID NO 108
<211> LENGTH: 10
```

```
<212> TYPE: PRT
<213> ORGANISM: Artificial Sequence
<220> FEATURE:
<223> OTHER INFORMATION: Synthesized Peptide Compound YW-95
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Bip

<400> SEQUENCE: 108

Tyr Phe Leu Pro Ser Gln Phe Ala Xaa Ser
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Synthesized Peptide Compound YW-99
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 109

Tyr Phe Val Pro Ser Gln Phe Ala Xaa Ser
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Synthesized Peptide Compound YW-102
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: NLeu
<220> FEATURE:
<221> NAME/KEY: MISC_FEATURE
<222> LOCATION: (5)..(5)
<223> OTHER INFORMATION: D-amino acid
<220> FEATURE:
```

```
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 110

Tyr Phe Leu Pro Ser Gln Phe Ala Xaa Ser
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Synthesized Peptide Compound YW-106
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (5)..(5)
<223> OTHER INFORMATION: NMe
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 111

Tyr Phe Leu Pro Ser Gln Phe Ala Xaa Ser
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Synthesized Peptide Compound YW-107
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (6)..(6)
<223> OTHER INFORMATION: NMe
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 112

Tyr Phe Leu Pro Ser Gln Phe Ala Xaa Ser
1               5                   10
```

```
<210> SEQ ID NO 113
<211> LENGTH: 10
<212> TYPE: PRT
<213> ORGANISM: Artificial Sequence
<220> FEATURE:
<223> OTHER INFORMATION: Synthesized Peptide Compound YW-108
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (6)..(6)
<223> OTHER INFORMATION: NGln
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 113

Tyr Phe Leu Pro Ser Gln Phe Ala Xaa Ser
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Synthesized Peptide Compound YW-109
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (8)..(8)
<223> OTHER INFORMATION: NMe
<220> FEATURE:
<221> NAME/KEY: MISC_FEATURE
<222> LOCATION: (9)..(9)
<223> OTHER INFORMATION: Tic

<400> SEQUENCE: 114

Tyr Phe Leu Pro Ser Gln Phe Ala Xaa Ser
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Synthesized Peptide Compound YW-147
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
```

```
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: azaTic

<400> SEQUENCE: 115

Tyr Phe Leu Pro Ser Gln Ser Ala Xaa Ser
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Synthesized Peptide Compound YW-155
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (8)..(8)
<223> OTHER INFORMATION: NMe
<220> FEATURE:
<221> NAME/KEY: MISC_FEATURE
<222> LOCATION: (9)..(9)
<223> OTHER INFORMATION: D-Tilc
<220> FEATURE:
<221> NAME/KEY: MISC_FEATURE
<222> LOCATION: (10)..(10)
<223> OTHER INFORMATION: NMe

<400> SEQUENCE: 116

Tyr Phe Leu Pro Ser Gln Ser Ala Xaa Ser
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Synthesized Peptide Compound YW-156
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
```

```
<223> OTHER INFORMATION: D-Tilc

<400> SEQUENCE: 117

Tyr Phe Leu Pro Xaa Gln Phe Ala Xaa Ser
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Synthesized Peptide Compound YW-157
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: 1Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: D-Tilc

<400> SEQUENCE: 118

Tyr Phe Leu Pro Xaa Gln Phe Ala Xaa Ser
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Synthesized Peptide Compound YW-160
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic

<400> SEQUENCE: 119

Tyr Phe Leu Pro Ser Gln Phe Ala Xaa Thr
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Synthesized Peptide Compound YW-126
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
```

```
<223> OTHER INFORMATION: 3,5-dihydroxybenzoyl
<220> FEATURE:
<221> NAME/KEY: MISC_FEATURE
<222> LOCATION: (1)..(1)
<223> OTHER INFORMATION: NMe
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (4)..(4)
<223> OTHER INFORMATION: Thz
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: 2Nal
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: NMe

<400> SEQUENCE: 120

Tyr Phe Leu Xaa Ser Gln Xaa Ala Xaa Ser
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Synthesized Peptide Intermediate 1
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: tBu
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (5)..(5)
<223> OTHER INFORMATION: tBu
<220> FEATURE:
<221> NAME/KEY: MISC_FEATURE
<222> LOCATION: (6)..(6)
<223> OTHER INFORMATION: Trt
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: tBu
```

```
<400> SEQUENCE: 121

Tyr Phe Leu Pro Ser Gln Phe Ala Xaa Ser
1               5                   10

<210> SEQ ID NO 122
<211> LENGTH: 7
<212> TYPE: PRT
<213> ORGANISM: Artificial Sequence
<220> FEATURE:
<223> OTHER INFORMATION: Synthesized Peptide Intermediate 2
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (2)..(2)
<223> OTHER INFORMATION: tBu
<220> FEATURE:
<221> NAME/KEY: MISC_FEATURE
<222> LOCATION: (3)..(3)
<223> OTHER INFORMATION: Trt
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (6)..(6)
<223> OTHER INFORMATION: Tic
<220> FEATURE:
<221> NAME/KEY: MISC_FEATURE
<222> LOCATION: (7)..(7)
<223> OTHER INFORMATION: tBu

<400> SEQUENCE: 122

Pro Ser Gln Phe Ala Xaa Ser
1               5

<210> SEQ ID NO 123
<211> LENGTH: 8
<212> TYPE: PRT
<213> ORGANISM: Artificial Sequence
<220> FEATURE:
<223> OTHER INFORMATION: Synthesized Peptide Intermediate 3
<220> FEATURE:
<221> NAME/KEY: MISC_FEATURE
<222> LOCATION: (1)..(1)
<223> OTHER INFORMATION: NLeu
<220> FEATURE:
<221> NAME/KEY: MISC_FEATURE
<222> LOCATION: (3)..(3)
<223> OTHER INFORMATION: D-amino acid
<220> FEATURE:
<221> NAME/KEY: MISC_FEATURE
<222> LOCATION: (3)..(3)
<223> OTHER INFORMATION: tBu
<220> FEATURE:
<221> NAME/KEY: MISC_FEATURE
<222> LOCATION: (4)..(4)
<223> OTHER INFORMATION: Trt
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: MISC_FEATURE
<222> LOCATION: (7)..(7)
<223> OTHER INFORMATION: Tic
<220> FEATURE:
<221> NAME/KEY: MISC_FEATURE
<222> LOCATION: (8)..(8)
<223> OTHER INFORMATION: tBu

<400> SEQUENCE: 123
```

```
Leu Pro Ser Gln Phe Ala Xaa Ser
1               5

<210> SEQ ID NO 124
<211> LENGTH: 5
<212> TYPE: PRT
<213> ORGANISM: Artificial Sequence
<220> FEATURE:
<223> OTHER INFORMATION: Synthesized Peptide Intermediate 4
<220> FEATURE:
<221> NAME/KEY: MISC_FEATURE
<222> LOCATION: (1)..(1)
<223> OTHER INFORMATION: NGln
<220> FEATURE:
<221> NAME/KEY: MISC_FEATURE
<222> LOCATION: (3)..(3)
<223> OTHER INFORMATION: D-amino acid
<220> FEATURE:
<221> NAME/KEY: MISC_FEATURE
<222> LOCATION: (4)..(4)
<223> OTHER INFORMATION: Tic
<220> FEATURE:
<221> NAME/KEY: MISC_FEATURE
<222> LOCATION: (5)..(5)
<223> OTHER INFORMATION: tBu

<400> SEQUENCE: 124

Gln Phe Ala Xaa Ser
1               5

<210> SEQ ID NO 125
<211> LENGTH: 10
<212> TYPE: PRT
<213> ORGANISM: Artificial Sequence
<220> FEATURE:
<223> OTHER INFORMATION: Synthesized Peptide Intermediate 5
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: tBu
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (5)..(5)
<223> OTHER INFORMATION: tBu
<220> FEATURE:
<221> NAME/KEY: MISC_FEATURE
<222> LOCATION: (6)..(6)
<223> OTHER INFORMATION: Trt
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (7)..(7)
<223> OTHER INFORMATION: tBu
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: azaTic
<220> FEATURE:
<221> NAME/KEY: MISC_FEATURE
<222> LOCATION: (10)..(10)
```

<223> OTHER INFORMATION: tBu

<400> SEQUENCE: 125

Tyr Phe Leu Pro Ser Gln Ser Ala Xaa Ser
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Synthesized Peptide Intermediate 6
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: tBu
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (5)..(5)
<223> OTHER INFORMATION: tBu
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: tBu
<220> FEATURE:
<221> NAME/KEY: MISC_FEATURE
<222> LOCATION: (10)..(10)
<223> OTHER INFORMATION: NHo

<400> SEQUENCE: 126

Tyr Phe Leu Pro Ser Gln Phe Ala Xaa Ser
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Synthesized Peptide Intermediate 7
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: tBu
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid

```
<220> FEATURE:
<221> NAME/KEY: MISC_FEATURE
<222> LOCATION: (5)..(5)
<223> OTHER INFORMATION: tBu
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: tBu
<220> FEATURE:
<221> NAME/KEY: MISC_FEATURE
<222> LOCATION: (10)..(10)
<223> OTHER INFORMATION: NMe
<220> FEATURE:
<221> NAME/KEY: MISC_FEATURE
<222> LOCATION: (10)..(10)
<223> OTHER INFORMATION: NHo

<400> SEQUENCE: 127

Tyr Phe Leu Pro Ser Gln Phe Ala Xaa Ser
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Synthesized Peptide Intermediate 8
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: tBu
<220> FEATURE:
<221> NAME/KEY: MISC_FEATURE
<222> LOCATION: (3)..(3)
<223> OTHER INFORMATION: NEt
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (5)..(5)
<223> OTHER INFORMATION: tBu
<220> FEATURE:
<221> NAME/KEY: MISC_FEATURE
<222> LOCATION: (6)..(6)
<223> OTHER INFORMATION: Trt
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: tBu

<400> SEQUENCE: 128

Tyr Phe Leu Pro Ser Gln Phe Ala Xaa Ser
1               5                   10
```

<210> SEQ ID NO 129
<211> LENGTH: 10
<212> TYPE: PRT
<213> ORGANISM: Artificial Sequence
<220> FEATURE:
<223> OTHER INFORMATION: Synthesized Peptide Intermediate 9
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: tBu
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (5)..(5)
<223> OTHER INFORMATION: tBu
<220> FEATURE:
<221> NAME/KEY: MISC_FEATURE
<222> LOCATION: (6)..(6)
<223> OTHER INFORMATION: Trt
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: tBu

<400> SEQUENCE: 129

Tyr Phe Leu Pro Ser Gln Phe Ala Xaa Ser
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Synthesized Peptide Intermediate 10
<220> FEATURE:
<221> NAME/KEY: MISC_FEATURE
<222> LOCATION: (1)..(1)
<223> OTHER INFORMATION: 3-phenyl propyl
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: tBu
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (5)..(5)

```
<223> OTHER INFORMATION: tBu
<220> FEATURE:
<221> NAME/KEY: MISC_FEATURE
<222> LOCATION: (6)..(6)
<223> OTHER INFORMATION: Trt
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: tBu

<400> SEQUENCE: 130

Tyr Phe Leu Pro Ser Gln Phe Ala Xaa Ser
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Synthesized Peptide Intermediate 11
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: tBu
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (5)..(5)
<223> OTHER INFORMATION: tBu
<220> FEATURE:
<221> NAME/KEY: MISC_FEATURE
<222> LOCATION: (6)..(6)
<223> OTHER INFORMATION: Trt
<220> FEATURE:
<221> NAME/KEY: MISC_FEATURE
<222> LOCATION: (7)..(7)
<223> OTHER INFORMATION: Nal-2
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: tBu

<400> SEQUENCE: 131

Tyr Phe Leu Pro Ser Gln Xaa Ala Xaa Ser
1               5                   10

<210> SEQ ID NO 132
<211> LENGTH: 10
```

```
<212> TYPE: PRT
<213> ORGANISM: Artificial Sequence
<220> FEATURE:
<223> OTHER INFORMATION: Synthesized Peptide Intermediate 12
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: 3F
<220> FEATURE:
<221> NAME/KEY: MISC_FEATURE
<222> LOCATION: (3)..(3)
<223> OTHER INFORMATION: NMe
<220> FEATURE:
<221> NAME/KEY: MISC_FEATURE
<222> LOCATION: (4)..(4)
<223> OTHER INFORMATION: tran-4F
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (5)..(5)
<223> OTHER INFORMATION: tBu
<220> FEATURE:
<221> NAME/KEY: MISC_FEATURE
<222> LOCATION: (6)..(6)
<223> OTHER INFORMATION: Trt
<220> FEATURE:
<221> NAME/KEY: MISC_FEATURE
<222> LOCATION: (7)..(7)
<223> OTHER INFORMATION: Nal-2
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: Tic
<220> FEATURE:
<221> NAME/KEY: MISC_FEATURE
<222> LOCATION: (10)..(10)
<223> OTHER INFORMATION: tBu

<400> SEQUENCE: 132

Tyr Phe Leu Pro Ser Gln Xaa Ala Xaa Ser
1               5                   10

<210> SEQ ID NO 133
<211> LENGTH: 9
<212> TYPE: PRT
<213> ORGANISM: Homo sapiens

<400> SEQUENCE: 133

Tyr Phe Pro Gly Gln Phe Ala Phe Ser
1               5

<210> SEQ ID NO 134
<211> LENGTH: 9
<212> TYPE: PRT
<213> ORGANISM: Mus musculus

<400> SEQUENCE: 134

Phe Leu Pro Gly Gln Phe Ala Phe Ser
1               5
```